US012558316B2

(12) United States Patent
Badiavas

(10) Patent No.: US 12,558,316 B2
(45) Date of Patent: *Feb. 24, 2026

(54) METHODS AND COMPOSITIONS FOR THE TREATMENT OF EPIDERMOLYSIS BULLOSA

(71) Applicant: UNIVERSITY OF MIAMI, Miami, FL (US)

(72) Inventor: Evangelos V. Badiavas, Coral Gables, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 708 days.

This patent is subject to a terminal disclaimer.

(21) Appl. No.: 15/712,294

(22) Filed: Sep. 22, 2017

(65) Prior Publication Data

US 2018/0104186 A1 Apr. 19, 2018

Related U.S. Application Data

(63) Continuation-in-part of application No. 14/775,382, filed as application No. PCT/US2014/024629 on Mar. 12, 2014, now Pat. No. 10,500,231.

(60) Provisional application No. 61/778,591, filed on Mar. 13, 2013.

(51) Int. Cl.

| | |
|---|---|
| *A61K 9/127* | (2025.01) |
| *A61K 9/00* | (2006.01) |
| *A61K 31/7088* | (2006.01) |
| *A61K 35/16* | (2015.01) |
| *A61K 35/22* | (2015.01) |
| *A61K 35/28* | (2015.01) |
| *A61K 38/18* | (2006.01) |
| *A61K 38/20* | (2006.01) |
| *A61K 38/21* | (2006.01) |
| *A61K 38/39* | (2006.01) |
| *A61K 38/45* | (2006.01) |
| *A61K 45/06* | (2006.01) |
| *A61K 47/46* | (2006.01) |
| *A61P 17/00* | (2006.01) |

(52) U.S. Cl.
CPC ............ *A61K 9/127* (2013.01); *A61K 9/0014* (2013.01); *A61K 31/7088* (2013.01); *A61K 35/16* (2013.01); *A61K 35/22* (2013.01); *A61K 35/28* (2013.01); *A61K 38/1808* (2013.01); *A61K 38/2033* (2013.01); *A61K 38/204* (2013.01); *A61K 38/21* (2013.01); *A61K 38/39* (2013.01); *A61K 38/45* (2013.01); *A61K 45/06* (2013.01); *A61K 47/46* (2013.01); *A61P 17/00* (2018.01); *C12Y 207/10002* (2013.01); *C12Y 207/11024* (2013.01)

(58) Field of Classification Search
None
See application file for complete search history.

(56) References Cited

U.S. PATENT DOCUMENTS

| | | | |
|---|---|---|---|
| 6,331,298 | B1 | 12/2001 | Ferguson et al. |
| 6,509,369 | B2 | 1/2003 | Scott et al. |
| 6,793,945 | B2 | 9/2004 | Bathurst et al. |
| 7,807,438 | B2 | 10/2010 | Abrignani et al. |
| 7,897,356 | B2 | 3/2011 | Klass et al. |
| 8,021,847 | B2 | 9/2011 | Pietrzkowski |
| 8,211,653 | B2 | 7/2012 | Klass et al. |
| 8,216,784 | B2 | 7/2012 | Taylor et al. |
| 8,278,059 | B2 | 10/2012 | Klass et al. |
| 8,288,172 | B2 | 10/2012 | Ichim et al. |
| 8,343,485 | B2 | 1/2013 | Pecora et al. |
| 8,343,725 | B2 | 1/2013 | Croce et al. |
| 8,349,560 | B2 | 1/2013 | Croce |
| 8,349,561 | B2 | 1/2013 | Croce |
| 8,349,568 | B2 | 1/2013 | Croce et al. |
| 8,349,574 | B2 | 1/2013 | Bates et al. |
| 8,901,284 | B2 | 12/2014 | Vlassov et al. |
| 9,005,888 | B2 | 4/2015 | Antes et al. |
| 9,066,971 | B2 | 6/2015 | Gho et al. |
| 9,828,603 | B2 | 11/2017 | Marban et al. |
| 9,856,477 | B2 | 1/2018 | Lotvall et al. |
| 10,500,231 | B2 | 12/2019 | Badiavas et al. |
| 11,730,768 | B2 | 8/2023 | Badiavas et al. |
| 2003/0198642 | A1 | 10/2003 | Geuze et al. |
| 2004/0132729 | A1 | 7/2004 | Salituro et al. |
| 2004/0171623 | A1 | 9/2004 | Reynolds et al. |
| 2004/0209901 | A1 | 10/2004 | Adams et al. |
| 2004/0220393 | A1 | 11/2004 | Ward et al. |
| 2006/0116321 | A1 | 6/2006 | Robbins et al. |
| 2008/0268429 | A1 | 10/2008 | Pietrzkowski |
| 2009/0292109 | A1 | 11/2009 | Gronke et al. |

(Continued)

FOREIGN PATENT DOCUMENTS

| | | | |
|---|---|---|---|
| CN | 101854941 | A | 10/2010 |
| CN | 105209881 | A | 12/2015 |

(Continued)

OTHER PUBLICATIONS

SystemBiosciences Exoquick-TC Exosome Precipitation Solution pp. 1-10, 2011 (Year: 2011).*

(Continued)

*Primary Examiner* — Teresa E Knight
(74) *Attorney, Agent, or Firm* — LATHROP GPM LLP; Laura A. Labeots

(57) ABSTRACT

The present invention provides compositions and methods for treating epidermolysis bullosa.

16 Claims, 52 Drawing Sheets

Specification includes a Sequence Listing.

(56) References Cited

U.S. PATENT DOCUMENTS

| | | | |
|---|---|---|---|
| 2010/0047335 | A1 | 2/2010 | Egea et al. |
| 2010/0104542 | A1 | 4/2010 | Austen, Jr. |
| 2010/0184046 | A1 | 7/2010 | Klass et al. |
| 2010/0189744 | A1 | 7/2010 | Bryan et al. |
| 2010/0196426 | A1 | 8/2010 | Skog et al. |
| 2010/0255514 | A1 | 10/2010 | Rak et al. |
| 2011/0003008 | A1 | 1/2011 | Lim |
| 2011/0195426 | A1 | 8/2011 | Russo et al. |
| 2012/0053976 | A1 | 3/2012 | Hu et al. |
| 2012/0058492 | A1 | 3/2012 | Lozupone et al. |
| 2012/0070858 | A1 | 3/2012 | Contreras et al. |
| 2012/0093885 | A1 | 4/2012 | Sahoo et al. |
| 2012/0171290 | A1 | 7/2012 | Coursaget et al. |
| 2012/0214151 | A1 | 8/2012 | Newman et al. |
| 2012/0238467 | A1 | 9/2012 | Taylor et al. |
| 2012/0309041 | A1 | 12/2012 | Timmers et al. |
| 2012/0315324 | A1 | 12/2012 | Zhang |
| 2013/0337440 | A1* | 12/2013 | Antes ................... C12Q 1/6895 |
| | | | 435/6.1 |
| 2016/0184363 | A1 | 6/2016 | Badiavas et al. |
| 2017/0258845 | A1* | 9/2017 | Lim ........................ A61P 17/00 |
| 2019/0133922 | A1 | 5/2019 | Kang et al. |
| 2020/0163999 | A1 | 5/2020 | Badiavas et al. |
| 2022/0072049 | A1 | 3/2022 | Badiavas et al. |
| 2023/0364150 | A1 | 11/2023 | Badiavas et al. |

FOREIGN PATENT DOCUMENTS

| | | | |
|---|---|---|---|
| EP | 1 780 267 A2 | 5/2007 | |
| EP | 2604288 A1 | 6/2013 | |
| EP | 2687219 A1 | 1/2014 | |
| EP | 2972193 A1 | 1/2016 | |
| EP | 3677271 A1 | 7/2020 | |
| EP | 3684336 A1 | 7/2020 | |
| JP | 2010-514433 A | 5/2010 | |
| JP | 2011-513217 A | 4/2011 | |
| JP | 2013-537538 A | 10/2013 | |
| JP | 2016-518109 A | 6/2016 | |
| JP | 2017-526723 A | 9/2017 | |
| JP | 2019-195331 A | 11/2019 | |
| WO | 2004/014954 A1 | 2/2004 | |
| WO | 2006/007529 A2 | 1/2006 | |
| WO | 2007/103572 A2 | 9/2007 | |
| WO | 2007/126386 A1 | 11/2007 | |
| WO | WO 2008/080989 A1 | 7/2008 | |
| WO | WO 2009050742 A1 | 4/2009 | |
| WO | 2009/092386 A2 | 7/2009 | |
| WO | WO 2009/087361 A1 | 7/2009 | |
| WO | WO2009105044 A1 † | 8/2009 | |
| WO | 2009/115561 A1 | 9/2009 | |
| WO | 2010/119256 A1 | 10/2010 | |
| WO | 2011/000551 A1 | 1/2011 | |
| WO | 2012/002760 A2 | 1/2012 | |
| WO | WO2012020307 A2 † | 2/2012 | |
| WO | 2012/108842 A1 | 8/2012 | |
| WO | 2012/110099 A1 | 8/2012 | |
| WO | 2012/110253 A2 | 8/2012 | |
| WO | 2012/126531 A1 | 9/2012 | |
| WO | 2012/135844 A2 | 10/2012 | |
| WO | 2012/169970 A1 | 12/2012 | |
| WO | WO 2013/014669 A1 | 1/2013 | |
| WO | WO 2013/014691 A1 | 1/2013 | |
| WO | 2013/022786 A2 | 2/2013 | |
| WO | WO 2017/122095 A1 | 7/2013 | |
| WO | WO2013188832 A1 † | 12/2013 | |
| WO | WO 2014/159662 A1 | 10/2014 | |
| WO | WO 2015/138878 A1 | 9/2015 | |
| WO | WO2016043654 A1 † | 3/2016 | |
| WO | WO 2016/172598 A1 | 10/2016 | |
| WO | WO 2016/196173 A1 | 12/2016 | |
| WO | WO 2017/123022 A1 | 7/2017 | |
| WO | WO 2019/060719 A1 | 3/2019 | |
| WO | WO 2019/231562 A1 | 12/2019 | |
| WO | WO 2012053976 A1 | 4/2020 | |

OTHER PUBLICATIONS

Bruno (Immunology Letters 168 (2015) 154-158), (Year: 2015).*

El-Darouti (Dermatologic Therapy, 20: 1-5, 2016). (Year: 2016).*

Katsuda et al. "The therapeutic potential of mesenchymal stem cell-derived extracellular vesicles" (Jan. 2013), Proteomics, vol. 13: 1637-1653. (Year: 2013).*

Gimona et al. (2017) "Manufacturing of Human Extracellular Vesicle-Based Therapeutics for Clinical Use," International Journal of Molecular Sciences, 18(6): 19 pages.

McBride et al. (2017) "Extracellular Vesicles as Biomarkers and Therapeutics in Dermatology: A Focus on Exosomes," Journal of Investigative Dermatology, 137(8): 1622-1629.

International Search Report and Written Opinion for International Application No. PCT/US2018/05223, mailing date Jan. 4, 2019.

U.S. Appl. No. 14/775,382 / 2016/0184363 / U.S. Pat. No. 10,500,231, filed Mar. 12, 2014 / Jun. 30, 2016 / Dec. 10, 2019, Evangelos V. Badiavas.

U.S. Appl. No. 16/668,851, filed Oct. 30, 2019, Evangelos V. Badiavas.

Ludwig et al., "Precipitation with polyethylene glycol followed by washing and pelleting by ultracentrifugation enriches extracellular vesicles from tissue culture supernatants in small and large scales," Journal of Extracellular Vesicles, Oct. 17, 2018, vol. 7, pp. 1-20.

Lasser et al., "Isolation and Characterization of RNA-Containing Exosomes", Journal of Visualized Experiments, Jan. 9, 2012, pp. 1-6.

Chen et al., "Cardiac progenitor-derived Exosomes protect ischemic myocardium from acute ischemia/reperfusion injury", Biochem Biophys Res Commun, Feb. 15, 2013, vol. 431, No. 3, pp. 566-571.

Extended European Search Report in European Patent Application No. 1921541.7, mailed Jun. 9, 2020, 15 pages.

Taylor et al., "Exosome Isolation for Proteomic Analyses and RNA Profiling", Methods in Molecular Biology, Feb. 2011, vol. 728, pp. 235-246.

Albarran Y Carvajal et al. (2007) "MVA E2 recombinant vaccine in the treatment of human papillomavirus infection in men presenting intraurethral flat condyloma: a phase I/II study," Biodrugs. 21(1):47-59.

Andreu et al. (Jun. 20, 2016) "Comparative Analysis of EV Isolation Procedures for miRNAs Detection in Serum Samples," J. Extracell. Vesicles. 5:31655.

Grenier et al. (1987) "Functional characterization of extracellular vesicles produced by Bacteroides gingivalis," Infection and Immunity. 55(1):111-117.

Merz et al. (2010) "Biochemical and Morphological Properties of Hepatitis C Virus Particles and Determination of Their Lipidome," J. Bol. Chem. 286(4):3018-3032.

Mori et al. (2008) "Human herpesvirus-6 induces MVB formation, and virus egress occurs by an exosomal release pathway," Traffic. 9:1728-1742.

Radhakrishnan et al. (2010) "Protein Analysis of Purified Respiratory Syncytial Virus Particles Reveals an Important Role for Heat Shock Protein 90 in Virus Particle Assembly," Mol. Cell. Proteomics. 9(9):1829-1848.

Raposo et al. (Feb. 18, 2013) "Extracellular vesicles: Exosomes, microvesicles, and friends," J. Cell. Biology. 4:373-383.

System Biosciences (2013) "User Manual: ExoQuick-TC(TM) Exosome Precipitation Solution," Catalog No. EXOTCxxA-1. System Biosciences (SBI). Accessible on the Internet at URL: https://www.systembio.com/downloads/Manual_ExoTC_WEB.pdf. [Last Accessed Jan. 19, 2017].

Venugopal et al. (2010) "Recalcitrant cutaneous warts treated with recombinant quadrivalent human papillomavirus vaccine (types 6, 11, 16, and 18) in a developmentally delayed, 31-year-old white man," Arch. Dermatol. 146(5):475-477.

Villa et al. (2006) "High sustained efficacy of a prophylactic quadrivalent human papillomavirus types 6/11/16/18 L1 virus-like particle vaccine through 5 years of follow-up," Br. J. Cancer. 95:1459-1466.

Zoller (2009) "Tetraspanins: push and pull in suppressing and promoting metastasis," Nat. Rev. Cancer. 9(1):40-55.

(56) References Cited

OTHER PUBLICATIONS

International Search Report with Written Opinion corresponding to International Patent Application No. PCT/JS2014/024629, mailed Jul. 3, 2014.
Bartholomew et al. (2009) "Mesenchymal stem cells in the induction of transplantation tolerance," Transplantation. 87:S55-7.
Breau et al. (2006) "Inadequate statistical power of negative clinical trials in urological literature," The Journal of Urology. 176:263-6.
Bruno et al. (Jun. 15, 2015) "The secretome of mesenchymal stromal cells: Role of extracellular vesicles in Immunomodulation," Immunology Letters. 168:154-8.
Chen et al. (Aug. 2016) "Immunomodulatory effects of mesenchymal stromal cells-derived exosome," Immunologic Research. 64:831-40.
El-Darouti et al. (Oct. 5, 2015) "Treatment of dystrophic epidermolysis bullosa with bone marrow non-hematopoeitic stem cells: a randomized controlled trial," Dermatol. Ther. 29:96-100.
Ichihara (2010) "An appraisal of statistical procedures used in derivation of reference intervals," Clinical Chemistry and Laboratory Medicine. 48:1537-51.
Haydek et al. (Aug. 10, 2017) "Validation and Banding of the ItchyQuant: A Self-Report Itch Severity Scale," J. Invest. Dermatol. 137:57-61.
Jones et al. (1995) "Immunodominant autoepitopes of type VII collagen are short, paired peptide sequences within the fibronectin type III homology region of the noncollagenous (NC1) domain," J. Invest. Dermatol. 104:231-5.
Lapiere et al. (1993) "Epitope mapping of type VII collagen. Identification of discrete peptide sequences recognized by sera from patients with acquired epidermolysis bullosa," J. Clin. Invest. 92:1831-9.
Li et al. (Apr. 27, 2016) "Exosome Derived From Human Umbilical Cord Mesenchymal Stem Cell Mediates MiR-181c Attenuating Burn-induced Excessive Inflammation," EBioMedicine. 8:72-82.
McBride et al. (Mar. 15, 2017) "Transgenic expression of a canonical Wnt inhibitor, kallistatin, is associated with decreased circulating CD19+ B lymphocytes in the peripheral blood," International Journal of Hematology. 105(6):748-757.
Palazzi et al. (2000) "Inherited dystrophic epidermolysis bullosa in inbred dogs: A spontaneous animal model for somatic gene therapy," J. Invest. Dermatol. 115:135-7.
Petrof et al. (Apr. 23, 2015) "Potential of Systemic Allogeneic Mesenchymal Stromal Cell Therapy for Children with Recessive Dystrophic Epidermolysis Bullosa," J. Invest. Dermatol. 135:2319-21.
Pfendner et al. (2001) "Epidermolysis bullosa carrier frequencies in the US population," J. Invest. Dermatol. 116:483-4.
Riazifar et al. (Oct. 28, 2016) "Stem Cell Extracellular Vesicles: Extended Messages of Regeneration," Annu. Rev. Pharmacol. Toxicol. 57:125-54.
Shabbir et al. (May 20, 2015) "Mesenchymal Stem Cell Exosomes Induce Proliferation and Migration of Normal and Chronic Wound Fibroblasts, and Enhance Angiogenesis In Vitro," Stem Cells Dev. 24(14):1635-47.
Siegel et al. (2009) "The immunosuppressive properties of mesenchymal stem cells," Transplantation. 87:S45-9.
South et al. (Jun. 2016) "Type VII Collagen Replacement Therapy in Recessive Dystrophic Epidermolysis Bullosa—How Much, How Often?" J. Invest. Dermatol. 136:1079-81.
Sundin et al. (2009) "HSCT recipients have specific tolerance to MSC but not to the MSC donor," J. Immunother. 32:755-64.
Wagner et al. (2010) "Bone Marrow Transplantation for Recessive Dystrophic Epidermolysis Bullosa," The New England Journal of Medicine. 363:629-39.
Woodley et al. (Jul. 10, 2017) "Gentamicin induces functional type VII collagen in recessive dystrophic epidermolysis bullosa patients," J. Clin. Invest. 127(8):3028-3038.
Woodley et al. (Nov. 8, 2013) "De novo anti-type VII collagen antibodies in patients with recessive dystrophic epidermolysis bullosa," J. Invest. Dermatol. 134:1138-40.

Japanese Patent Application No. 2016-501590, Official Action Summary dated Mar. 13, 2018, 1 page.
Japanese Patent Application No. 2016-501590, English Translation of the Office Action dated Mar. 13, 2018, 7 pp.
Vlassov et al., "Review, Exosomes: Current knowledge of their composition, biological functions, and diagnostic and therapeutic potentials", Biochemica et Biophysica Acta 1820, 2012, pp. 940-948.
U.S. Appl. No. 14/775,382 2016/0184363 U.S. Pat. No. 10,500,231, filed Sep. 11, 2015 Jun. 30, 2016 Dec. 10, 2019, Evangelos V. Badiavas.
U.S. Appl. No. 15/712,294 2018/0104186, filed Sep. 22, 2017 Apr. 19, 2018, Evangelos V. Badiavas.
U.S. Appl. No. 16/668,851 2020/0163999, filed Oct. 30, 2019 May 28, 2020, Evangelos V. Badiavas.
Kim et al., "Identification and characterization of stem cell secretome-based recombinant proteins for wound healing applications", Fromteirs in Bioengineering and Biotechnology, Jul. 22, 2022, 10.3389/fbioe.2022.954682.
Lee et al., "Exosomes and microvesicles: extracellular vesicles for genetic information transfer and gene therapy", Human Molecular Genetics, 2012, 21(1):R125-R134.
U.S. Appl. No. 14/775,382 2016/0184363 U.S. Pat. No. 10,500,231, filed Sep. 11, 2015 Jun. 30, 2016 Dec. 10, 2019, Evangelos V. Badiavas, Method for Isolation and Purification of Microvesicles from Cell Culture Supernatants and Biological Fluids.
U.S. Appl. No. 15/712,294 2018/0104186, filed Sep. 22, 2017 Apr. 19, 2018, Evangelos V. Badiavas, Methods and Compositions for the Treatment of Epidermolysis Bullosa.
U.S. Appl. No. 16/668,851 2020/0163999, filed Oct. 30, 2019 May 28, 2020, Evangelos V. Badiavas, Method for Isolation and Purification of Microvesicles from Cell Culture Supernatants and Biological Fluids.
U.S. Appl. No. 18/332,063, filed Jun. 9, 2023, Evangelos V. Badiavas, Method for Isolation and Purification of Microvesicles From Cell Culture Supernatants and Biological Fluids.
[1P1013] (EV), EV(Extracellular vesicles), exosome, Abstracts of the Annual Meeting of the Japanese Biochemical Society and the Annual Meeting of the Molecular Biology Society of Japan, 2015, 88th.
BioCat GmbH, "Exosome Isolation", published online Aug. 20, 2011, retrieved from url: https://www.biocat.com/cell-biology/exosomes/exosome-isolation.
Bray et al., "Extracellular Vesicles as Therapeutic Tools for the Treatment of Chronic Wounds", Pharmaceutics, 2021, 13(1543):1-25.
Chen et al., "Paracrine Factors of Mesenchymal Stem Cells Recruit Macrophages and Endothelial Lineage Cells and Enhance Wound Healing", PLoS One, Feb. 2008, 3(4): e1886.
Heo et al., "Tumor Necrosis Factor-α-Activated Human Adipose Tissue-Derived Mesenchymal Stem Cells Accelerate Cutaneous Wound Healing through Paracrine Mechanisms", Journal of Investigative Dermatology, Jul. 2011, 131(7): 1559-1567.
Lai et al., "Exosome secreted by MSC reduces myocardial ischemia/reperfusion injury", Stem Cell Research, May 2010, 4(3): 214-222.
Lai et al., "Mesenchymal stem cell exosomes", Seminars in Cell & Developmental Biology, Apr. 2015, 40: 828-88.
Lee et al., "Exosomes mediate the cytoprotective action of mesenchymal stromal cells on hypoxia-induced pulmonary hypertension", Circulation, Nov. 27, 2012, 126(22): 2601-2611.
Vishnubhatla et al., "The Development of Stem Cell-derived Exosomes as a Cell-free Regenerative Medicine", J Circ Biomark., 2014, 3(2): 1-14.
Yew et al., "Enhancement of Wound Healing by Human Multipotent Stromal Cell Conditioned Medium: The Paracrine Factors and p38 MAPK Activation", Cell Transplantation, 2011, 20: 693-706.
Extended European Search Report for European Patent Application No. 18859166.3, mailed May 6, 2021, 8 pages.
Extended European Search Report received for European Patent Application No. 14774189.6, mailed on Aug. 4, 2016.

(56)  References Cited

OTHER PUBLICATIONS

Ha et al., "Exosomes as Therapeutic Drug Carriers and Delivery Vehicles Across Biological Membranes: Current Perspectives and Future Challenges", Acta Pharmaceutica Sinica B, 2016, 6(4): 287-296.

International Preliminary Report on Patentability for PCT International Patent Application No. PCT/US2018/052213, dated Mar. 24, 2020, 9 pages.

Katsuda et al. "The therapeutic potential of mesenchymal stem cell-derived extracellular vesicles", Jan. 2013, Proteomics, 13(10-11): 1637-1653.

Sun et al., "Exosomes Are Endogenous Nanoparticles that can deliver biological information between cells", Advanced Drug Delivery Reviews, 2013, 65: 342-347.

System Biosciences Exoquick-TC Exosome Precipitation Solution, 2011, pp. 1-10.

Vlassov et al., "Review, Exosomes: Current knowledge of their composition, biological functions, and diagnostic and therapeutic potentials", Biochemica et Biophysica Acta (BBA), 2012, 1820(7): 940-948.

Collino et al., "Exosome and Microvesicle-Enriched Fractions Isolated from Mesenchymal Stem Cells by Gradient Separation Showed Different Molecular Signatures and Functions on Renal Tubular Epithelial Cells", Stem Cell Rev. Rep., Apr. 2017, 13(2): 226-243.

Colombo et al., "Biogenesis, secretion, and intercellular interactions of exosomes and other extracellular vesicles", Annu. Rev. Cell Dev. Biol., 2014, 30: 255-289. Epub Aug. 21, 2014.

Han et al., "Apoptotic extracellular vesicles: mechanisms, applications, and therapeutic potential", Med-X, Dec. 16, 2024, 2: 27.

Ma et al., "Apoptotic extracellular vesicles are metabolized regulators nurturing the skin and hair", Bioactive Mater., May 11, 2022, 19: 626-641. eCollection Jan. 2023.

McBride et al., "Bone Marrow Mesenchymal Stem Cell-Derived CD63+ Exosomes Transport Wnt3a Exteriorly and Enhance Dermal Fibroblast Proliferation, Migration, and Angiogenesis In Vitro", Stem Cells Dev., Oct. 1, 2017, 26(19): 1384-1398. Epub Aug. 14, 2017.

Papait et al., "Comparison of EV-free fraction, EVs, and total secretome of amniotic mesenchymal stromal cells for their immunomodulatory potential: a translational perspective", Frontiers in Immunology, Aug. 16, 2022, 13: 960909.

Wolf et al., "A functional corona around extracellular vesicles enhances angiogenesis, skin regeneration and immunomodulation", J. Extracell. Vesicles, Apr. 2022, 11(4): e12207.

Zhou et al., "Apoptotic bodies for advanced drug delivery and therapy", J. Controlled Release, Nov. 2022, 351: 394-406. Epub Sep. 27, 2022.

L Chen et al., Cardiac progenitor-derived Exosomes protect ischemic myocardium from acute ischemia/reperfusion injury, Biochem. Biophys. Res. Commun., 431(3):566-71, (Feb. 15, 2013).†

\* cited by examiner

† cited by third party

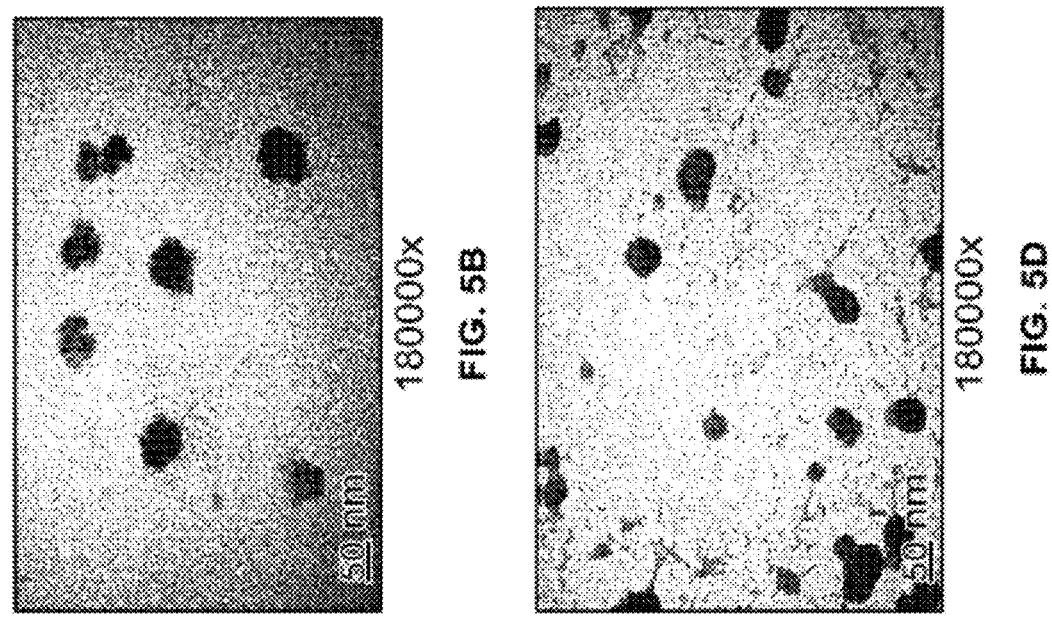
180000x
FIG. 5B
180000x
FIG. 5D
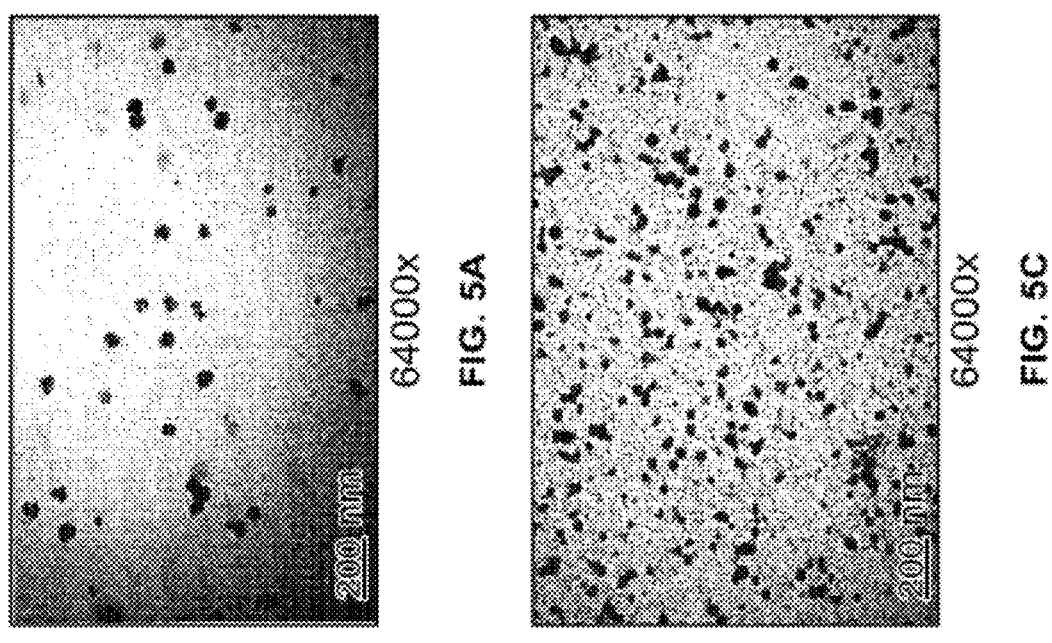
64000x
FIG. 5A
64000x
FIG. 5C

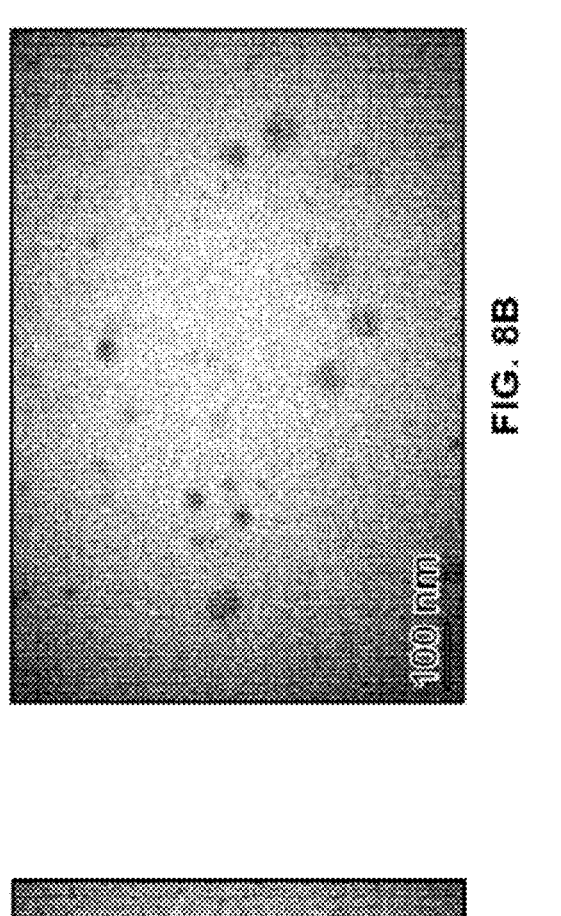
FIG. 8B
FIG. 8C
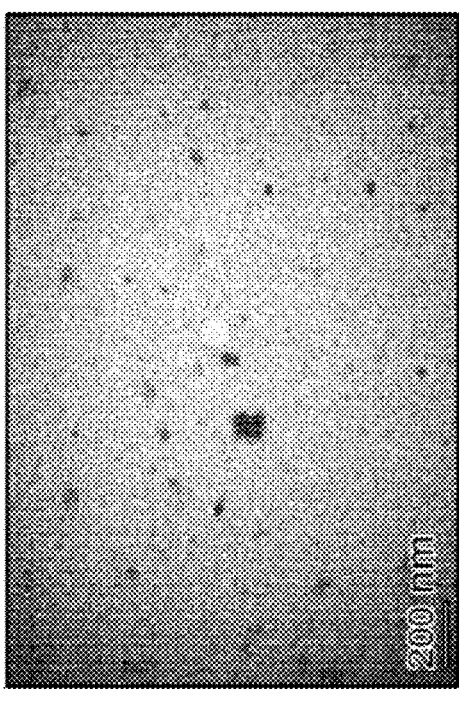
FIG. 8A

3 Days Post Treatment

PEG Precipitation MV 1 ug/ml

Ultracentrifuge MV 1 ug/ml

PBS

PEG Precipitation MV 10 ug/ml

Ultracentrifuge MV 10 ug/ml

Depleted

Pretreatment

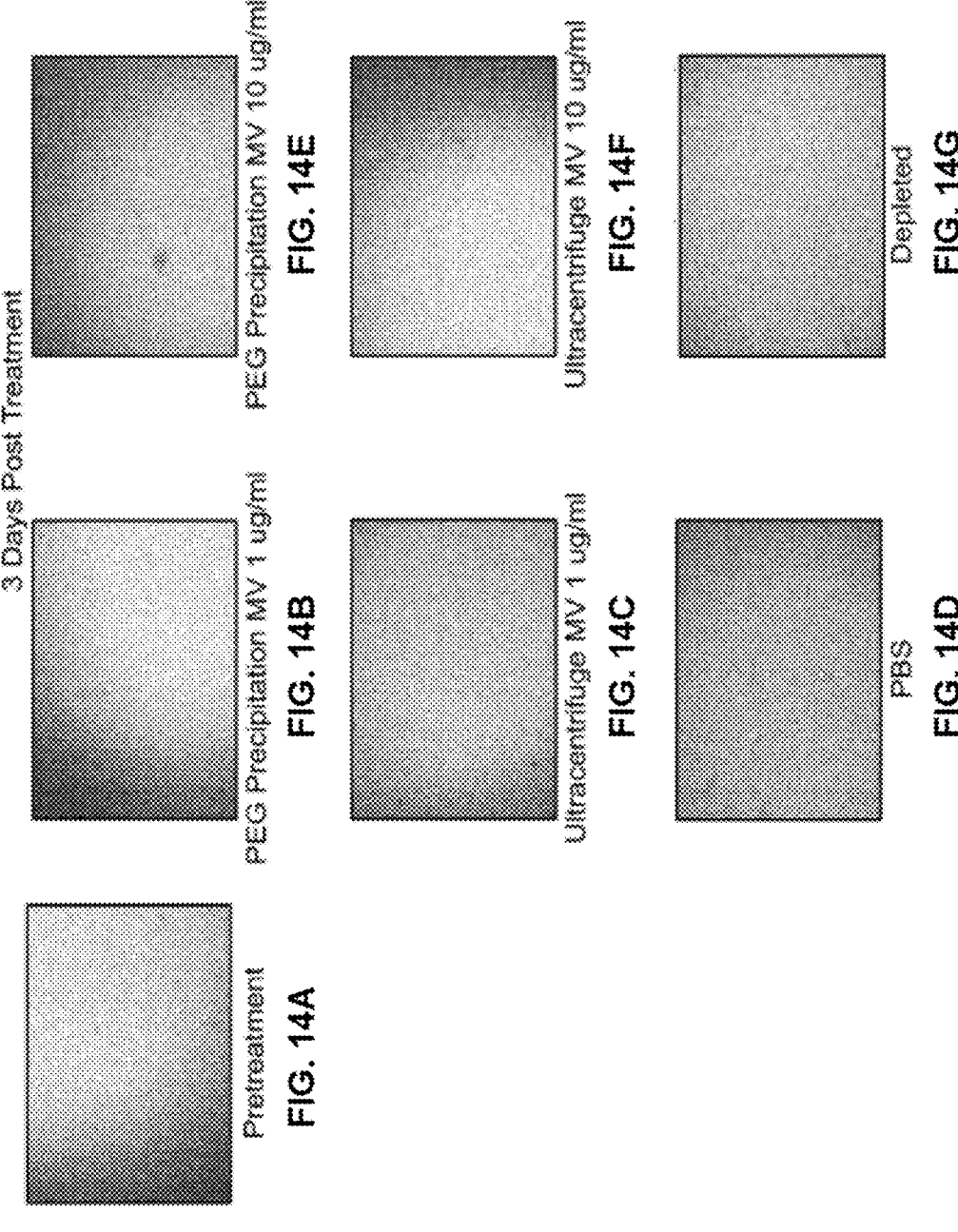

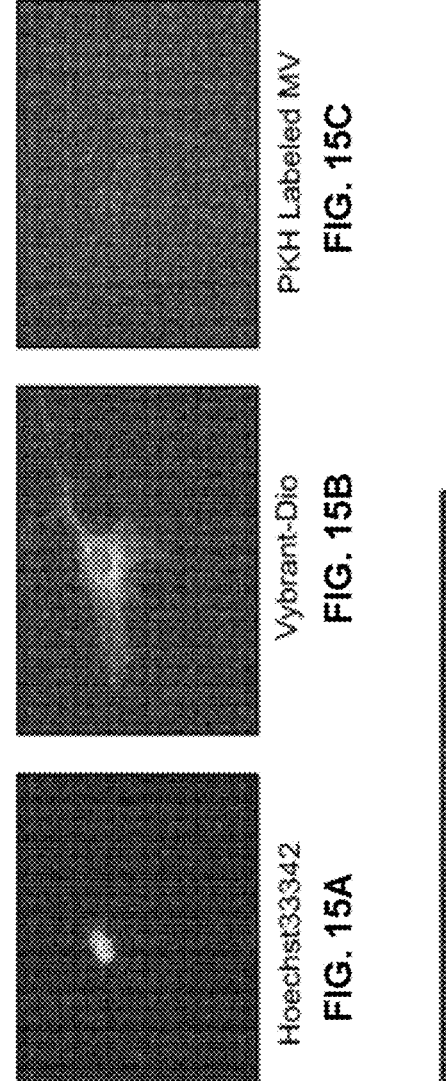
Hoechst33342
FIG. 15A
Vybrant-Dio
FIG. 15B
PKH Labeled MV
FIG. 15C
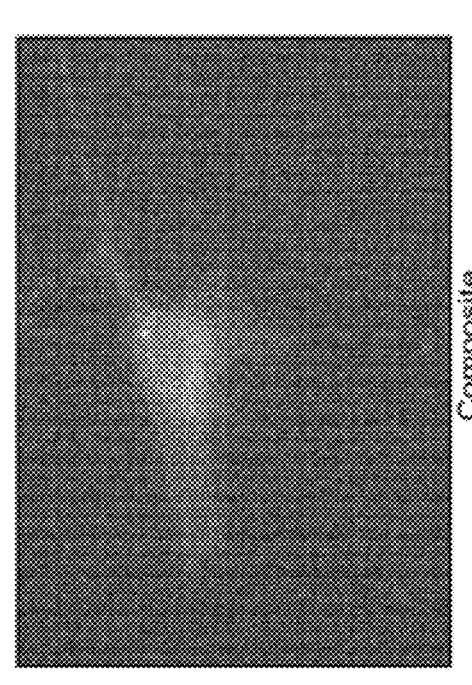
Composite
FIG. 15D

Hoechst33342

Vybrant-Dio

PKH Labeled MV

Composite

PBS hMSC Conditioned medium depleted of MV hMSC MV ultracentrifugation hMSC MV PEG precipitation Human Plasma MV PEG Precipitation Phospho-STAT3 Tyr705

SK-MEL28 Cell Lysate

SK-MEL28 MV Lysate

BRAF V600E

Hoechst33342

Vybrant-Dio

GFP

Composite

Hoechst33342

Vybrant-Dio

MV Derived from
GFP Expressing MSC

Composite

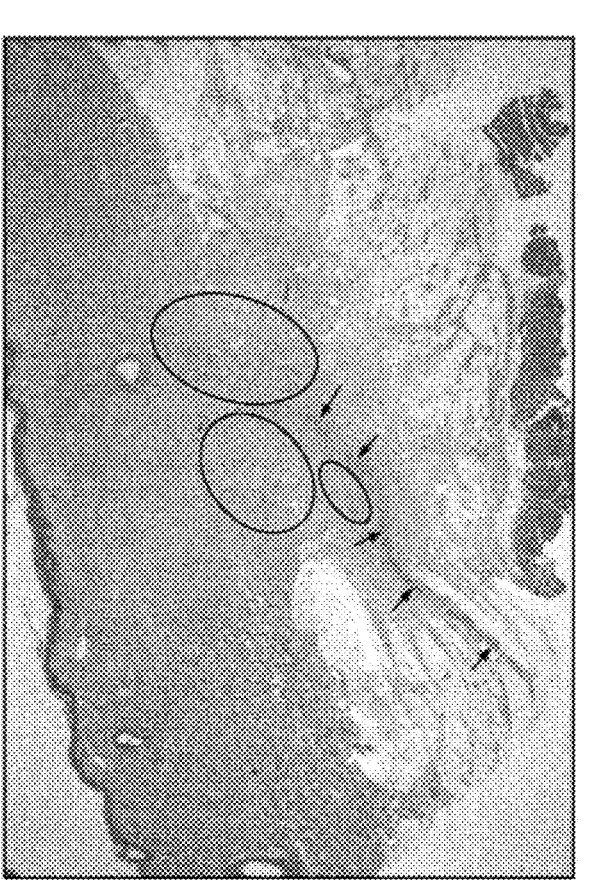

Figure 5. Full Thickness Wound Treated with MV's Prepared by Our Methods at Day 28 (12.5X)
Arrows Illustrate New Nerve Growth into a Remodeling Wound.
Nerve Growth is Associated with Angiogenesis.- Highlighted in the Circled Areas
These Findings are Highly Indicative of Tissue Regeneration
This has Never been Observed
Not Observed in Controls or Ultracentrifuged MV Treated Wounds

FIG. 26

FSC-H

Positive Control: GFP

FSC-H

Experiment 1

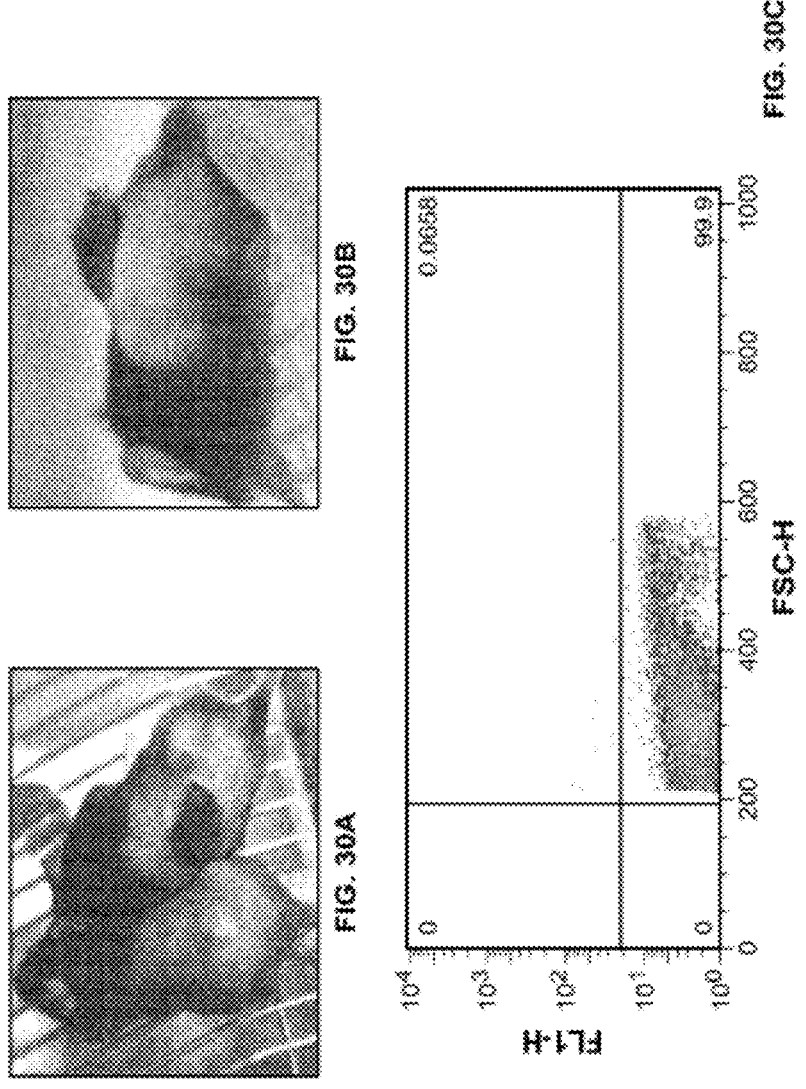

Example Images

Bone Marrow Aspirate MV

Vehicle Control

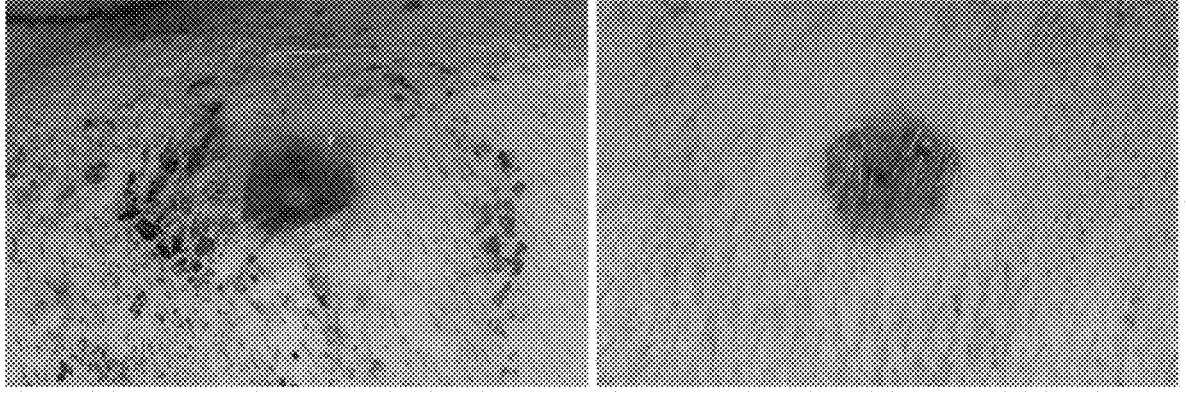
FIG. 40A                    FIG. 40B

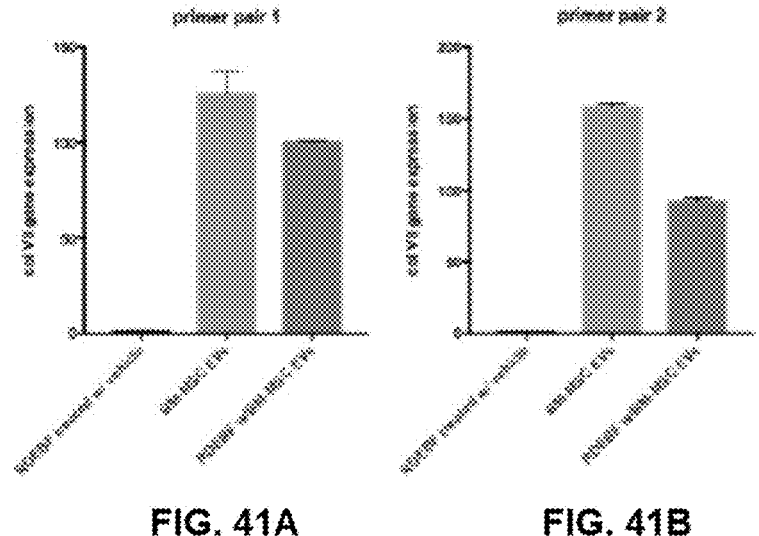
FIG. 41A                    FIG. 41B

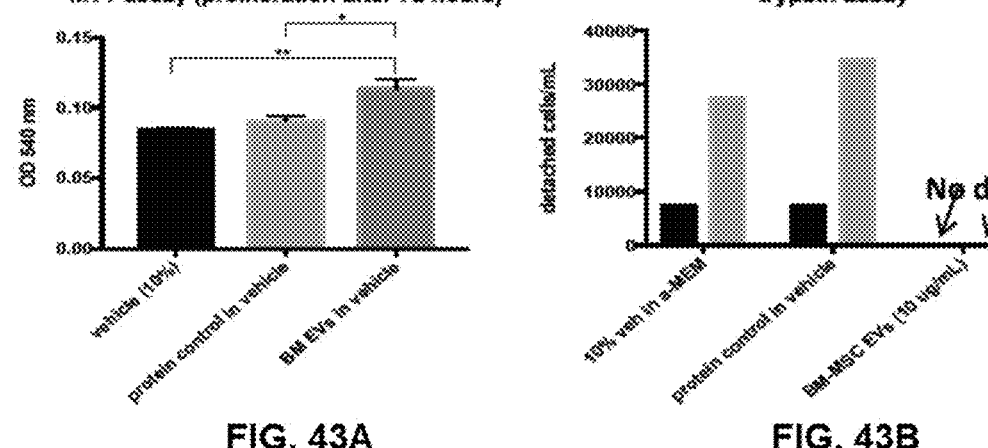
FIG. 43A                            FIG. 43B

COL7A1 (cDNA)
collagen VII (COL7A1) expression
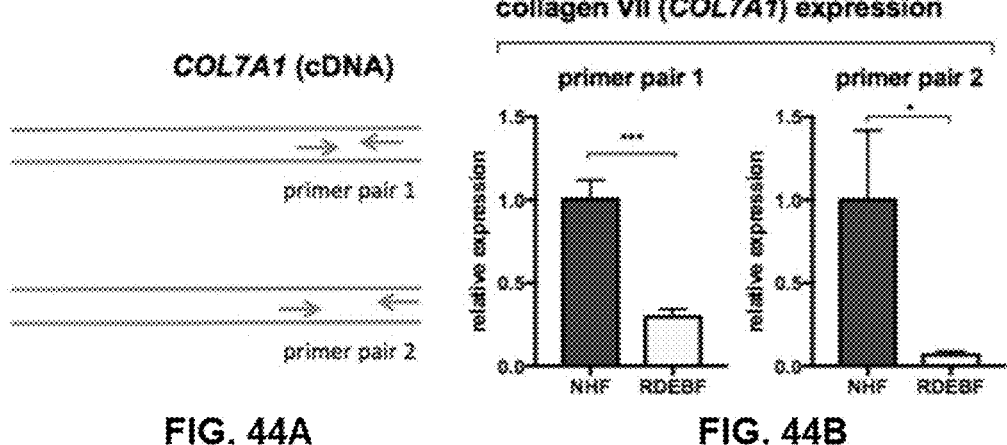
primer pair 1
primer pair 2
FIG. 44A
FIG. 44B
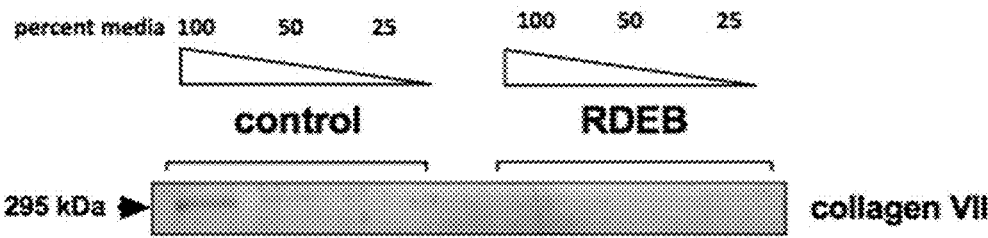
FIG. 44C day 0     day 1     day 3              day 6 treat     wash               collect media

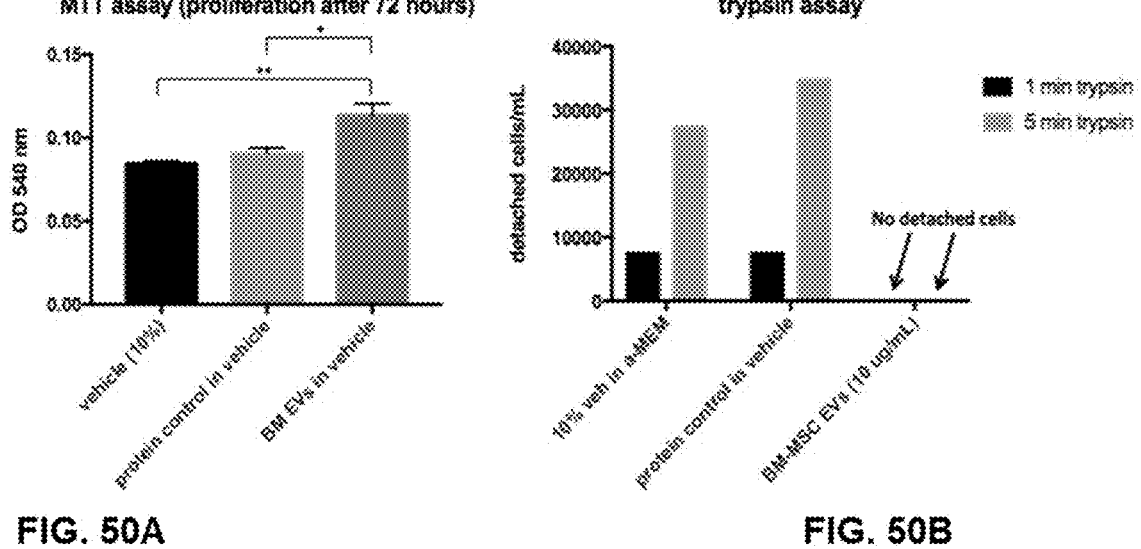
FIG. 50A                    FIG. 50B

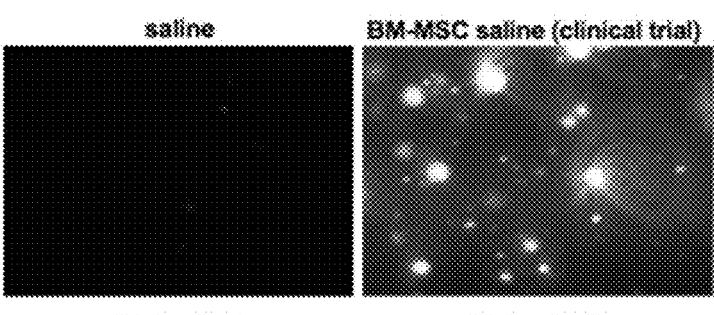
FIG. 51A                    FIG. 51B
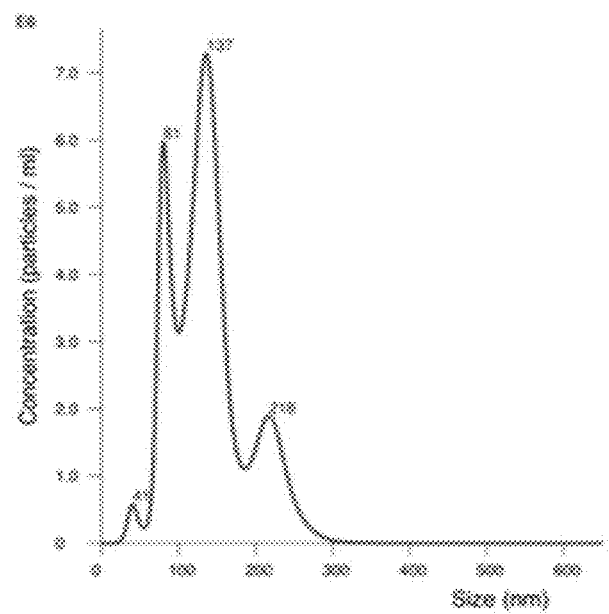
FIG. 51C
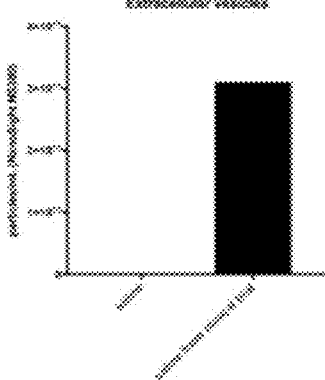
FIG. 51D
FIG. 51E

METHODS AND COMPOSITIONS FOR THE TREATMENT OF EPIDERMOLYSIS BULLOSA

RELATED APPLICATIONS

This application is a continuation-in-part of U.S. Ser. No. 14/775,382, filed Sep. 11, 2015, which is a 371 application of PCT/US14/24629, filed Mar. 12, 2014, which claims priority to U.S. Provisional Patent Application No. 61/778,591, filed Mar. 13, 2013. The entire contents of these applications are herein incorporated by reference.

FIELD OF THE INVENTION

The present invention relates to the fields of medicine, cell biology, molecular biology and genetics. In particular, the present invention relates to compositions and methods for treating epidermolysis bullosa.

BACKGROUND

Epidermolysis bullosa (EB) is a group of genodermatoses that cause blisters in the skin and mucosal membranes, with an incidence of 20 per million newborns in the United States. It is a result of a defect in anchoring between the epidermis and dermis, resulting in skin fragility. Its severity ranges from mild to lethal.

Dystrophic epidermolysis bullosa (DEB) is an inherited variant affecting the skin and other organs. Children born with this disease are referred to as "butterfly children" as their skin is described to be as delicate and fragile as a butterfly's wings. The skin of DEB patients is highly susceptible to severe blistering. Open wounds on the skin heal slowly or not at all, often scarring extensively, and are particularly susceptible to infection. Many individuals bathe in a bleach and water mixture to fight off these infections. The chronic inflammation leads to errors in the DNA of the affected skin cells, which in turn causes squamous cell carcinoma (SCC). The majority of DEB patients die before the age of 30, either of SCC or complications related to DEB.

DEB is caused by mutations within the human COL7A1 gene encoding the protein type VII collagen (collagen VII). DEB-causing mutations can be either autosomal dominant (DDEB) or autosomal recessive (RDEB). COL7A1 is located on the short arm of human chromosome 3, in the chromosomal region denoted 3p21.31. The gene is approximately 31,000 base pairs in size and is remarkable for the extreme fragmentation of its coding sequence into 118 exons. COL7A1 is transcribed into an mRNA of 9,287 base pairs. In the skin, the type VII collagen protein is synthesized by keratinocytes and dermal fibroblasts.

Collagen VII is a 300 kDa protein that dimerizes to form a semicircular looping structure: the anchoring fibril. Anchoring fibrils are thought to form a structural link between the epidermal basement membrane and the fibrillar collagens in the upper dermis. Collagen VII is also associated with the epithelium of the esophageal lining, and DEB patients may suffer from chronic scarring, webbing, and obstruction of the esophagus. Affected individuals are often severely malnourished due to trauma to the oral and esophageal mucosa and require feeding tubes for nutrition. They also suffer from iron-deficiency anemia of uncertain origin, which leads to chronic fatigue.

There remains a need to provide methods and compositions to treat EB.

SUMMARY

The present invention provides methods to isolate microvesicles (MVs), e.g., extracellular vesicles (MVs) from biological fluids without damaging the structural and/or functional integrity of the microvesicles. The present invention also provides methods to isolate ectosomes, microparticles, microvesicles, nanovesicles, shedding vesicles, apoptotic bodies, or membrane particles from biological fluids without damaging their structural and/or functional integrity. The present invention further provides MVs (e.g., EVs) and methods of using MVs (e.g., EVs) for the treatment of EB (e.g., RDEB and/or DDEB).

In one aspect, a method of treating epidermolysis bullosa in a subject in need thereof comprising administering a pharmaceutical composition comprising isolated microvesicles purified by precipitation from a biological fluid to the subject, and alleviating or reducing one or more symptoms of epidermolysis bullosa in the subject is provided.

In certain exemplary embodiments, the isolated microvesicles are extracellular vesicles that are optionally precipitated from a biological fluid using a precipitating agent selected from the group consisting of calcium ions, magnesium ions, sodium ions, ammonium ions, iron ions, ammonium sulfate, alginate, and polyethylene glycol.

In certain exemplary embodiments, the biological fluid is from mammalian (e.g., human) cells.

In certain exemplary embodiments, the precipitating agent is polyethylene glycol, that optionally has a molecular weight of about 6,000 Da, about 8,000 Da, about 10,000 Da or about 20,000 Da.

In certain exemplary embodiments, the one or more symptoms of epidermolysis bullosa are selected from the group consisting of any combination of thickened calluses, epidermal blistering (e.g., of the hands, the feet, the elbows and/or the knees), blistering of oral mucosa, thickened fingernails and/or toenails, sepsis, malnutrition, dehydration, electrolyte imbalance, obstructive airway complications, defective collagen VII expression, anemia, esophageal strictures, growth retardation, webbing or fusion of fingers and/or toes, malformation of teeth, microstomia and corneal abrasions.

In certain exemplary embodiments, treatment comprises increasing collagen VII expression in the subject.

In another aspect, a method of treating epidermolysis bullosa in a subject in need thereof comprising administering a pharmaceutical composition comprising isolated extracellular vesicles to the subject and alleviating or reducing one or more symptoms of epidermolysis bullosa in the subject is provided.

In certain exemplary embodiments, the isolated microvesicles are extracellular vesicles that are optionally precipitated from a biological fluid using a precipitating agent selected from the group consisting of calcium ions, magnesium ions, sodium ions, ammonium ions, iron ions, ammonium sulfate, alginate, and polyethylene glycol.

In certain exemplary embodiments, the biological fluid is from mammalian (e.g., human) cells.

In certain exemplary embodiments, the precipitating agent is polyethylene glycol, that optionally has a molecular weight of about 6,000 Da, about 8,000 Da, about 10,000 Da or about 20,000 Da.

In certain exemplary embodiments, the one or more symptoms of epidermolysis bullosa are selected from the group consisting of any combination of thickened calluses, epidermal blistering (e.g., of the hands, the feet, the elbows and/or the knees), blistering of oral mucosa, thickened fingernails and/or toenails, sepsis, malnutrition, dehydration, electrolyte imbalance, obstructive airway complications, defective collagen VII expression, anemia, esophageal strictures, growth retardation, webbing or fusion of fingers and/or toes, malformation of teeth, microstomia and corneal abrasions.

In certain exemplary embodiments, treatment comprises increasing collagen VII expression in the subject.

In another aspect, a method of increasing collagen VII levels in a cell, comprising contacting the cell with an isolated extracellular vesicle from a mammalian fluid, wherein the cell expresses an epidermolysis bullosa genotype, is provided.

In certain exemplary embodiments, the cell comprises a mutation in the COL7A1 gene.

In certain exemplary embodiments, the isolated extracellular vesicle delivers collagen VII protein and/or COL7A1 mRNA to the cell In another aspect, a method of delivering one or more bioactive agents to a cell, comprising contacting the cell with an isolated extracellular vesicle from a mammalian fluid is provided.

In certain exemplary embodiments, the cell comprises a mutation in the COL7A1 gene.

In certain exemplary embodiments, the one or more bioactive agents are selected from the group consisting of collagen VII protein, collagen VII mRNA, a STAT3 signalling activator (e.g., an interferon, epidermal growth factor, interleukin-5, interleukin-6, a MAP kinase, and/or a c-src non-receptor tyrosine kinase), and a canonical Wnt activator.

In certain exemplary embodiments, STAT3 is phosphorylated.

In certain exemplary embodiments, the one or more bioactive agents are one or more pharmaceutical compounds.

In one embodiment, the present invention provides a method for isolating and/or purifying microvesicles from cell culture supernatants or biological fluids utilizing precipitation agent that precipitates the microvesicle from the cell culture supernatant or biological fluid by displacing the water of solvation.

In one embodiment, the present invention provides an isolated preparation of microvesicles. In one embodiment, the isolated preparation of microvesicles is subsequently purified. In one embodiment, the isolated preparation of microvesicles is subsequently purified to yield a preparation of ectosomes. In one embodiment, the isolated preparation of microvesicles is subsequently purified to yield a preparation of microparticles. In one embodiment, the isolated preparation of microvesicles is subsequently purified to yield a preparation of nanovesicles. In one embodiment, the isolated preparation of microvesicles is subsequently purified to yield a preparation of shedding vesicles. In one embodiment, the isolated preparation of microvesicles is subsequently purified to yield a preparation of membrane particles. In one embodiment, the isolated preparation of microvesicles is subsequently purified to yield a preparation of apoptotic bodies.

In one embodiment, the present invention provides an isolated preparation of microvesicles that promotes or enhances angiogenesis. In one embodiment, the isolated preparation of microvesicles promotes or enhances angiogenesis in a patient.

In one embodiment, the present invention provides an isolated preparation of microvesicles that promotes or enhances neuronal regeneration. In one embodiment, the isolated preparation of microvesicles promotes or enhances neuronal regeneration in a patient.

In one embodiment, the present invention provides an isolated preparation of microvesicles that promotes or enhances cellular proliferation. In one embodiment, the isolated preparation of microvesicles promotes or enhances cellular proliferation in a patient.

In one embodiment, the present invention provides an isolated preparation of microvesicles that promotes or enhances cellular migration. In one embodiment, the isolated preparation of microvesicles promotes or enhances cellular migration in a patient. In one embodiment, the present invention provides an isolated preparation of microvesicles that promotes or enhances wound healing. In one embodiment, the wound is a full-thickness burn. In one embodiment, the wound is a second-degree burn.

In one embodiment, the present invention provides an isolated preparation of microvesicles that reduces scar formation in a patient.

In one embodiment, the present invention provides an isolated preparation of microvesicles that reduces wrinkle formation in the skin of a patient.

In one embodiment, the present invention provides an isolated preparation of microvesicles that is used to diagnose the presence and/or progression of a disease in a patient. In one embodiment, the disease is metastatic melanoma. In an alternative embodiment the disease in an inflammatory/ autoimmune disorder such as rheumatoid arthritis. In one embodiment, the disease is graft versus host disease.

In one embodiment, the present invention provides an isolated preparation of microvesicles that can promote functional regeneration and organization of complex tissue structures. In one embodiment the present invention provides an isolated preparation of microvesicles that can regenerate hematopoietic tissue in a patient with aplastic anemia. In one embodiment the present invention provides an isolated preparation of microvesicles that can regenerate at least one tissue in a patient with diseased, damaged or missing skin selected from the group consisting of: epithelial tissue, stromal tissue, nerve tissue, vascular tissue and adnexal structures. In one embodiment, the present invention provides an isolated preparation of microvesicles that can regenerate tissue and/or cells from all three germ layers.

In one embodiment, the present invention provides an isolated preparation of microvesicles that is used to modulate the immune system of a patient.

In one embodiment, the present invention provides an isolated preparation of microvesicles that enhances the survival of tissue or cells that is transplanted into a patient. In one embodiment, the patient is treated with the isolated preparation of microvesicles prior to receiving the transplanted tissue or cells. In an alternate embodiment, the patient is treated with the isolated preparation of microvesicles after receiving the transplanted tissue or cells. In an alternate embodiment, the tissue or cells is treated with the isolated preparation of microvesicles. In one embodiment, the tissue or cells is treated with the isolated preparation of microvesicles prior to transplantation.

In one embodiment, the present invention provides an isolated preparation of microvesicles containing at least one molecule selected from the group consisting of RNA, DNA, and protein from a host cell. In one embodiment, the host cell is engineered to express at least one molecule selected from the group consisting of RNA, DNA, and protein. In one embodiment, the isolated preparation of microvesicles containing at least one molecule selected from the group consisting of RNA, DNA, and protein from a host cell is used as a therapeutic agent.

BRIEF DESCRIPTION OF THE DRAWINGS

The accompanying drawings, which are incorporated herein and form part of the specification, illustrate various embodiments of the present invention and, together with the description, further serve to explain the principles of the invention and to enable a person of ordinary skill in the art to make and use the invention. In the drawings, like reference numbers indicate identical or functionally similar elements. A more complete appreciation of the invention and many of the attendant advantages thereof will be readily obtained as the same becomes better understood by reference to the following detailed description when considered in connection with the accompanying drawings, wherein:

FIG. 5A-FIG. 5D show electron micrographs of microvesicles derived from medium conditioned using human bone marrow-derived mesenchymal stem cells isolated by the ultracentrifuge method described in Example 1 (FIG. 5A & FIG. 5B) and isolated according to the methods of the present invention (FIG. 5C & FIG. 5D) at the magnifications shown in the panels.

FIG. 8A-FIG. 8C show electron micrographs of microvesicles isolated from human plasma according to the methods of the present invention. FIG. 8A through FIG. 8C show the microvesicles under increasing magnification, as shown by the scale bars in the panels.

FIG. 9A through FIG. 9C show the microvesicles under increasing magnification, as shown by the scale bars in the panels.

FIG. 10A through FIG. 10C show the microvesicles under increasing magnification, as shown by the scale bars in the panels.

FIG. 13B and FIG. 13E) and microvesicles isolated by ultracentrifugation (Ultracentrifuge; FIG. 13C and FIG. 13F) at the concentrations shown. Fibroblasts treated with PBS or microvesicle depleted culture medium were included as a control (FIG. 13D and FIG. 13G).

FIG. 14A-FIG. 14G shows the effect of microvesicles isolated from medium conditioned using human bone marrow-derived mesenchymal stem cells on the migration of human dermal fibroblasts obtained from a diabetic foot ulcer, as determined by the ability of the fibroblasts to migrate into a region that had been scratched off. The panel labeled "pretreatment" shows a representative area of a cell culture plate where the cells were removed, prior to the addition of the test treatments (FIG. 14A). The effect of fibroblast migration was tested using microvesicles isolated according to the methods of the present invention (PEG precipitation; FIG. 14B and FIG. 14E) and microvesicles isolated by ultracentrifugation (Ultracentrifuge; FIG. 14C and FIG. 14F) at the concentrations shown. Fibroblasts treated with PBS or microvesicle depleted culture medium were included as a control (FIG. 14D and FIG. 14G).

FIG. 15A-FIG. 15D shows the uptake of the microvesicles of the present invention into human dermal fibroblasts. Cell nuclei, resolved using Hoechst 33342 dye are shown in the panel labeled "Hoechst33342" (FIG. 15A). Cells, resolved using vybrant dye are shown in the panel labeled "Vybrant-Dio" (FIG. 15B). Microvesicles, resolved using PKH dye are shown in the panel labeled "PKH labeled MV" (FIG. 15C). A panel where images obtained from all three dyes are overlaid is seen in the panel labeled "Composite" (FIG. 15D).

Figures 16A, 16B, 16C, 16D:
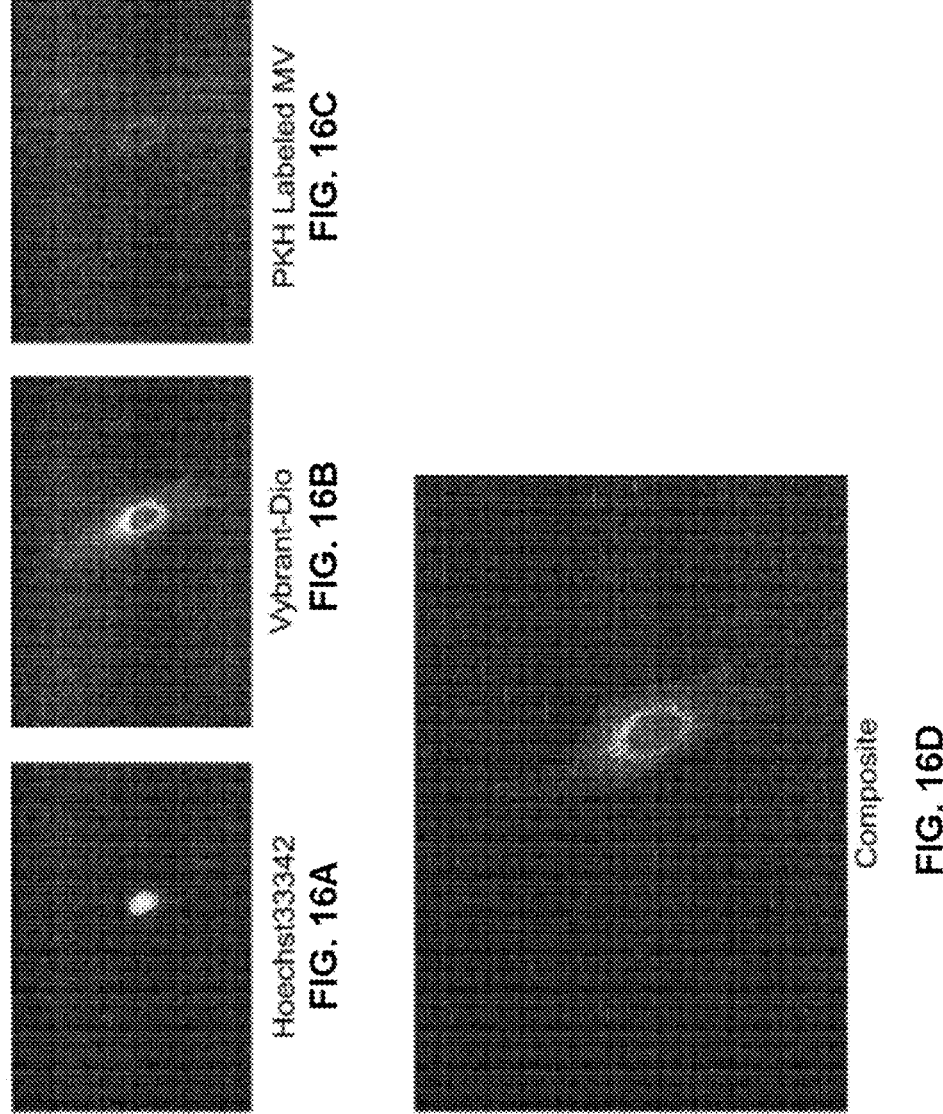
FIG. 16A-FIG. 16D shows the uptake of the microvesicles of the present invention into human dermal fibroblasts. Cell nuclei, resolved using Hoechst 33342 dye are shown in the panel labeled "Hoechst33342" (FIG. 16A).

Cells, resolved using vybrant dye are shown in the panel labeled "Vybrant-Dio" (FIG. 16B). Microvesicles, resolved using PKH dye are shown in the panel labeled "PKH labeled MV" (FIG. 16C). A panel where images obtained from all three dyes are overlaid is seen in the panel labeled "Composite" (FIG. 16D).

Figure 17:
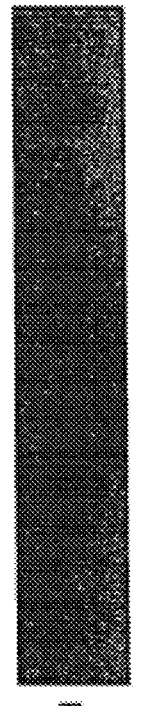

FIG. 17 shows a Western blot of lysates of human dermal fibroblasts treated with: microvesicles isolated according to the methods of the present invention from plasma obtained from a patient suffering from rheumatoid arthritis (Human Plasma MV PEG Precipitation); microvesicles isolated according to the methods of the present invention from medium conditioned with bone marrow-derived mesenchymal stem cells (Human hMSC MV PEG Precipitation); microvesicles isolated via ultracentrifugation from medium conditioned with bone marrow-derived mesenchymal stem cells (Human hMSC MV ultracentrifugation); PBS control; and a depleted medium control (hMSC conditioned medium depleted of MV).

Figure 18:
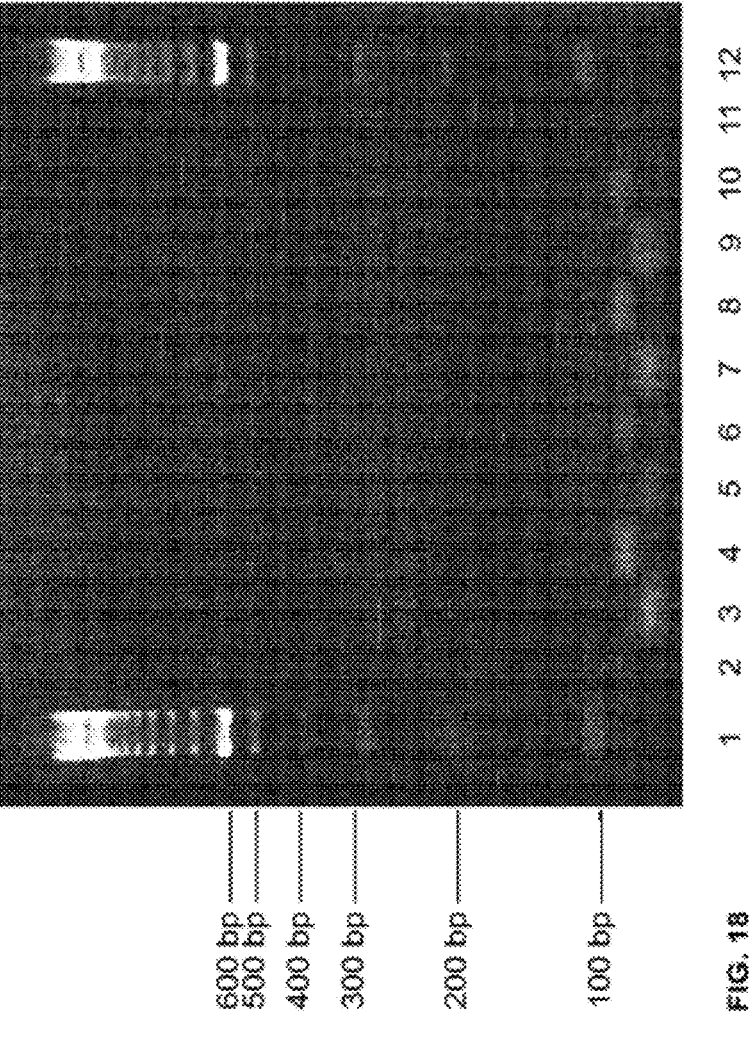

FIG. 18 shows the presence of the region containing exon 15 of BRAF containing the T1799A mutation, in: SK-MEL28 cells, from RNA amplified using primer 1 (lane 3); SK-MEL28 cells, from RNA amplified using primer 2 (lane 4); microvesicles isolated according to the methods of the present invention from medium conditioned with SK-MEL28 cells, from RNA amplified using primer 1 (lane 5); microvesicles isolated according to the methods of the present invention from medium conditioned with SK-MEL28 cells, from RNA amplified using primer 2 (lane 6); SK-MEL28 cells, from DNA amplified using primer 1 (lane 7); SK-MEL28 cells, from DNA amplified using primer 2 (lane 8); microvesicles isolated according to the methods of the present invention from medium conditioned with SK-MEL28 cells, from DNA amplified using primer 1 (lane 9); and microvesicles isolated according to the methods of the present invention from medium conditioned with SK-MEL28 cells, from DNA amplified using primer 2 (lane 10).

Figure 19:
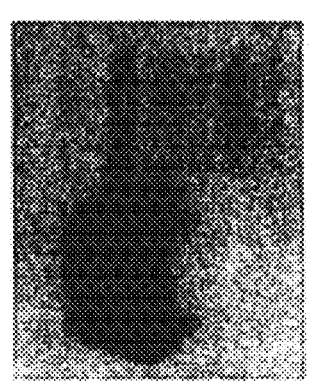

FIG. 19 shows the presence of V600E BRAF in a lysate of SK-MEL28 cells and a lysate of microvesicles isolated according to the methods of the present invention from medium conditioned with SK-MEL28 cells.

Figures 20A, 20B, 20C, 20D:
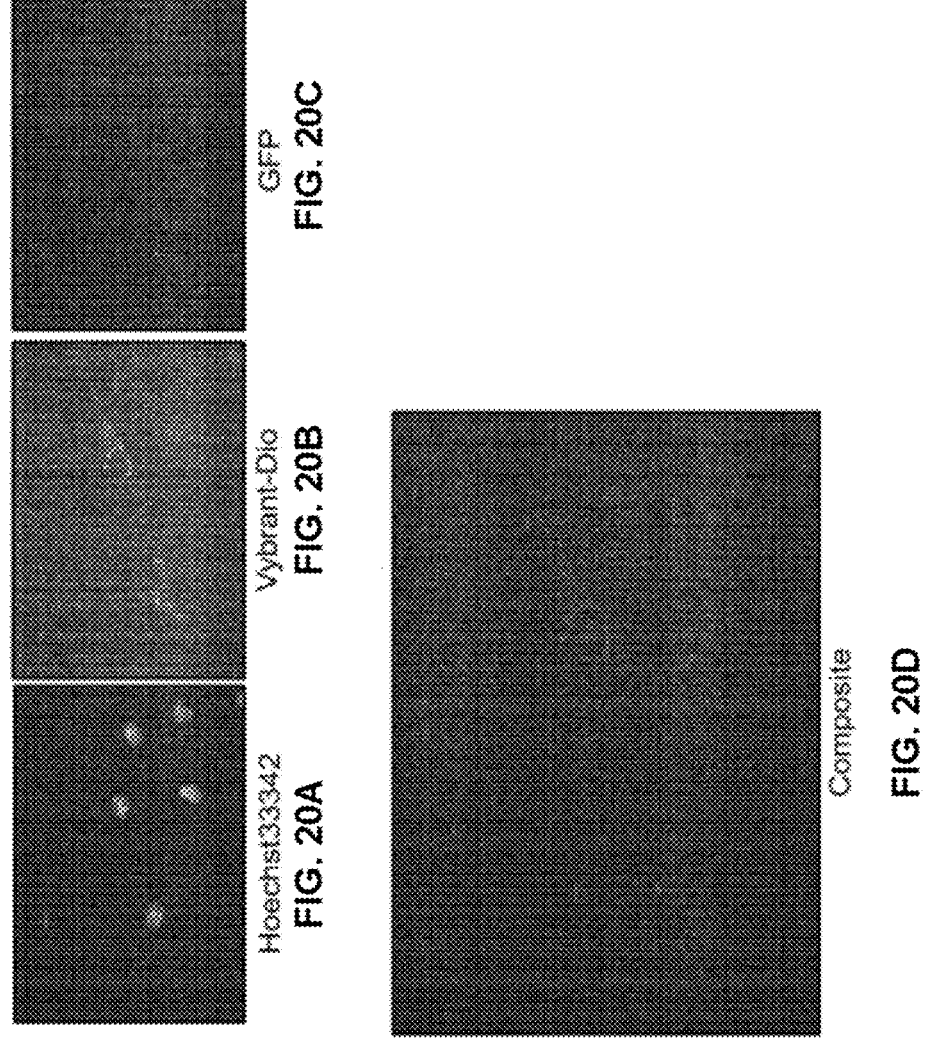

FIG. 20A-FIG. 20D shows the uptake of the microvesicles isolated according to the methods of the present invention from culture medium conditioned using bone marrow-derived stem cells obtained from a green fluorescent protein (GFP) expressing mouse into human dermal fibroblasts. Cell nuclei, resolved using Hoechst 33342 dye are shown in the panel labeled "Hoechst33342" (FIG. 20A). Cells, resolved using vybrant dye are shown in the panel labeled "Vybrant-Dio" (FIG. 20B). GFP-labeled microvesicles are shown in the panel labeled "GFP" (FIG. 20C). A panel where images obtained from all three dyes are overlaid is seen in the panel labeled "Composite" (FIG. 20D).

Figures 21A, 21B, 21C, 21D:
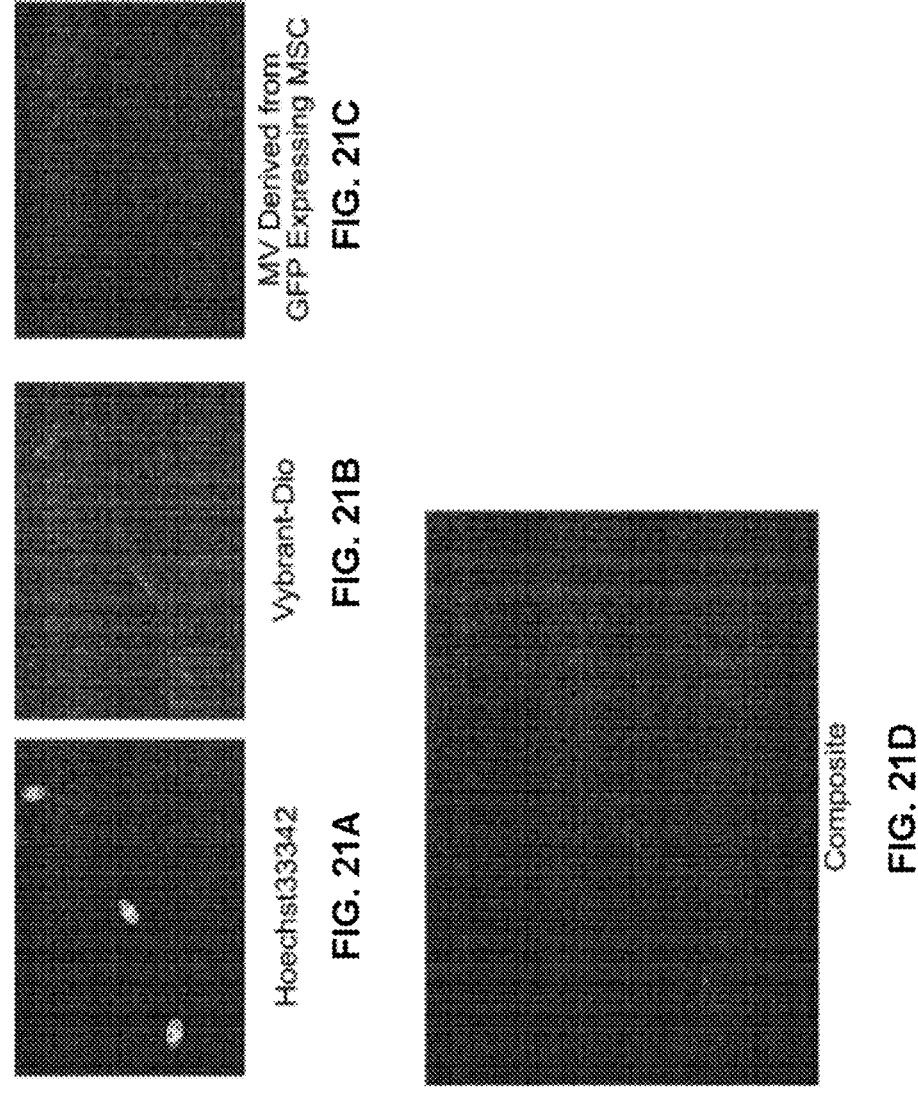

FIG. 21A-FIG. 21D shows the uptake of the microvesicles isolated according to the methods of the present invention from culture medium conditioned using bone marrow-derived stem cells obtained from a GFP expressing mouse into human dermal fibroblasts. Cell nuclei, resolved using Hoechst 33342 dye are shown in the panel labeled "Hoechst33342" FIG. 21A). Cells, resolved using vybrant dye are shown in the panel labeled "Vybrant-Dio" (FIG. 21B). GFP-labeled microvesicles are shown in the panel labeled "GFP" (FIG. 21C). A panel where images obtained from all three dyes are overlaid is seen in the panel labeled "Composite" (FIG. 21D).

Figures 22A, 22B, 22C, 22D:
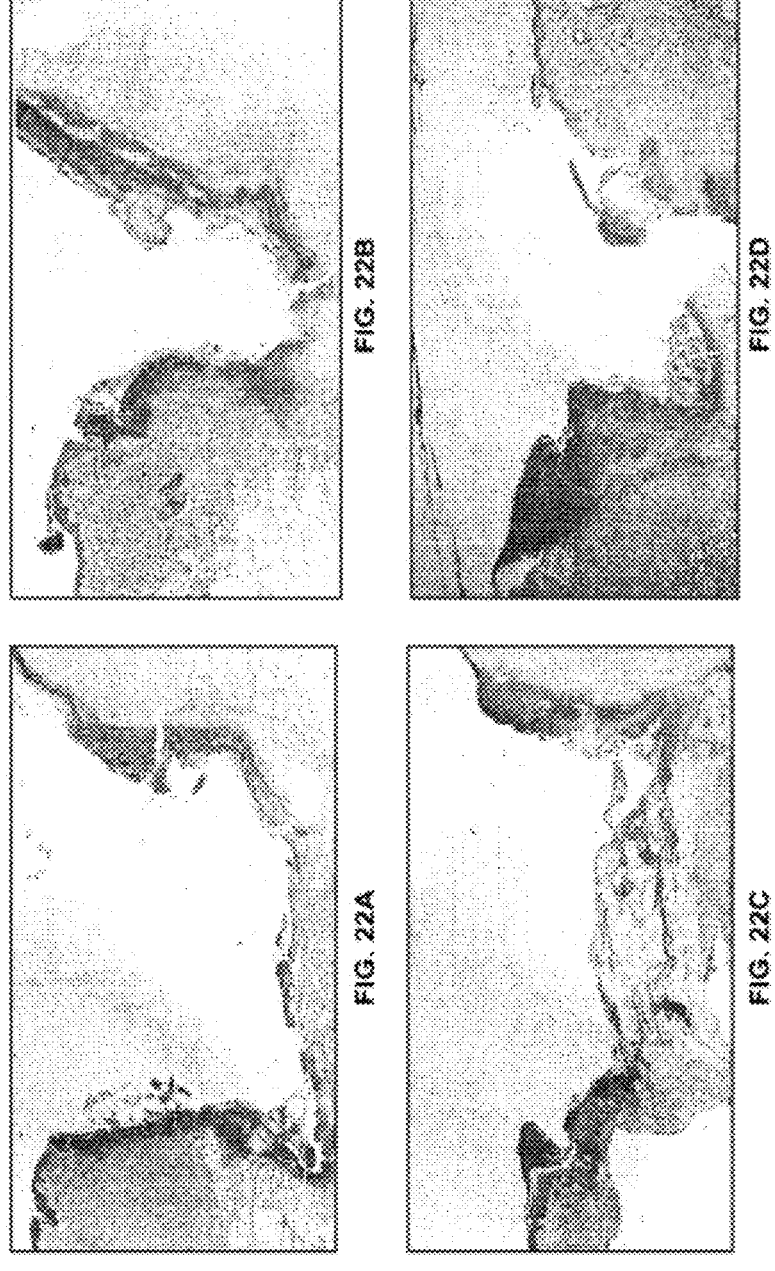

FIG. 22A-FIG. 22D show histological sections of full-thickness wounds from: FIG. 22A—untreated animals; FIG. 22B—microvesicles isolated from medium conditioned using autologous bone marrow-derived mesenchymal stem cells according to the methods of the present invention; FIG. 22C—saline; and FIG. 22D—microvesicles isolated from autologous bone marrow-derived mesenchymal stem cells by ultracentrifugation, 5 days post wound.

Figures 23A, 23B, 23C, 23D:
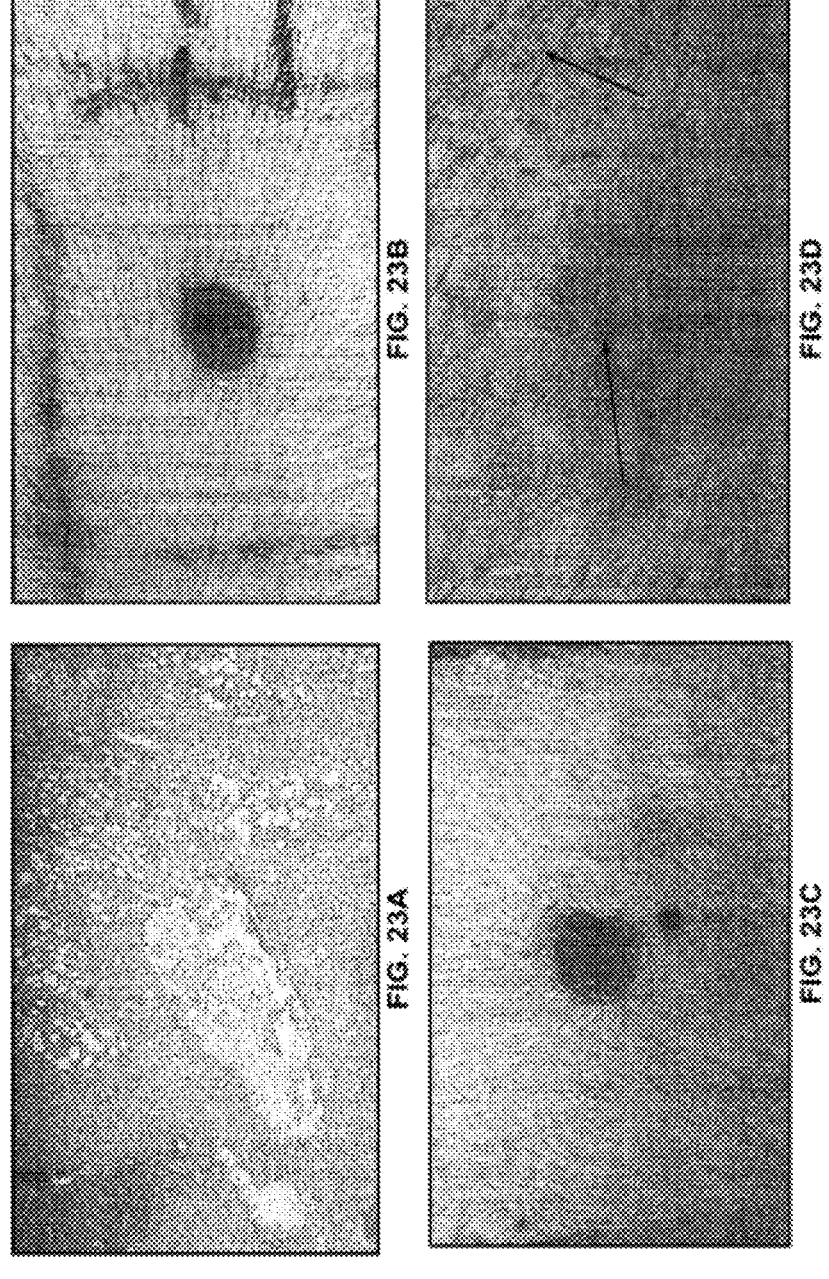

FIG. 23A-FIG. 23D show pictures of second degree burns on animals treated with: FIG. 23A—microvesicles isolated from medium conditioned using autologous bone marrow-derived mesenchymal stem cells by ultracentrifugation; FIG. 23B—microvesicles isolated from medium conditioned using autologous bone marrow-derived mesenchymal stem cells according to the methods of the present invention; and FIG. 23C—untreated animals, 7 days post wound. FIG. 23D—shows a full thickness wound in an animal treated with microvesicles isolated from medium conditioned using autologous bone marrow-derived mesenchymal stem cells by ultracentrifugation 7 days post wound. Arrows indicate abscess formation in a full thickness wound treated with microvesicles isolated by ultracentrifugation at Day 7 (40×). This was not observed in full thickness wounds treated with microvesicles prepared according to the methods of the present invention.

Figure 24:

FIG. 24 shows a histological slide of a second degree wound, 28 days post wound, from an animal treated with microvesicles isolated from medium conditioned using autologous bone marrow-derived mesenchymal stem cells according to the methods of the present invention.

Figure 25:
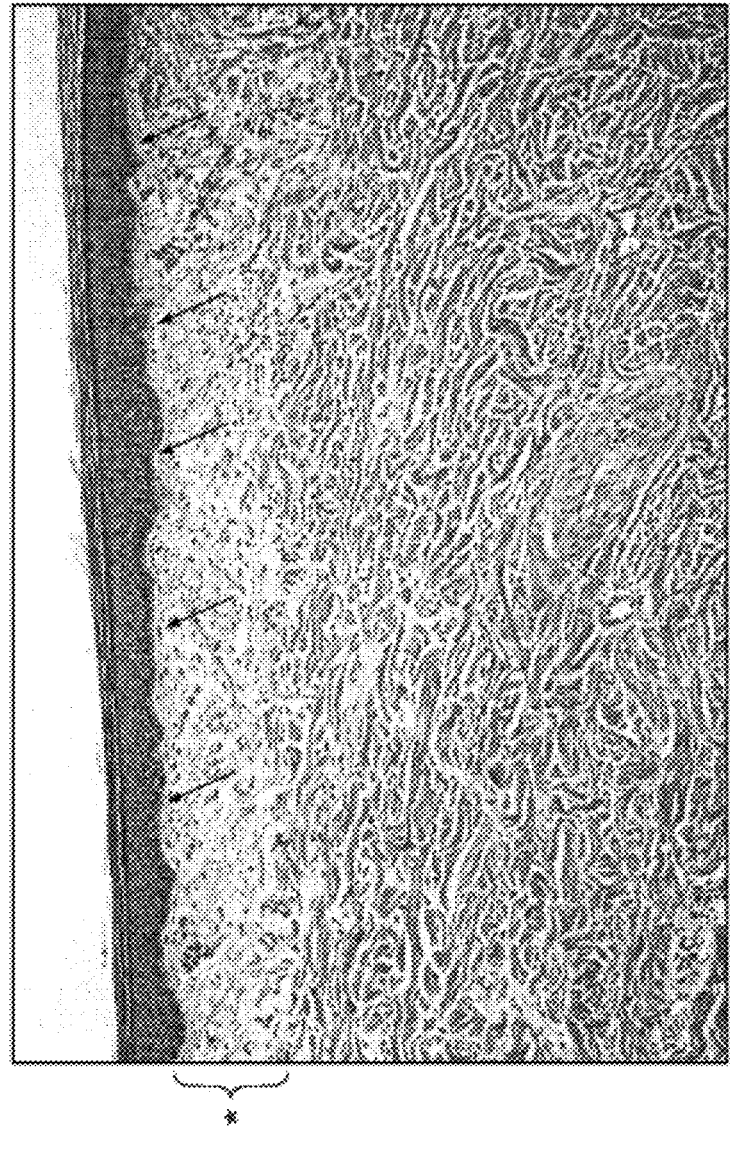

FIG. 25 shows a histological slide of a second-degree wound, 28 days post wound, from an animal treated with saline.

FIG. 26 shows a histological slide of a full-thickness wound, 28 days post wound, from an animal treated with microvesicles isolated from medium conditioned using autologous bone marrow-derived mesenchymal stem cells according to the methods of the present invention.

Figures 27A, 27B, 27C:
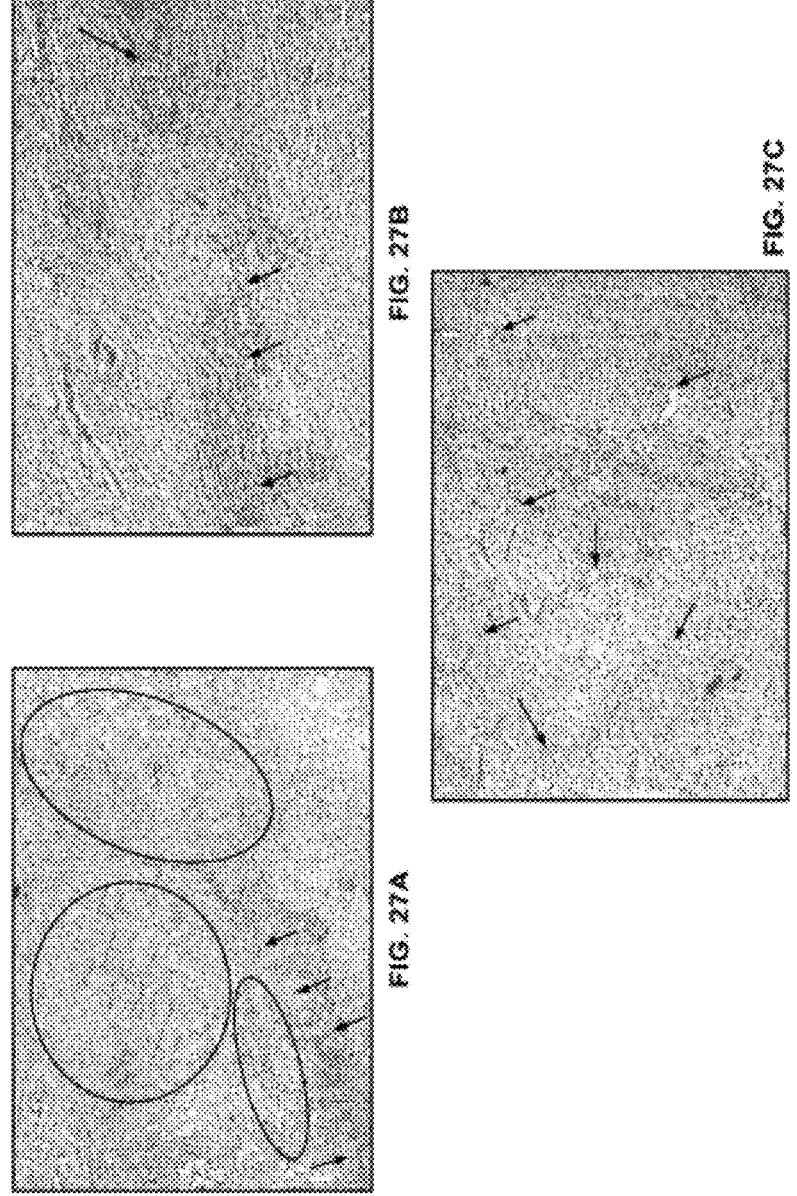

FIG. 27A-FIG. 27C show a histological slide of a full-thickness wound, 28 days post wound, from an animal treated with microvesicles isolated from medium conditioned using autologous bone marrow-derived mesenchymal stem cells according to the methods of the present invention. FIG. 27A shows new nerve growth (arrows) and angiogenesis (circles). FIG. 27B shows new nerve growth (arrows). FIG. 27C shows new blood vessel growth (arrows).

Figure 28:
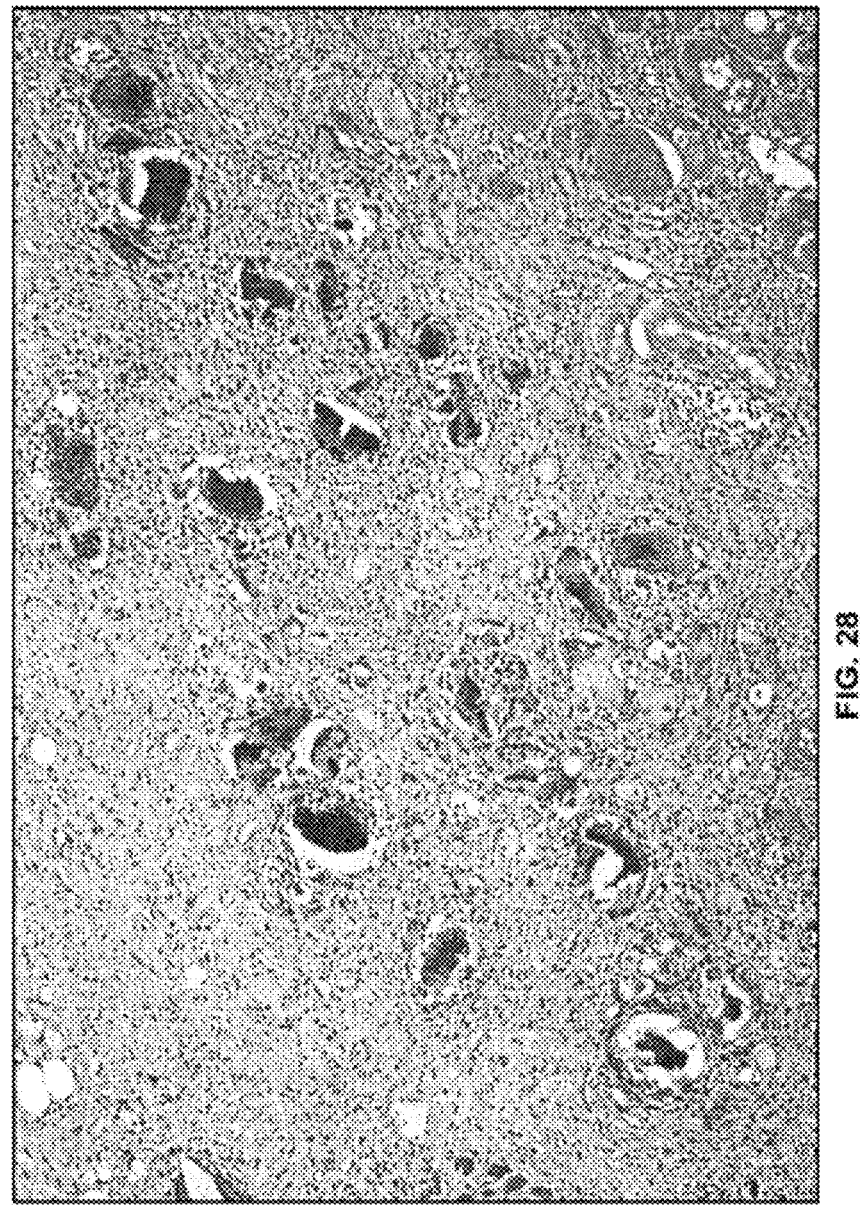

FIG. 28 shows a histological slide of a full-thickness wound, 7 days post wound in an animal treated with microvesicles derived from medium conditioned using autologous bone marrow-derived mesenchymal stem cells.

Figures 29A, 29B:
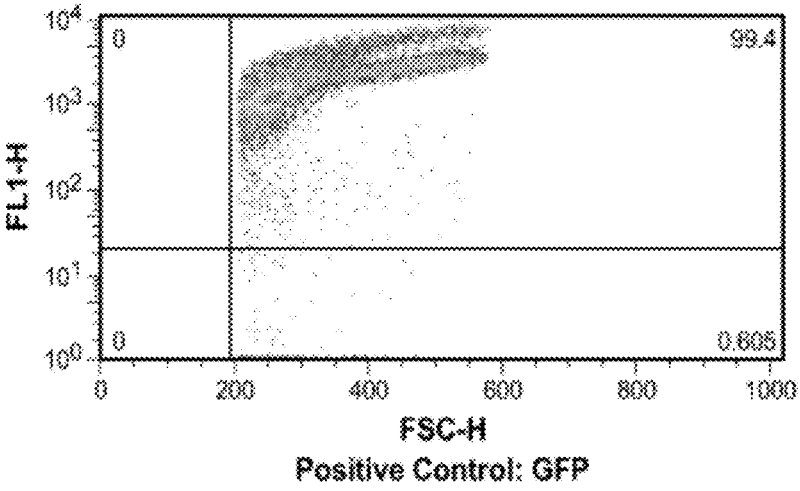

FIG. 29A-FIG. 29B show the presence or absence of chimerism in irradiated animals following administration of GFP-labeled bone marrow. FIG. 29A shows data for a positive control and FIG. 29B shows experimental data.

FIG. 30A-FIG. 30C show the effects of MSC treatment on hair growth following gamma irradiation (FIG. 30A and FIG. 30B), and the absence of chimerism in irradiated animals following administration of GFP-labeled bone marrow (FIG. 30C).

FIG. 31A-FIG. 31F shows the effect of bone marrow-derived microvesicles obtained using the method of the present invention on blood vessel formation, using an in vitro assay of angiogenesis. The upper three panels are representative images taken using an epifluorescent microscope of cultures of HUVEC cells treated with bone marrow-derived microvesicles obtained using the method of the present invention ("Bone Marrow Aspirate MV") (FIG.

Figures 31A, 31B, 31C, 31D, 31E, 31F:
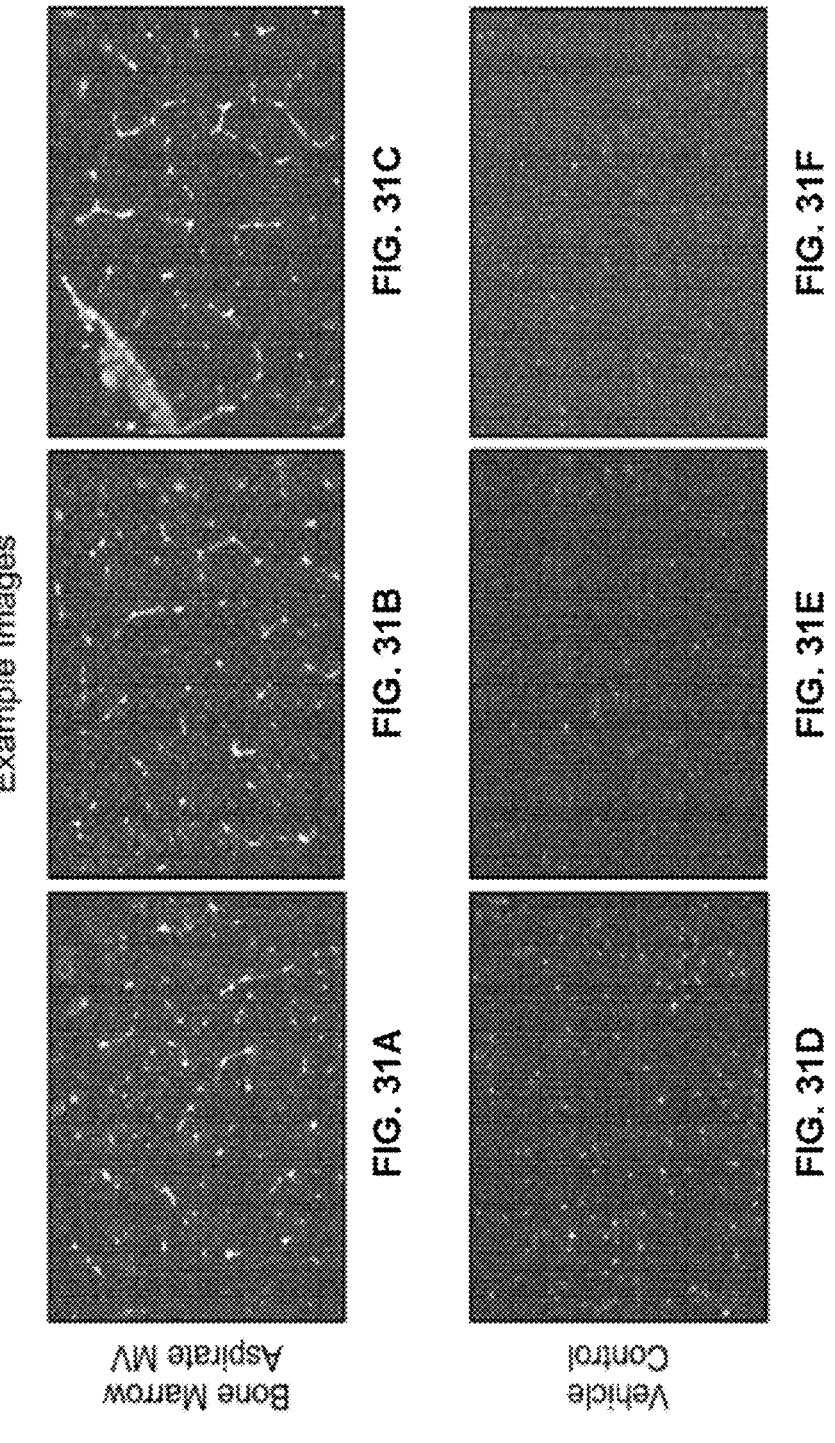

31A-FIG. 31C). The lower three panels are representative images taken using an epifluorescent microscope of cultures of HUVEC cells treated with vehicle control ("Vehicle Control") (FIG. 31D-FIG. 31F).

Figures 32A, 32B, 32C:
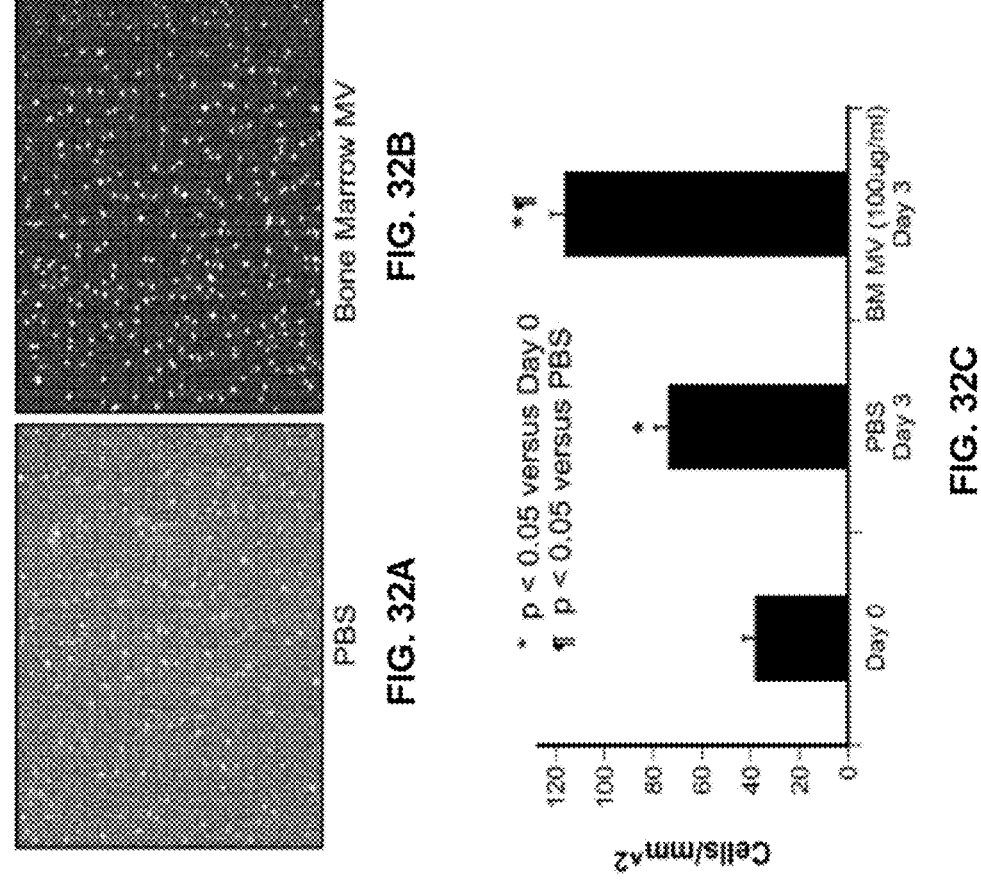

FIG. 32A-FIG. 32C show the effect of bone marrow-derived microvesicles obtained using the method of the present invention on cell growth or proliferation, using an in vitro assay of cell growth. FIG. 32A-FIG. 32B shows representative images taken using an epifluorescent microscope of cultures of normal adult fibroblasts treated with bone marrow-derived microvesicles obtained using the method of the present invention ("Bone Marrow MV"; FIG. 32B) or PBS ("PBS"; FIG. 32A), three days post treatment. FIG. 32C shows the average cell number in cultures of normal adult fibroblasts treated with bone marrow-derived microvesicles obtained using the method of the present invention ("Bone Marrow MV") or PBS ("PBS"), three days post treatment.

Figures 33A, 33B:
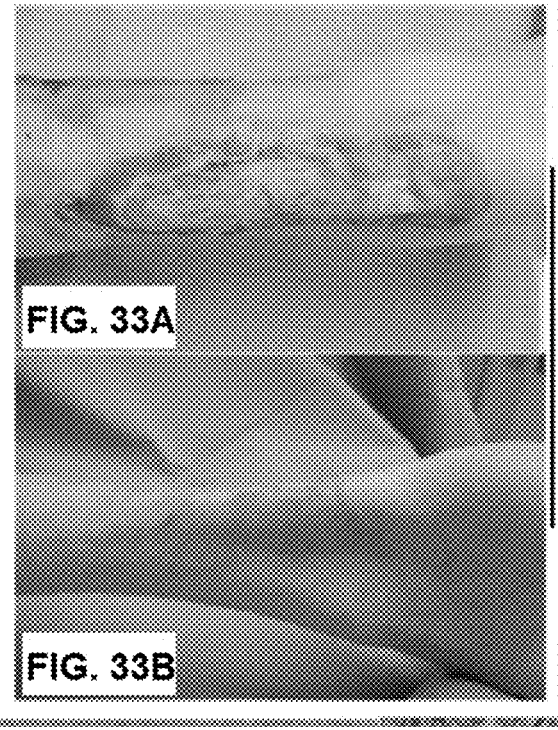

FIG. 33A-FIG. 33B show the results of chronic wound treatment with bone marrow stem cells (including BM-MSCs). FIG. 33A—Prior to treatment and before wound debridement. A necrotic Achilles tendon is visible. FIG. 33B—Healed post-administration (i.e., topical administration) of bone marrow cells.

Figures 34A, 34B, 34C:
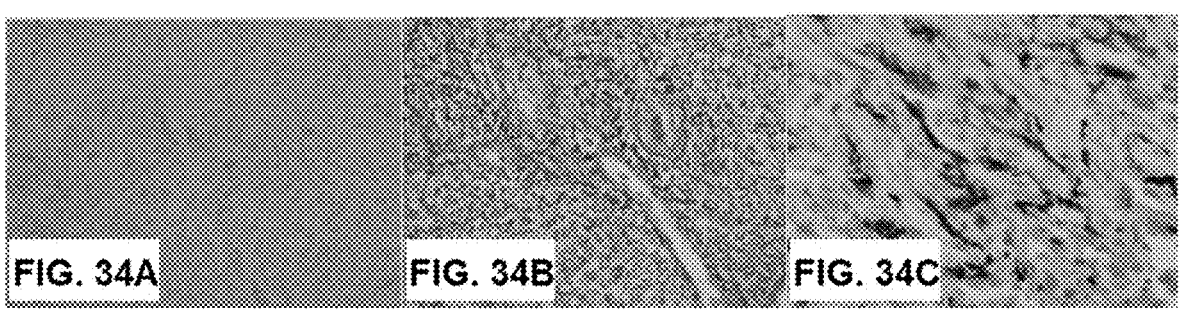

FIG. 34A-FIG. 34 C show dermal rebuilding in wounds treated with bone marrow stem cells. (A) FIG. 34A—pre-treatment biopsy of a fibrotic, scarred wound. Post-treatment biopsies with the generation of numerous reticulin fibers (FIG. 34B) and elastic fibers (FIG. 34C) are shown.

Figures 35A, 35B, 35C:
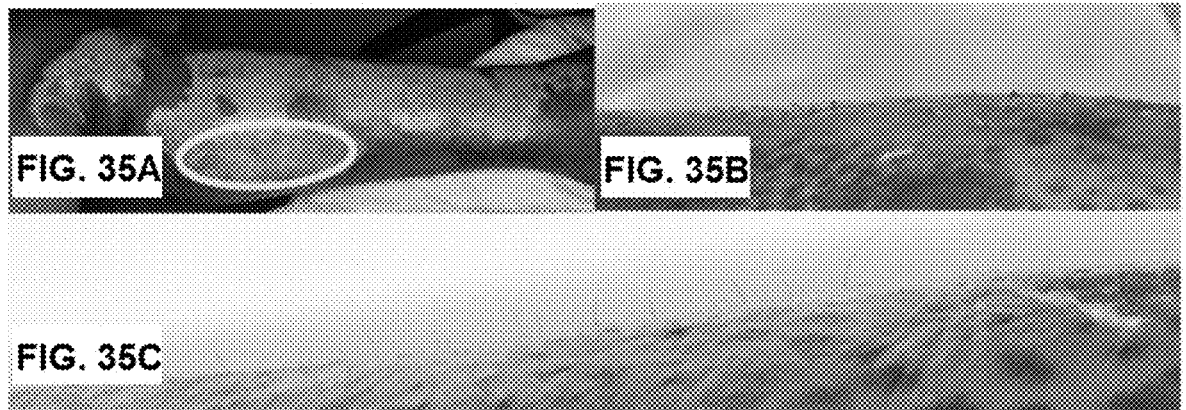

FIG. 35A-FIG. 35C show a deep second degree burn injury. The patient was given two administrations of BM-MSCs 11 days apart. FIG. 35A—Deep second degree burn injury day 0 (prior to treatment). The circled area represents the deepest portion of the burn injury. FIG. 35B—Hair follicle accentuation 11 days after the first administration (i.e., topical administration) of BM-MSCs. The accentuated follicles are noted in the circled area of A. FIG. 35C—Hair growth in in the circled area of FIG. 35A, 34 days after the second administration of BM-MSCs.

Figures 10A, 10B, 10C:
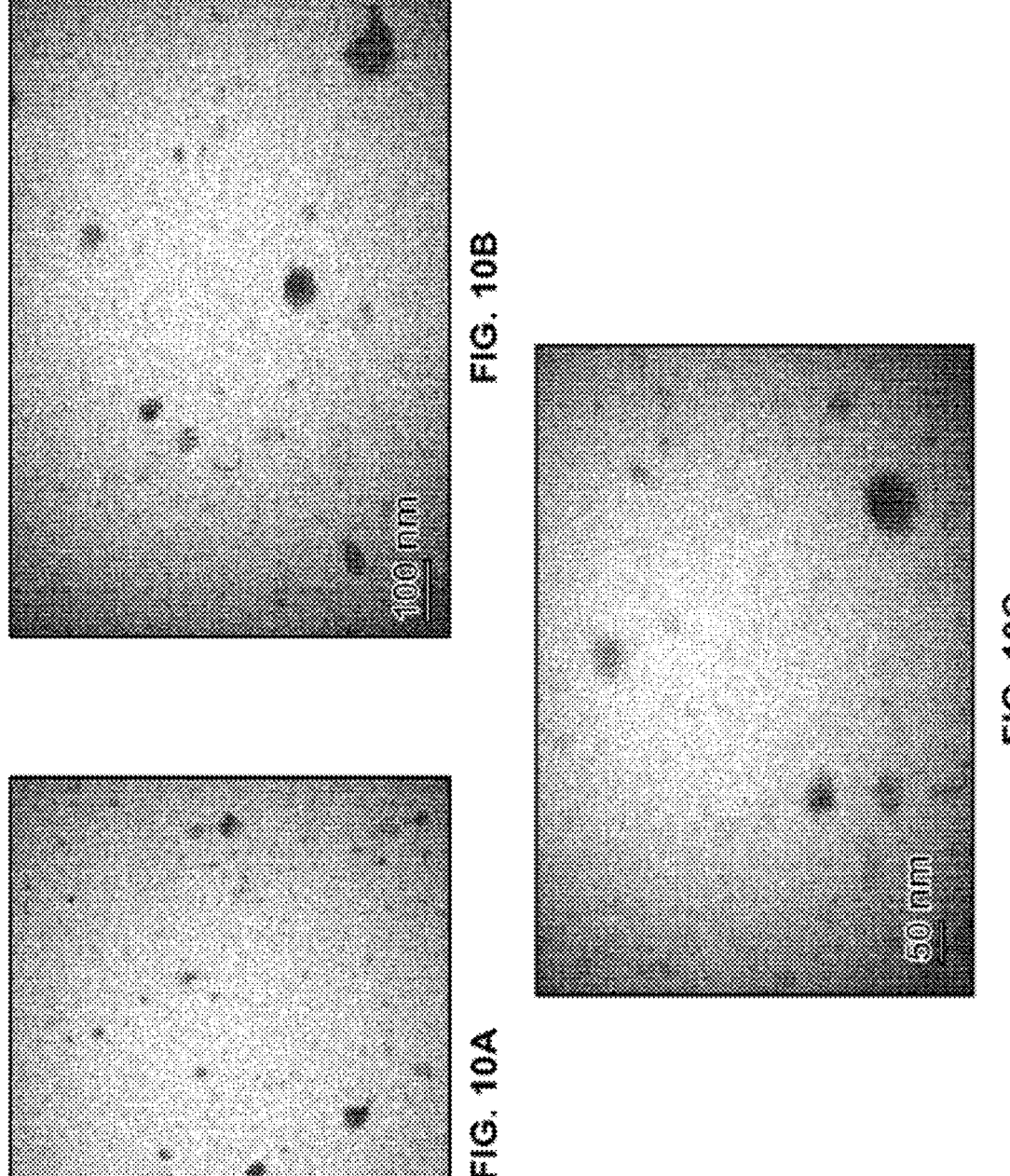
FIG. 10A-FIG. 10C show electron micrographs of microvesicles isolated from human urine according to the methods of the present invention.
Figures 36A, 36B, 36C:
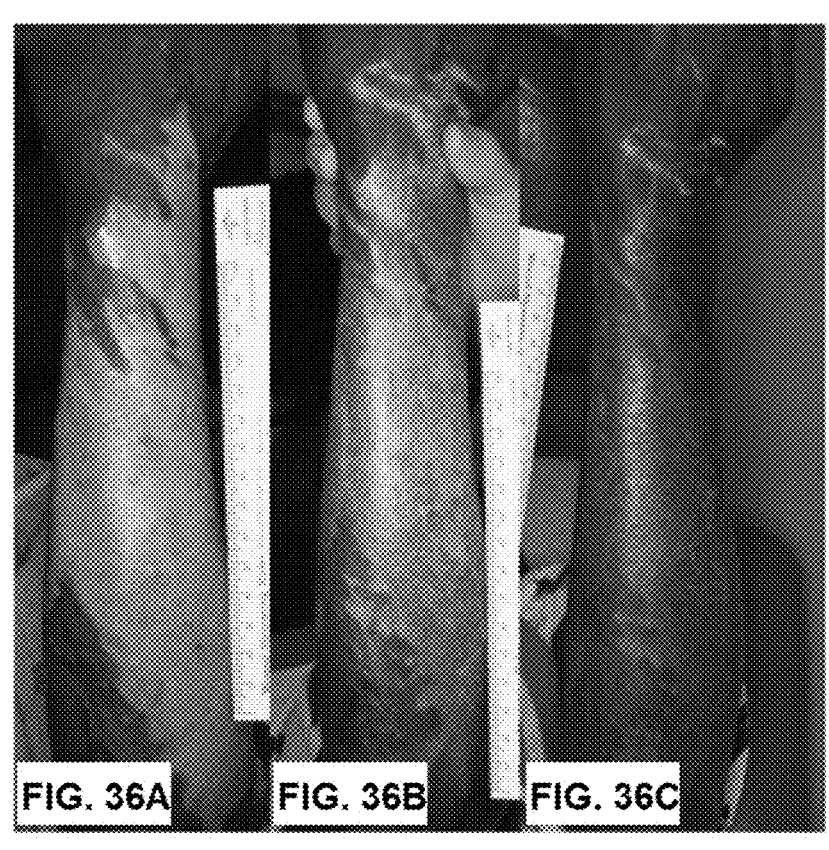

FIG. 36A-FIG. 36C show the healing of a burn patient treated with two topical administrations of MSCs given ten days apart. FIG. 36A—Prior to treatment. FIG. 36B—10 days post-treatment (i.e., topical administration) with first dose of MSCs. FIG. 36CA—7 days post-treatment with second dose of BM-MSCs (i.e., 17 days after FIG. 36A).

Figure 37A:
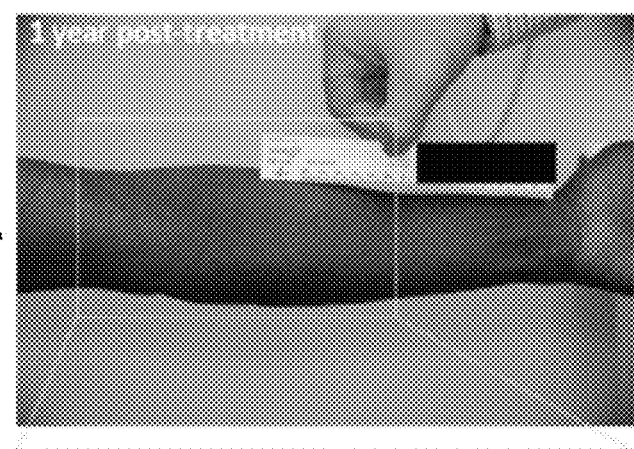
Figure 37B:

FIG. 37A-FIG. 37B shows no evidence of scarring in burn patient assessed one year post-treatment with BM-MSCs. FIG. 37A: left ventral forearm (bottom panel shows area outlined in yellow; FIG. 37B). The patient's skin showed evidence of normal elasticity with no evidence of scarring in the original burned areas.

Figures 38A, 38B:
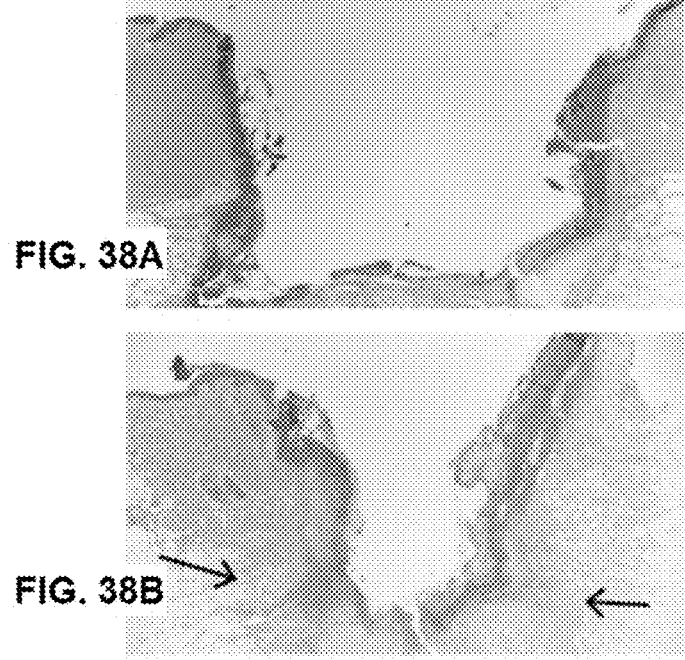

FIG. 38A-FIG. 38B show full thickness wounds (day 5) created on Yorkshire pigs. FIG. 38A—Untreated control. FIG. 38B—Wound treated with BM-MSC EVs according to certain embodiments of the invention. There was significantly greater closure of the would after treatment with BM-MSC EVs. Arrows indicate areas of increased dermal remodeling according to certain embodiments of the invention.

Figure 39A:
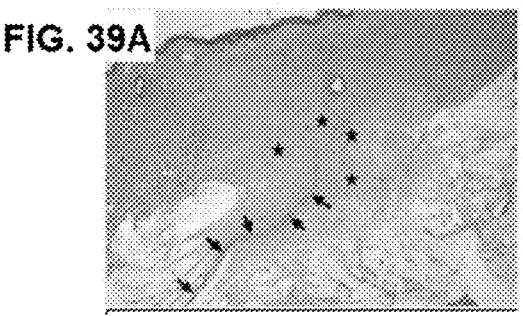
Figure 39B:
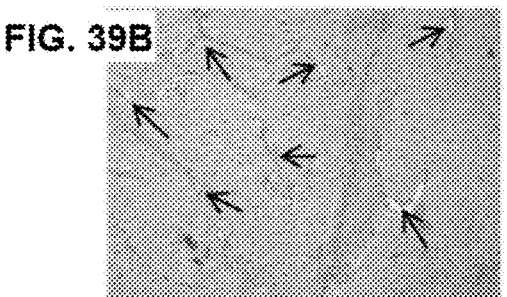
Figure 39C:
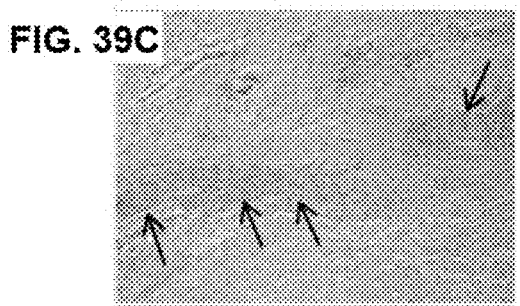

FIG. 39A-FIG. 39C show full thickness wounds (day 28) created on Yorkshire pigs treated with BM-MSC EVs according to certain exemplary embodiments. FIG. 39A—Arrows highlight nerve growth and stars illustrate vascular growth. FIG. 39B—Higher magnification illustrating vascular growth (arrows). FIG. 39C—Higher magnification illustrating nerve growth (arrows).

FIG. 40A-FIG. 40B shows second degree burn wounds in pigs 5 days post-treatment with intralesional injection of porcine BM-MSC EVs according to certain exemplary embodiments. FIG. 40A: EVs prepared by ultracentrifugation methods known in the art were used to treat a burn wound. The wound was raised and grossly inflamed with sterile pustule formation (indicative of an induced inflammatory response and not infection) and reduced healing. FIG. 40B: EVs prepared using exemplary methods described herein were used to treat a burn wound. The wound has accelerated healing with reduced inflammation compared to traditional EVs prepared by ultracentrifugation.

FIG. 41A-FIG. 41B graphically depicts enrichment of COL7A1 mRNA in BM-MSC EVs (middle bars in each panel). EV treatment increased COL7A1 expression in RDEB fibroblasts. FIG. 41A shows COL7A1 expression detected with primer pair 1; FIG. 41B shows COL7A1 expression detected with primer pair 2. Gene expression was normalized by beta-actin expression, a common EV housekeeping gene.

Figure 42:
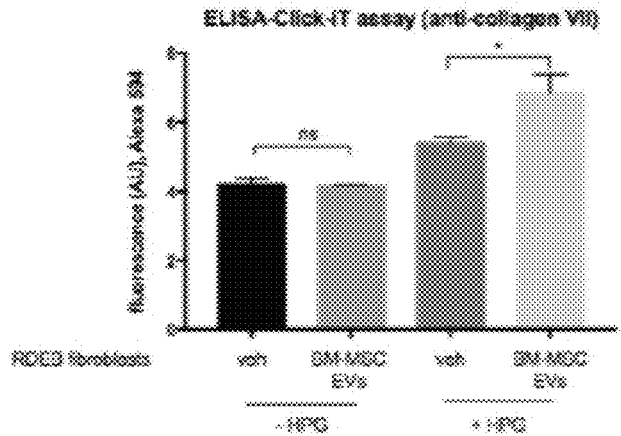

FIG. 42 graphically depicts a chemo selective ligation assay (utilizing "click iT" reaction chemistry) that revealed production of new collagen VII from RDEB fibroblasts following co-treatment with BM-MSC EVs (10 μg/mL) and the L-methionine analog L-homopropargylglycine (HPG) (a modified amino acid) which incorporates into newly synthesized proteins.

FIG. 43A-FIG. 43B graphically depict that BM-MSC EVs significantly promote both RDEB proliferation (FIG. 43A) and resistance to trypsin digestion (FIG. 43B), both standard in vitro assays to assess gain-of-function support the pro-wound healing potential of RDEB dermal fibroblasts.

FIG. 44A-FIG. 44C show the validation of an in vitro cell line derived from an infant diagnosed as having RDEB (Hallopeau-Siemens type). The RDEB fibroblasts expressed significantly less COL7A1 compared to fibroblasts derived from non-affected subjects (NHF). FIG. 44A—Primer pairs 1 and 2 designed near 3' end of cDNA corresponding to 5' end of mRNA. FIG. 44B—COL7A1 gene expression in normal human fibroblasts (NHFs) and in RDEB fibroblasts. FIG. 44C—RDEB cells secreted low levels of collagen VII protein relative to normal (control) human fibroblasts.

Figures 45A, 45B:
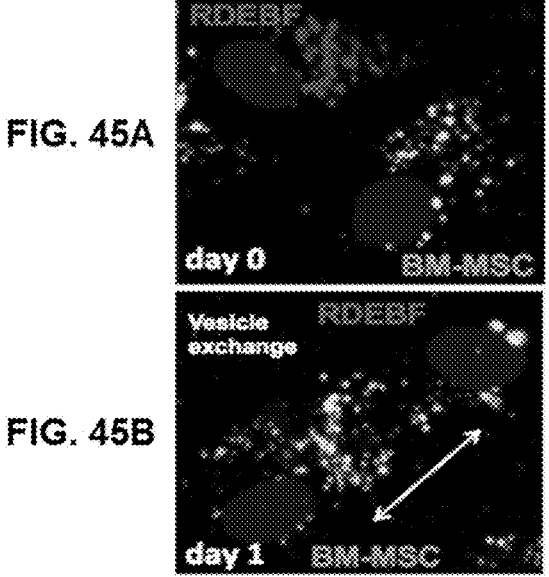

FIG. 45A-FIG. 45B shows vesicle exchange between BM-MSCs and RDEB fibroblasts. RDEBFs (stained with lipid dye Dil (red)) and BM-MSCs (stained with lipid dye DiO (green)) were co-cultured (day 0; FIG. 45A), and, within one day, began to uptake extracellular vesicles (yellow) (day 1; FIG. 45B). Scale bar, 10 μm.

Figures 46A, 46B, 46C, 46D:
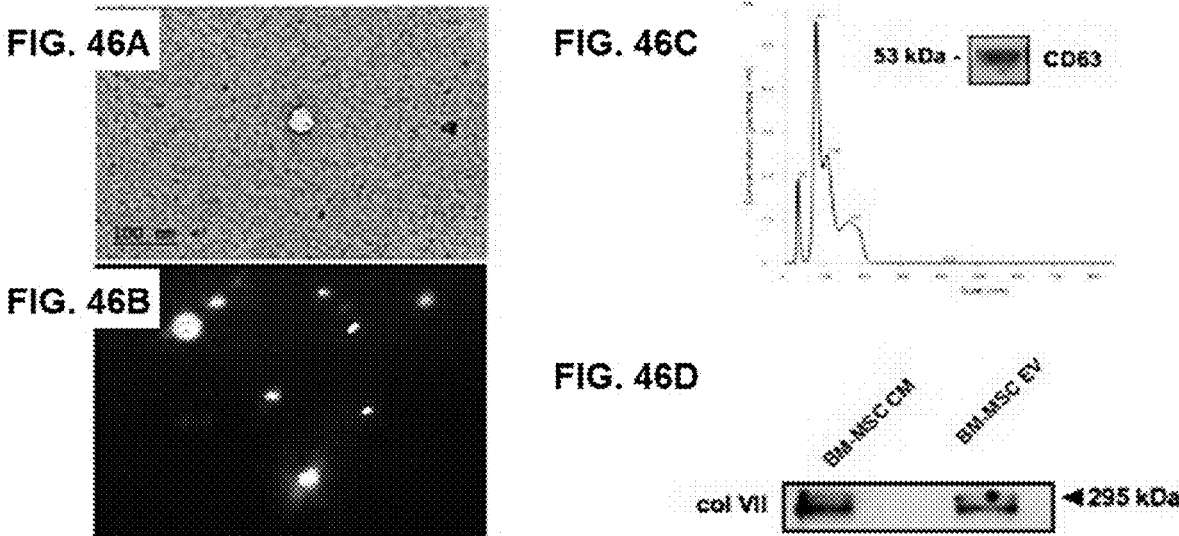

FIG. 46A-FIG. 46D show that collagen VII protein co-isolated with BM-MSC extracellular vesicles (EVs). FIG. 46A—Transmission electron micrograph of an extracellular vesicle isolated from BM-MSC serum-free conditioned media (CM). FIG. 46B—NanoSight image of BM-MSC EVs, diluted 1:500. FIG. 46C—Histogram of size vs concentration (diluted 1:500). Inset shows EVs contain CD63 exosome marker. FIG. 46D—Collagen VII protein in BM-MSC CM and associated with purified BM-MSC EVs.

Figures 47A, 47B:
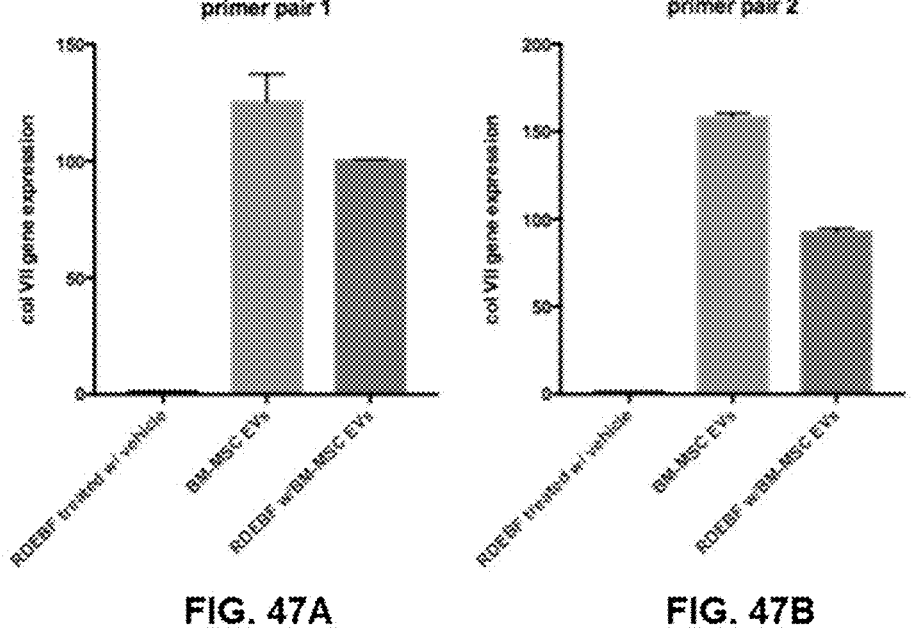

FIG. 47A-FIG. 47B shows enrichment of COL7A1 mRNA in BM-MSC EVs (middle bars in each panel). EV treatment increased COL7A1 expression in RDEB fibroblasts. FIG. 47A shows COL7A1 expression detected with primer pair 1; FIG. 47B shows COL7A1 expression detected with primer pair 2. Gene expression was normalized by beta-actin expression, a common EV housekeeping gene.

Figure 48A:
Figure 48B:
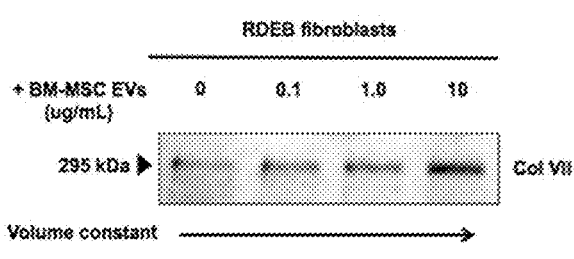
Figure 48C:
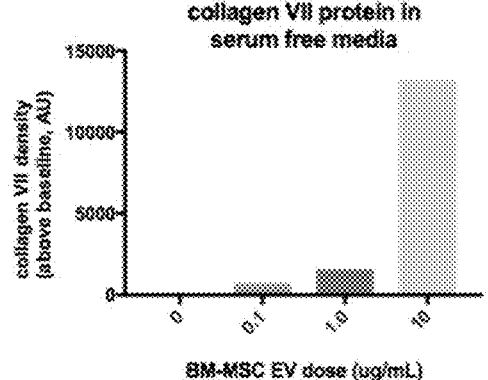

FIG. 48A-FIG. 48C show that RDEB fibroblasts treated with BM-MSC EVs contained more collagen VII protein in media 3 days after washing. FIG. 48A—Treatment schematic. FIG. 48B—Western blot of collagen VII in RDEB media. FIG. 48C—Densitometry quantification of FIG. 48B (above baseline collagen VII detection).

Figure 49A:
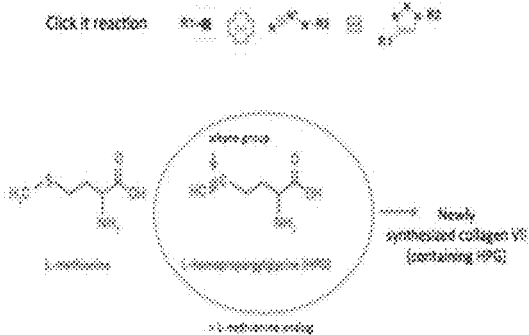
Figure 49B:
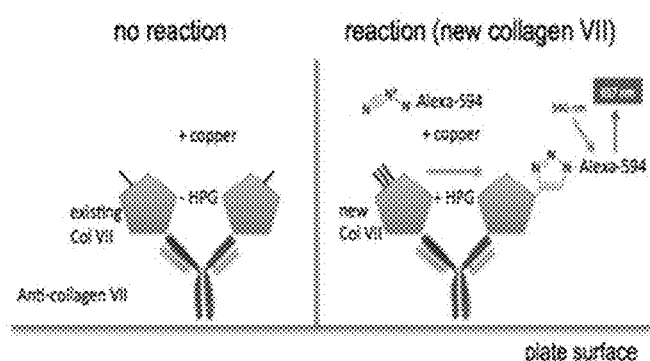
Figure 49C:
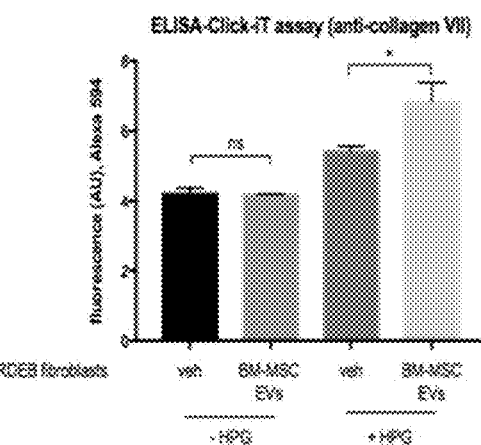

FIG. 49A-FIG. 49C depict a chemoselective ligation assay (utilizing "click iT" reaction chemistry) (FIG. 49A and FIG. 49B) that revealed production of new collagen VII from RDEB fibroblasts following co-treatment with BM-MSC EVs (10 μg/mL) and L-methionine analog L-homopropargylglycine (HPG) (a modified amino acid) which incorporates into newly synthesized proteins (FIG. 49C).

FIG. 50A-FIG. 50B show that BM-MSC EVs increased in vitro surrogate assays related to wound healing (proliferation and trypsin-resistance) of RDEB fibroblasts. FIG. 50A-Proliferation (MTT) assay. FIG. 50B—Trypsin resistance assay.

FIG. 51A-FIG. 51E shows BM-MSCs that were delivered in saline to burn patients in a clinical trial. BM-MSCs secreted large numbers of EVs (CD63 positive) in saline within hours (shown, 4 hours). FIG. 51A, NanoSight of saline buffer background; FIG. 51B, NanoSight EVs in saline (diluted 1:500); FIG. 51C: histogram of 1:500 dilution of saline delivered in burn clinical trial, bar graph quantification (FIG. 51D). Western blot shows CD63 (exosome marker) secreted by BM-MSCs within 4 hours (FIG. 51E).

Figure 52:
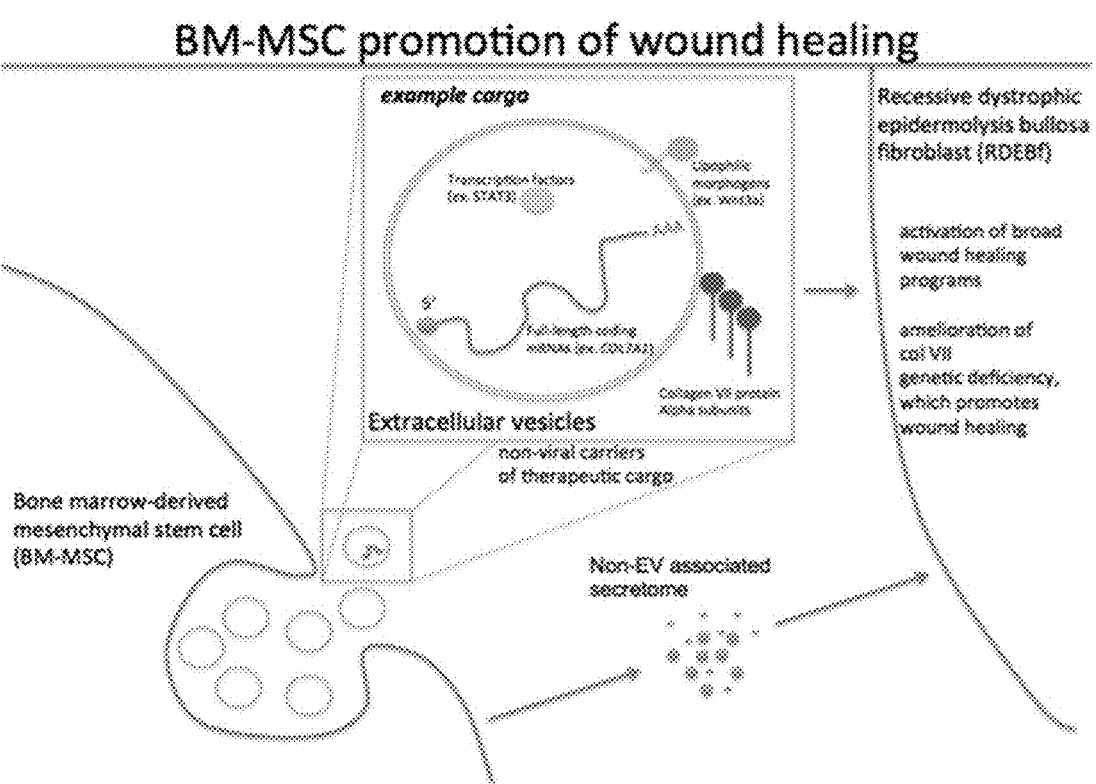

FIG. 52 depicts a model according to certain exemplary embodiments of the invention in which the secretome of BM-MSCs contains EV-associated and non-EV-associated proteins that deliver multiple pro-wound healing functions to RDEB fibroblasts, including collagen VII protein, collagen VII mRNA, STAT3-signaling activators, and canonical Wnt activators.

DETAILED DESCRIPTION

For clarity of disclosure, and not by way of limitation, the detailed description of the invention is divided into the following subsections that describe or illustrate certain features, embodiments or applications of the present invention. Methods to Isolate the Microvesicles of the Present Invention As used herein, the term "microvesicles" refers to vesicles comprising lipid bilayers, formed from the plasma membrane of cells, and are heterogeneous in size, ranging from about 2 nm to about 5000 nm. The cell from which a microvesicle is formed is herein referred to as "the host cell." Microvesicles are a heterogeneous population of vesicles and include, but are not limited to, extracellular vesicles (EVs), ectosomes, microparticles, microvesicles, nanovesicles, shedding vesicles, membrane particles and the like.

Microvesicles exhibit membrane proteins from their host cell on their membrane surface, and may also contain molecules within the microvesicle from the host cell, such as, for example, mRNA, miRNA, tRNA, RNA, DNA, lipids, proteins or infectious particles. These molecules may result from, or be, recombinant molecules introduced into the host cell. Microvesicles play a critical role in intercellular communication, and can act locally and distally within the body, inducing changes in cells by fusing with a target cell, introducing the molecules transported on and/or in the microvesicle to the target cell. For example, microvesicles have been implicated in anti-tumor reversal, cancer, tumor immune suppression, metastasis, tumor-stroma interactions, angiogenesis and tissue regeneration. Microvesicles may also be used to diagnose disease, as they have been shown to carry bio-markers of several diseases, including, for example, cardiac disease, HIV and leukemia.

In one embodiment, microvesicles are isolated from a biological fluid containing microvesicles in a method comprising the steps of:
- a) obtaining a biological fluid containing microvesicles,
- b) clarifying the biological fluid to remove cellular debris,
- c) precipitating the microvesicles by adding a precipitating agent to the clarified biological fluid,
- d) collecting the precipitated microvesicles and washing the material to remove the precipitating agent, and
- e) suspending the washed microvesicles in a solution for storage or subsequent use.

In one embodiment, the biological fluid is clarified by centrifugation. In an alternate embodiment, the biological fluid is clarified by filtration.

In one embodiment, the precipitated microvesicles are collected by centrifugation. In an alternate embodiment, the precipitated microvesicles are collected by filtration.

In one embodiment, microvesicles are isolated from a biological fluid containing microvesicles in a method comprising the steps of:
- a) obtaining a biological fluid containing microvesicles,
- b) clarifying the biological fluid to remove cellular debris,
- c) precipitating the microvesicles by adding a precipitating agent to the clarified biological fluid,
- d) collecting the precipitated microvesicles and washing the material to remove the precipitating agent,
- e) suspending the washed microvesicles in a solution, and
- f) processing the microvesicles to analyze the nucleic acid, carbohydrate, lipid, small molecules and/or protein content.

In one embodiment, the biological fluid is clarified by centrifugation. In an alternate embodiment, the biological fluid is clarified by filtration.

In one embodiment, the precipitated microvesicles are collected by centrifugation. In an alternate embodiment, the precipitated microvesicles are collected by filtration.

In one embodiment, the present invention provides reagents and kits to isolate microvesicles from biological fluids according to the methods of the present invention.

The biological fluid may be peripheral blood, sera, plasma, ascites, urine, cerebrospinal fluid (CSF), sputum, saliva, bone marrow, synovial fluid, aqueous humor, amniotic fluid, cerumen, breast milk, broncheo alveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids.

The biological fluid may also be derived from the blastocyl cavity, umbilical cord blood, or maternal circulation, which may be of fetal or maternal origin. The biological fluid may also be derived from a tissue sample or biopsy.

The biological fluid may be derived from plant cells of cultures of plant cells. The biological fluid may be derived from yeast cells or cultures of yeast cells.

In one embodiment, the biological fluid is cell culture medium. In one embodiment, the cell culture medium is conditioned using tissues and/or cells prior to the isolation of microvesicles according to the methods of the present invention.

The term "conditioned" or "conditioned medium" refers to medium, wherein a population of cells or tissue, or combination thereof is grown, and the population of cells or tissue, or combination thereof contributes factors to the medium. In one such use, the population of cells or tissue, or combination thereof is removed from the medium, while the factors the cells produce remain. In one embodiment, the factors produced are microvesicles. Medium may be conditioned via any suitable method selected by one of ordinary skill in the art. For example, medium may be cultured according to the methods described in EP1780267A2.

In one embodiment, microvesicles are isolated from cells or tissue that have been pre-treated prior to the isolation of the microvesicles. Pretreatment may include, for example, culture in a specific medium, a medium that contains at least one additive, growth factor, medium devoid of serum, or a combination thereof. Alternatively, pretreatment may comprise contacting cells or tissues with additives (e.g. interleukin, VEGF, inducers of transcription factors, transcription factors, hormones, neurotransmitters, pharmaceutical compounds, microRNA), transforming agents (e.g. liposome, viruses, transfected agents, etc.). Alternatively, pretreatment may comprise exposing cells or tissue to altered physical conditions (e.g. hypoxia, cold shock, heat shock and the like).

In one embodiment, microvesicles are isolated from medium conditioned using cells or tissue that have been pre-treated prior to the isolation of the microvesicles. Pretreatment may include, for example, culture in a specific medium, a medium that contains at least one additive, growth factor, medium devoid of serum, or a combination thereof. Alternatively, pretreatment may comprise contacting cells or tissues with additives (e.g. interleukin, VEGF, inducers of transcription factors, transcription factors, hormones, neurotransmitters, pharmaceutical compounds, microRNA), transforming agents (e.g. liposome, viruses, transfected agents, etc.). Alternatively, pretreatment may comprise exposing cells or tissue to altered physical conditions (e.g. hypoxia, cold shock, heat shock and the like).

In one embodiment, the biological fluid is an extract from a plant. In an alternate embodiment, the biological fluid is a cell culture medium from a culture of plant cells. In an alternate embodiment, the biological fluid is yeast extract. In an alternate embodiment, the biological fluid is a cell culture medium from a culture of yeast cells.

While the methods of the present invention may be carried out at any temperature, one of ordinary skill in the art can readily appreciate that certain biological fluids may degrade, and such degradation is reduced if the sample is maintained at a temperature below the temperature at which the biological fluid degrades. In one embodiment, the method of the present invention is carried out at 4° C. In an alternate embodiment, at least one step of the method of the present invention is carried out at 4° C. In certain embodiments, the biological fluid may be diluted prior to being subjected to the methods of the present invention. Dilution may be required for viscous biological fluids, to reduce the viscosity of the sample, if the viscosity of the sample is too great to obtain an acceptable yield of microvesicles. The dilution may be a 1:2 dilution. Alternatively, the dilution may be a 1:3 dilution. Alternatively, the dilution may be a 1:4 dilution. Alternatively, the dilution may be a 1:5 dilution. Alternatively, the dilution may be a 1:6 dilution. Alternatively, the dilution may be a 1:7 dilution. Alternatively, the dilution may be a 1:8 dilution. Alternatively, the dilution may be a 1:9 dilution. Alternatively, the dilution may be a 1:10 dilution. Alternatively, the dilution may be a 1:20 dilution. Alternatively, the dilution may be a 1:30 dilution. Alternatively, the dilution may be a 1:40 dilution. Alternatively, the dilution may be a 1:50 dilution. Alternatively, the dilution may be a 1:60 dilution. Alternatively, the dilution may be a 1:70 dilution. Alternatively, the dilution may be a 1:80 dilution. Alternatively, the dilution may be a 1:90 dilution. Alternatively, the dilution may be a 1:100 dilution.

The biological fluid may be diluted with any diluent, provided the diluent does not affect the functional and/or structural integrity of the microvesicles. One of ordinary skill in the art may readily select a suitable diluent. Diluents may be, for example, phosphate buffered saline, cell culture medium, and the like.

In one embodiment, the biological fluid is clarified by the application of a centrifugal force to remove cellular debris. The centrifugal force applied to the biological fluid is sufficient to remove any cells, lysed cells, tissue debris from the biological fluid, but the centrifugal force applied is insufficient in magnitude, duration, or both, to remove the microvesicles. The biological fluid may require dilution to facilitate the clarification.

The duration and magnitude of the centrifugal force used to clarify the biological fluid may vary according to a number of factors readily appreciated by one of ordinary skill in the art, including, for example, the biological fluid, the pH of the biological fluid, the desired purity of the isolated microvesicles, the desired size of the isolated microvesicles, the desired molecular weight of the microvesicles, and the like. In one embodiment, a centrifugal force of 2000×g is applied to the biological fluid for 30 minutes.

The clarified biological fluid is contacted with a precipitation agent to precipitate the microvesicles. In one embodiment, the precipitation agent may be any agent that surrounds the microvesicles and displaces the water of solvation. Such precipitation agents may be selected from the group consisting of polyethylene glycol, dextran, and polysaccharides.

In an alternate embodiment, the precipitation agent may cause aggregation of the microvesicles.

In an alternate embodiment, the precipitation agent is selected from the group consisting of calcium ions, magnesium ions, sodium ions, ammonium ions, iron ions, organic solvents such as ammonium sulfate, and flocculating agents, such as alginate.

The clarified biological fluid is contacted with the precipitation agent for a period of time sufficient to precipitate the microvesicles. The period of time sufficient to precipitate the microvesicles may vary according to a number of factors readily appreciated by one of ordinary skill in the art, including, for example, the biological fluid, the pH of the biological fluid, the desired purity of the isolated microvesicles, the desired size of the isolated microvesicles, the desired molecular weight of the microvesicles, and the like. In one embodiment, the period of time sufficient to precipitate the microvesicles is 6 hours.

In one embodiment, the clarified biological fluid is contacted with the precipitation agent for a period of time sufficient to precipitate the microvesicles at 4° C.

The concentration of the precipitation agent used to precipitate the microvesicles from a biological fluid may vary according to a number of factors readily appreciated by one of ordinary skill in the art, including, for example, the biological fluid, the pH of the biological fluid, the desired purity of the isolated microvesicles, the desired size of the isolated microvesicles, the desired molecular weight of the microvesicles, and the like.

In one embodiment, the precipitation agent is polyethylene glycol. The molecular weight of polyethylene glycol used in the methods of the present invention may be from about 200 Da to about 10,000 Da. In one embodiment, the molecular weight of polyethylene glycol used in the methods of the present invention may be greater than 10,000 Da. In certain embodiments, the molecular weight of polyethylene glycol used in the methods of the present invention is 10,000 Da or 20,000 Da. The choice of molecular weight may be influenced by a variety of factors including, for example, the viscosity of the biological fluid, the desired purity of the microvesicles, the desired size of the microvesicles, the biological fluid used, and the like. In one embodiment, the molecular weight of polyethylene glycol used in the methods of the present invention may be from about 200 Da to about 8,000 Da, or is approximately any of 200 Da, 300 Da, 400 Da, 600 Da, 1000 Da, 1450 Da, 1500 Da, 2000 Da, 3000 Da, 3350 Da, 4000 Da, 6000 Da, 8000 Da, 10000 Da, 20000 Da or 35000 Da or any ranges or molecular weights in between.

In one embodiment, the molecular weight of polyethylene glycol used in the methods of the present invention is about 6000 Da.

In one embodiment, the average molecular weight of polyethylene glycol used in the methods of the present invention is about 8000 Da.

In one embodiment, the average molecular weight of polyethylene glycol used in the methods of the present invention is about 10000 Da.

In one embodiment, the average molecular weight of polyethylene glycol used in the methods of the present invention is about 20000 Da.

The concentration of polyethylene glycol used in the methods of the present invention may be from about 0.5% w/v to about 100% w/v. The concentration of polyethylene glycol used in the methods of the present invention may be influenced by a variety of factors including, for example, the viscosity of the biological fluid, the desired purity of the microvesicles, the desired size of the microvesicles, the biological fluid used, and the like.

In certain embodiments, the polyethylene glycol is used in the concentration of the present invention at a concentration between about 5% and 25% w/v. In certain embodiments, the concentration is about 5%, 6%, 7%, 8%, 9%, 10%, 11%, 12%, 13%, 14%, or 15%, or a range between any two of these values.

In one embodiment, the concentration of polyethylene glycol used in the methods of the present invention is about 8.5% w/v.

In one embodiment, the concentration of polyethylene glycol used in the methods of the present invention is about 6% w/v.

In one embodiment, polyethylene glycol having an average molecular weight of 6000 Da is used, at a concentration of 8.5% w/v. In one embodiment, the polyethylene glycol is diluted in 0.4M sodium chloride.

In one embodiment, the concentration of the polyethylene glycol used in the methods of the present invention is inversely proportional to the average molecular weight of the polyethylene glycol. For example, in one embodiment, polyethylene glycol having an average molecular weight of 4000 Da is used, at a concentration of 20% w/v. In an alternate embodiment, polyethylene glycol having an average molecular weight of 8000 Da is used, at a concentration of 10% w/v. In an alternate embodiment, polyethylene glycol having an average molecular weight of 20000 Da is used, at a concentration of 4% w/v.

In one embodiment, the precipitated microvesicles are collected by the application of centrifugal force. The centrifugal force is sufficient and applied for a duration sufficient to cause the microvesicles to form a pellet, but insufficient to damage the microvesicles.

The duration and magnitude of the centrifugal force used to precipitate the microvesicles from a biological fluid may vary according to a number of factors readily appreciated by one of ordinary skill in the art, including, for example, the biological fluid, the pH of the biological fluid, the desired purity of the isolated microvesicles, the desired size of the isolated microvesicles, the desired molecular weight of the microvesicles, and the like. In one embodiment, the precipitated microvesicles are collected by the application of a centrifugal force of 10000×g for 60 minutes.

The precipitated microvesicles may be washed with any liquid, provided the liquid does not affect the functional and/or structural integrity of the microvesicles. One of ordinary skill in the art may readily select a suitable liquid. Liquids may be, for example, phosphate buffered saline, cell culture medium, and the like.

In one embodiment, the washing step removes the precipitating agent. In one embodiment, the microvesicles are washed via centrifugal filtration, using a filtration device with a 100 kDa molecular weight cut off.

The isolated microvesicles may be suspended with any liquid, provided the liquid does not affect the functional and/or structural integrity of the microvesicles. One of ordinary skill in the art may readily select a suitable liquid. Liquids may be, for example, phosphate buffered saline, cell culture medium, and the like.

In one embodiment, the isolated microvesicles may be further processed. The further processing may be the isolation of a microvesicle of a specific size. Alternatively, the further processing may be the isolation of microvesicles of a particular size range. Alternatively, the further processing may be the isolation of a microvesicle of a particular molecular weight. Alternatively, the further processing may be the isolation of microvesicles of a particular molecular weight range. Alternatively, the further processing may be the isolation of a microvesicle exhibiting or containing a specific molecule.

In one embodiment, the microvesicles of the present invention are further processed to isolate a preparation of microvesicles having a size of about 2 nm to about 1000 nm as determined by electron microscopy. In an alternate embodiment, the microvesicles of the present invention are further processed to isolate a preparation of microvesicles having a size of about 2 nm to about 500 nm as determined by electron microscopy. In an alternate embodiment, the microvesicles of the present invention are further processed to isolate a preparation of microvesicles having a size of about 2 nm to about 400 nm as determined by electron microscopy. In an alternate embodiment, the microvesicles of the present invention are further processed to isolate a preparation of microvesicles having a size of about 2 nm to about 300 nm as determined by electron microscopy. In an alternate embodiment, the microvesicles of the present invention are further processed to isolate a preparation of microvesicles having a size of about 2 nm to about 200 nm as determined by electron microscopy. In an alternate embodiment, the microvesicles of the present invention are further processed to isolate a preparation of microvesicles having a size of about 2 nm to about 100 nm as determined by electron microscopy. In an alternate embodiment, the microvesicles of the present invention are further processed to isolate a preparation of microvesicles having a size of about 2 nm to about 50 nm as determined by electron microscopy. In an alternate embodiment, the microvesicles of the present invention are further processed to isolate a preparation of microvesicles having a size of about 2 nm to about 20 nm as determined by electron microscopy. In an alternate embodiment, the microvesicles of the present invention are further processed to isolate a preparation of microvesicles having a size of about 2 nm to about 10 nm as determined by electron microscopy.

In one embodiment, the subsequent purification is performed using a method selecting from the group consisting of immunoaffinity, HPLC, tangential flow filtration, phase separation/partitioning, and micro fluidic s.

In one embodiment, the isolated microvesicles are further processed to analyze the molecules exhibited on, or contained within the microvesicles. The molecules analyzed are selected from the group consisting of nucleic acid, carbohydrate, lipid, small molecules, ions, metabolites, protein, and combinations thereof.

Biological fluid comprising cell culture medium conditioned using cultured cells:

In one embodiment, microvesicles are obtained from medium conditioned using cultured cells. Any cultured cell, or population of cells may be used in the methods of the present invention. The cells may be stem cells, primary cells, cell lines, tissue or organ explants, or any combination thereof. The cells may be allogeneic, autologous, or xenogeneic in origin.

In one embodiment, the cells are cells derived from bone-marrow aspirate. In one embodiment, the cells derived from bone marrow aspirate are bone marrow-derived mesenchymal stem cells. In one embodiment, the cells derived from bone marrow aspirate are mononuclear cells. In one embodiment, the cells derived from bone marrow aspirate are a mixture of mononuclear cells and bone marrow-derived mesenchymal stem cells.

In one embodiment, bone marrow-derived mesenchymal stem cells are isolated from bone marrow aspirate by culturing bone marrow aspirate in plastic tissue culture flasks for a period of time of up to about 4 days, followed by a wash to remove the non-adherent cells.

In one embodiment, mononuclear cells are isolated from bone marrow aspirate by low-density centrifugation using a ficoll gradient, and collecting the mononuclear cells at the interface.

In one embodiment, prior to isolation of microvesicles according to the methods of the present invention, the cells are cultured, grown or maintained at an appropriate temperature and gas mixture (typically, 37° C., 5% $CO_2$ for mammalian cells) in a cell incubator. Culture conditions vary widely for each cell type, and are readily determined by one of ordinary skill in the art.

In one embodiment, one, or more than one culture condition is varied. In one embodiment, this variation results in a different phenotype.

In one embodiment, where the cells require serum in their culture medium, to begin the microvesicle isolation procedure, the cell culture medium is supplemented with microvesicle-free serum and then added to the cells to be conditioned. The microvesicles are collected from the conditioned cell culture medium. Serum may be depleted by any suitable method, such as, for example, ultracentrifugation, filtration, precipitation, and the like. The choice of medium, serum concentration, and culture conditions are influenced by a variety of factors readily appreciated by one of ordinary skill in the art, including, for example, the cell type being cultured, the desired purity of the microvesicles, the desired phenotype of the cultured cell, and the like. In one embodiment, the cell culture medium that is conditioned for the microvesicle isolation procedure is the same type of cell culture medium that the cells were grown in, prior to the microvesicle isolation procedure.

In one embodiment, to begin the microvesicle isolation procedure, the cell culture medium is removed, and serum-free medium is added to the cells to be conditioned. The microvesicles are then collected from the conditioned serum free medium. The choice of medium, and culture conditions are influenced by a variety of factors readily appreciated by one of ordinary skill in the art, including, for example, the cell type being cultured, the desired purity of the microvesicles, the desired phenotype of the cultured cell, and the like. In one embodiment, the serum-free medium is supplemented with at least one additional factor that promotes or enhances the survival of the cells in the serum free medium. Such factor may, for example, provide trophic support to the cells, inhibit, or prevent apoptosis of the cells.

The cells are cultured in the culture medium for a period of time sufficient to allow the cells to secrete microvesicles into the culture medium. The period of time sufficient to allow the cells to secrete microvesicles into the culture medium is influenced by a variety of factors readily appreciated by one of ordinary skill in the art, including, for example, the cell type being cultured, the desired purity of the microvesicles, the desired phenotype of the cultured cell, desired yield of microvesicles, and the like.

The microvesicles are then removed from the culture medium by the methods of the present invention.

In one embodiment, prior to the microvesicle isolation procedure, the cells are treated with at least one agent selected from the group consisting of an anti-inflammatory compound, an anti-apoptotic compound, an inhibitor of fibrosis, a compound that is capable of enhancing angiogenesis, an immunosuppressive compound, a compound that promotes survival of the cells, a chemotherapeutic, a compound capable of enhancing cellular migration, a neurogenic compound, and a growth factor. In one embodiment, while the cells are being cultured in the medium from which the microvesicles are collected, the cells are treated with at least one agent selected from the group consisting of an anti-inflammatory compound, an anti-apoptotic compound, an inhibitor of fibrosis, a compound that is capable of enhancing angiogenesis, an immunosuppressive compound, a compound that promotes survival of the cells, and a growth factor.

In one embodiment, the anti-inflammatory compound may be selected from the compounds disclosed in U.S. Pat. No. 6,509,369.

In one embodiment, the anti-apoptotic compound may be selected from the compounds disclosed in U.S. Pat. No. 6,793,945.

In one embodiment, the inhibitor of fibrosis may be selected from the compounds disclosed in U.S. Pat. No. 6,331,298.

In one embodiment, the compound that is capable of enhancing angiogenesis may be selected from the compounds disclosed in U. S. Patent Application 2004/0220393 or U. S. Patent Application 2004/0209901.

In one embodiment, the immunosuppressive compound may be selected from the compounds disclosed in U. S. Patent Application 2004/0171623.

In one embodiment, the compound that promotes survival of the cells may be selected from the compounds disclosed in U. S. Patent Application 2010/0104542.

In one embodiment, the growth factor may be at least one molecule selected from the group consisting of members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, -AB, and -BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-1 (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, and MAPK inhibitors, such as, for example, compounds disclosed in U. S. Patent Application 2004/0209901 and U. S. Patent Application 2004/0132729.

In one embodiment, microvesicles are isolated from a biological fluid comprising cell culture medium conditioned using a culture of bone marrow-derived mesenchymal stem cells comprising the steps of:

a) obtaining a population of bone marrow-derived mesenchymal stem cells and seeding flasks at a 1:4 dilution of cells, b) culturing the cells in medium until the cells are 80 to 90% confluent, c) removing and clarifying the medium to remove cellular debris, d) precipitating the microvesicles by adding a precipitating agent to the clarified culture medium, e) collecting the precipitated microvesicles and washing the material to remove the precipitating agent, and f) suspending the washed microvesicles in a solution for storage or subsequent use.

In one embodiment, microvesicles are isolated from a biological fluid comprising cell culture medium conditioned using a culture of bone marrow-derived mononuclear cells comprising the steps of:

a) obtaining a population of bone marrow-derived mononuclear cells and seeding flasks at a 1:4 dilution of cells, b) culturing the cells in medium until the cells are 80 to 90% confluent, c) removing and clarifying the medium to remove cellular debris, d) precipitating the microvesicles by adding a precipitating agent to the clarified culture medium, e) collecting the precipitated microvesicles and washing the material to remove the precipitating agent, and f) suspending the washed microvesicles in a solution for storage or subsequent use.

In one embodiment, the bone marrow-derived mesenchymal stem cells are cultured in medium comprising $\alpha$-MEM supplemented with 20% fetal bovine serum and 1% penicillin/streptomycin/glutamine at 37° C. in 95% humidified air and 5% $CO_2$.

In one embodiment, the bone marrow-derived mononuclear cells are cultured in medium comprising $\alpha$-MEM supplemented with 20% fetal bovine serum and 1% penicillin/streptomycin/glutamine at 37° C. in 95% humidified air and 5% $CO_2$.

In one embodiment, the medium is clarified by centrifugation.

In one embodiment, the precipitating agent is polyethylene glycol having an average molecular weight of 6000. In one embodiment, the polyethylene glycol is used at a concentration of about 8.5 w/v %. In one embodiment, the polyethylene glycol is diluted in a sodium chloride solution having a final concentration of 0.4 M.

In one embodiment, the precipitated microvesicles are collected by centrifugation.

In one embodiment, the isolated microvesicles are washed via centrifugal filtration, using a membrane with a 100 kDa molecular weight cut-off, using phosphate buffered saline.

Biological fluid comprising plasma: In one embodiment, microvesicles are obtained from plasma. The plasma may be obtained from a healthy individual, or, alternatively, from an individual with a particular disease phenotype.

In one embodiment, microvesicles are isolated from a biological fluid comprising plasma comprising the steps of:

a) obtaining plasma and diluting the plasma with cell culture medium, b) precipitating the microvesicles by adding a precipitating agent to the diluted plasma, c) collecting the precipitated microvesicles and washing the material to remove the precipitating agent, and d) suspending the washed microvesicles in a solution for storage or subsequent use.

In one embodiment, the plasma is diluted 1:10 with culture medium. In one embodiment, the culture medium is $\alpha$-MEM.

In one embodiment, the precipitating agent is polyethylene glycol having an average molecular weight of 6000. In one embodiment, the polyethylene glycol is used at a concentration of about 8.5 w/v %. In one embodiment, the polyethylene glycol is diluted in a sodium chloride solution having a final concentration of 0.4 M.

In one embodiment, the precipitated microvesicles are collected by centrifugation.

In one embodiment, the isolated microvesicles are washed via centrifugal filtration, using a membrane with a 100 kDa molecular weight cut-off, using phosphate buffered saline.

Biological fluid comprising bone marrow aspirate: In one embodiment, microvesicles are obtained from bone marrow aspirate. In one embodiment, microvesicles are obtained from the cellular fraction of the bone marrow aspirate. In one embodiment, microvesicles are obtained from the acellular fraction of the bone marrow aspirate.

In one embodiment, microvesicles are obtained from cells cultured from bone marrow aspirate. In one embodiment, the cells cultured from bone marrow aspirate are used to condition cell culture medium, from which the microvesicles are isolated.

In one embodiment, microvesicles are isolated from a biological fluid comprising bone marrow aspirate comprising the steps of:

a) obtaining bone marrow aspirate and separating the bone marrow aspirate into an acellular portion and a cellular portion, b) diluting the acellular portion, c) clarifying the diluted acellular portion to remove cellular debris, d) precipitating the microvesicles in the acellular portion by adding a precipitating agent to the diluted acellular portion, e) collecting the precipitated microvesicles and washing the material to remove the precipitating agent, and f) suspending the washed microvesicles in a solution for storage or subsequent use.

In one embodiment, the acellular portion is diluted 1:10 with culture medium.

In one embodiment, the culture medium is $\alpha$-MEM.

In one embodiment, the diluted acellular portion is clarified by centrifugation.

In one embodiment, the precipitating agent is polyethylene glycol having an average molecular weight of 6000. In one embodiment, the polyethylene glycol is used at a concentration of about 8.5 w/v %. In one embodiment, the polyethylene glycol is diluted in a sodium chloride solution having a final concentration of 0.4 M.

In one embodiment, the precipitated microvesicles are collected by centrifugation.

In one embodiment, the isolated microvesicles are washed via centrifugal filtration, using a membrane with a 100 kDa molecular weight cut-off, using phosphate buffered saline.

In one embodiment the cellular portion is further processed to isolate and collect cells. In one embodiment, the cellular portion is further processed to isolate and collect bone marrow-derived mesenchymal stem cells. In one embodiment, the cellular portion is further processed to isolate and collect bone marrow-derived mononuclear cells. In one embodiment, the cellular portion is used to condition medium, from which microvesicles may later be derived.

In one embodiment, microvesicles are isolated from the cellular portion. The cellular portion may be incubated for a period of time prior to the isolation of the microvesicles. Alternatively, the microvesicles may be isolated from the cellular portion immediately after the cellular portion is collected.

In one embodiment, the cellular portion is also treated with at least one agent selected from the group consisting of an anti-inflammatory compound, an anti-apoptotic compound, an inhibitor of fibrosis, a compound that is capable of enhancing angiogenesis, an immunosuppressive compound, a compound that promotes survival of the cells, a chemotherapeutic, a compound capable of enhancing cellular migration, a neurogenic compound, and a growth factor.

In one embodiment, the anti-inflammatory compound may be selected from the compounds disclosed in U.S. Pat. No. 6,509,369.

In one embodiment, the anti-apoptotic compound may be selected from the compounds disclosed in U.S. Pat. No. 6,793,945.

In one embodiment, the inhibitor of fibrosis may be selected from the compounds disclosed in U.S. Pat. No. 6,331,298.

In one embodiment, the compound that is capable of enhancing angiogenesis may be selected from the compounds disclosed in U. S. Patent Application 2004/0220393 or U. S. Patent Application 2004/0209901.

In one embodiment, the immunosuppressive compound may be selected from the compounds disclosed in U. S. Patent Application 2004/0171623.

In one embodiment, the compound that promotes survival of the cells may be selected from the compounds disclosed in U. S. Patent Application 2010/0104542.

In one embodiment, the growth factor may be at least one molecule selected from the group consisting of members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, -AB, and -BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-1 (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, bio-logical peptides containing cell- and heparin-binding domains of adhesive extracellular matrix proteins such as fibronectin and vitronectin, and MAPK inhibitors, such as, for example, compounds disclosed in U. S. Patent Application 2004/0209901 and U. S. Patent Application 2004/0132729. In one embodiment, the cellular portion is cultured under hypoxic conditions. In one embodiment, the cellular portion is heat-shocked.

Biological fluid comprising urine: In one embodiment, microvesicles are obtained from urine. The urine may be obtained from a healthy individual, or, alternatively, from an individual with a particular disease phenotype.

In one embodiment, microvesicles are isolated from a biological fluid comprising urine comprising the steps of:

a) obtaining a urine sample, b) clarifying the urine to remove cellular debris, c) precipitating the microvesicles by adding a precipitating agent to the clarified urine, d) collecting the precipitated microvesicles and washing the material to remove the precipitating agent, and e) suspending the washed microvesicles in a solution for storage or subsequent use.

In one embodiment, the urine is clarified by centrifugation.

In one embodiment, the precipitating agent is polyethylene glycol having an average molecular weight of 6000. In one embodiment, the polyethylene glycol is used at a concentration of about 8.5 w/v %. In one embodiment, the polyethylene glycol is diluted in a sodium chloride solution having a final concentration of 0.4 M.

In one embodiment, the precipitated microvesicles are collected by centrifugation.

In one embodiment, the isolated microvesicles are washed via centrifugal filtration, using a membrane with a 100 kDa molecular weight cut-off, using phosphate buffered saline.

In an alternate embodiment of the present invention, the biological fluids are clarified by filtration. In an alternate embodiment, the precipitated microvesicles are collected by filtration. In an alternate embodiment, the biological fluids are clarified and the precipitated microvesicles are collected by filtration. In certain embodiments, filtration of either the biological fluid, and/or the precipitated microvesicles required the application of an external force. The external force may be gravity, either normal gravity or centrifugal force. Alternatively, the external force may be suction.

In one embodiment, the present embodiment provides an apparatus to facilitate the clarification of the biological fluid by filtration. In one embodiment, the present invention provides an apparatus to facilitate collection of the precipitated microvesicles by filtration. In one embodiment, the present invention provides an apparatus that facilitates the clarification of the biological fluid and the collection of the precipitated microvesicles by filtration. In one embodiment, the apparatus also washes the microvesicles.

Figure 4:
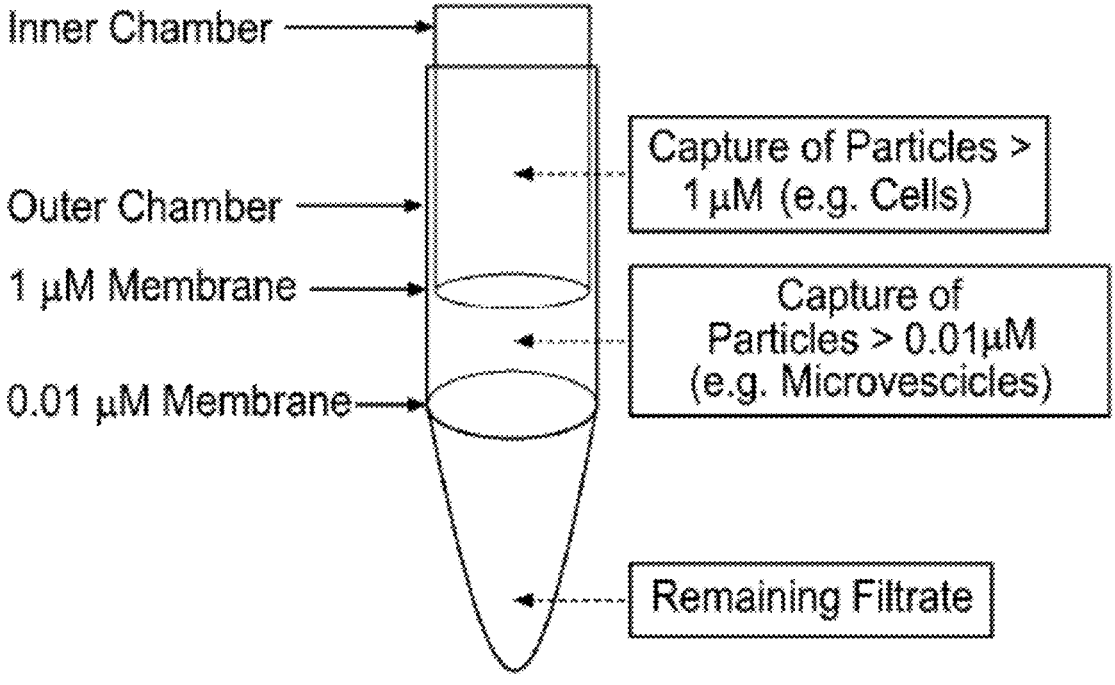
FIG. 4 shows one embodiment of an apparatus of the present invention that facilitates the clarification of the biological fluid and the collection of the precipitated microvesicles by filtration.

In one embodiment, the apparatus is the apparatus shown in FIG. 4. In this embodiment, the biological fluid is added to the inner chamber. The inner chamber has a first filter with a pore size that enables the microvesicles to pass, while retaining any particle with a size greater than a microvesicle in the inner chamber. In one embodiment, the pore size of the filter of the inner chamber is 1 μm. In this embodiment, when the biological fluid passed from the inner chamber through the filter, particles greater than 1 μm are retained in the inner chamber, and all other particles collect in the region between the bottom of the inner chamber and a second filter.

The second filter has a pore size that does not allow microvesicles to pass. In one embodiment, the pore size of the second filter of the inner chamber is 0.01 μm. In this embodiment, when the biological fluid passed through the second filter, the microvesicles are retained in the region between the bottom of the inner chamber and the second filter, and all remaining particles and fluid collect in the bottom of the apparatus.

One of ordinary skill in the art can readily appreciate that the apparatus can have more than two filters, of varying pore sizes to select for microvesicles of desired sizes, for example.

In one embodiment, a precipitating agent is added to the biological fluid in the inner chamber. In one embodiment, a precipitating agent is added to the filtrate after it has passed through the first filter. The filter membranes utilized by the apparatus of the present invention may be made from any suitable material, provided the filter membrane does not react with the biological fluid, or bind with components within the biological fluid. For example, the filter membranes may be made from a low bind material, such as, for example, polyethersulfone, nylon6, polytetrafluoroethylene, polypropylene, zeta modified glass microfiber, cellulose nitrate, cellulose acetate, polyvinylidene fluoride, regenerated cellulose.

The Microvesicles of the Present Invention

In one embodiment, the microvesicles of the present invention have a size of about 2 nm to about 5000 nm as determined by electron microscopy. In an alternate embodiment, the microvesicles of the present invention have a size of about 2 nm to about 1000 nm as determined by electron microscopy. In an alternate embodiment, the microvesicles of the present invention have a size of about 2 nm to about 500 nm as determined by electron microscopy. In an alternate embodiment, the microvesicles of the present invention have a size of about 2 nm to about 400 nm as determined by electron microscopy. In an alternate embodiment, the microvesicles of the present invention have a size of about 2 nm to about 300 nm as determined by electron microscopy. In an alternate embodiment, the microvesicles of the present invention have a size of about 2 nm to about 200 nm as determined by electron microscopy. In an alternate embodiment, the microvesicles of the present invention have a size of about 2 nm to about 100 nm as determined by electron microscopy. In an alternate embodiment, the microvesicles of the present invention have a size of about 2 nm to about 50 nm as determined by electron microscopy. In an alternate embodiment, the microvesicles of the present invention have a size of about 2 nm to about 20 nm as determined by electron microscopy. In an alternate embodiment, the microvesicles of the present invention have a size of about 2 nm to about 10 nm as determined by electron microscopy.

In one embodiment, the microvesicles of the present invention have a molecular weight of at least 100 kDa.

Microvesicles isolated according to the methods of the present invention may be used for therapies. Alternatively, microvesicles isolated according to the methods of the present invention may be used for diagnostic tests. Alternatively, the microvesicles of the present invention may be used to alter or engineer cells or tissues. In the case where the microvesicles of the present invention are used to alter or engineer cells or tissues, the microvesicles may be loaded, labeled with RNA, DNA, lipids, carbohydrates, protein, drugs, small molecules, metabolites, or combinations thereof, that will alter or engineer a cell or tissue. Alternatively, the microvesicles may be isolated from cells or tissues that express and/or contain the RNA, DNA, lipids, carbohydrates, protein, drugs, small molecules, metabolites, or combinations thereof.

Use of the Microvesicles of the Present Invention in Diagnostic Tests

The microvesicles of the present invention can be used in a diagnostic test that detects biomarkers that identify particular phenotypes such as, for example, a condition or disease, or the stage or progression of a disease. Biomarkers or markers from cell-of-origin specific microvesicles can be used to determine treatment regimens for diseases, conditions, disease stages, and stages of a condition, and can also be used to determine treatment efficacy. Markers from cell-of-origin specific microvesicles can also be used to identify conditions of diseases of unknown origin.

As used herein, the term "biomarker" refers to an indicator of a biological state. It is a characteristic that is objectively measured and evaluated as an indicator of normal biological processes, pathogenic processes, or pharmacologic responses to a therapeutic intervention. One or more biomarkers of microvesicle can be assessed for characterizing a phenotype. The biomarker can be a metabolite, a nucleic acid, peptide, protein, lipid, antigen, carbohydrate or proteoglycan, such as DNA or RNA. The RNA can be mRNA, miRNA, snoRNA, snRNA, rRNAs, tRNAs, siRNA, hnRNA, or shRNA.

A phenotype in a subject can be characterized by obtaining a biological sample from the subject and analyzing one or more microvesicles from the sample. For example, characterizing a phenotype for a subject or individual may include detecting a disease or condition (including presymptomatic early stage detecting), determining the prognosis, diagnosis, or theranosis of a disease or condition, or determining the stage or progression of a disease or condition. Characterizing a phenotype can also include identifying appropriate treatments or treatment efficacy for specific diseases, conditions, disease stages and condition stages, predictions and likelihood analysis of disease progression, particularly disease recurrence, metastatic spread or disease relapse. A phenotype can also be a clinically distinct type or subtype of a condition or disease, such as a cancer or tumor. Phenotype determination can also be a determination of a physiological condition, or an assessment of organ distress or organ rejection, such as post-transplantation. The products and processes described herein allow assessment of a subject on an individual basis, which can provide benefits of more efficient and economical decisions in treatment.

The phenotype can be any phenotype listed in U.S. Pat. No. 7,897,356. The phenotype can be a tumor, neoplasm, or cancer. A cancer detected or assessed by products or processes described herein includes, but is not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, and Burkitt's lymphoma. The phenotype may also be a premalignant condition, such as Barrett's Esophagus.

The phenotype can also be an inflammatory disease, immune disease, or autoimmune disease. For example, the disease may be inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Erythematosis (SLE), Hashimoto's Thyroiditis, Grave's disease, Ankylosing Spondylitis Sjorgen's Disease, CREST syndrome, Scleroderma, Rheumatic Disease, organ rejection, graft versus host disease, Primary Sclerosing Cholangitis, or sepsis. In certain exemplary embodiments, the disease is EB, e.g., RDEB and/or DDEB, junctional EB, EB simplex and/or acquired forms of EB.

The phenotype can also be a cardiovascular disease, such as atherosclerosis, congestive heart failure, vulnerable plaque, stroke, or ischemia. The cardiovascular disease or condition can be high blood pressure, stenosis, vessel occlusion or a thrombotic event.

The phenotype can also be a neurological disease, such as Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neuropsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The phenotype may also be a condition such as fibromyalgia, chronic neuropathic pain, or peripheral neuropathic pain.

The phenotype may also be an infectious disease, such as a bacterial, viral or yeast infection. For example, the disease or condition may be Whipple's Disease, Prion Disease, cirrhosis, methicillin-resistant *Staphylococcus aureus*, HIV, hepatitis, syphilis, meningitis, malaria, tuberculosis, or influenza. Viral proteins, such as HIV or HCV-like particles can be assessed in an exosome, to characterize a viral condition.

The phenotype can also be a perinatal or pregnancy related condition (e.g., preeclampsia or preterm birth), metabolic disease or condition, such as a metabolic disease or condition associated with iron metabolism. The metabolic disease or condition can also be diabetes, inflammation, or a perinatal condition.

The phenotype may be detected via any suitable assay method, such as, for example, western blots, ELISA, PCR, and the like. The assay methods may be combined to perform multiplexed analysis of more than one phenotype. Examples of assay methods that may be applied to the microvesicles of the present invention are disclosed in PCT Applications WO2009092386A3 and WO2012108842A1.

In the case where the biomarker is RNA, the RNA may be isolated from the microvesicles of the present invention by the methods disclosed in U.S. Pat. No. 8,021,847.

In one embodiment, the microvesicles of the present invention are utilized in a diagnostic test for the diseases disclosed in U.S. Pat. No. 7,897,356.

In one embodiment, the microvesicles of the present invention are utilized in a diagnostic test for cancer according to the methods disclosed in U.S. Pat. No. 8,211,653.

In one embodiment, the microvesicles of the present invention are utilized in a diagnostic test for cancer according to the methods disclosed in U.S. Pat. No. 8,216,784.

In one embodiment, the microvesicles of the present invention are utilized in a diagnostic test for prostate cancer according to the methods disclosed in U.S. Pat. No. 8,278,059. In one embodiment, the microvesicles of the present invention are utilized in a diagnostic test for the prognosis for cancer survival according to the methods disclosed in U.S. Pat. No. 8,343,725.

In one embodiment, the microvesicles of the present invention are utilized in a diagnostic test for the prognosis for cancer survival according to the methods disclosed in U.S. Pat. No. 8,349,568.

In one embodiment, the microvesicles of the present invention are utilized in a diagnostic test for acute lymphomic leukemia according to the methods disclosed in U.S. Pat. No. 8,349,560.

In one embodiment, the microvesicles of the present invention are utilized in a diagnostic test for acute lymphomic leukemia according to the methods disclosed in U.S. Pat. No. 8,349,561.

In one embodiment, the microvesicles of the present invention are utilized in a diagnostic test for hepatitis C virus. In one embodiment, hepatitis C viral RNA is extracted from the microvesicles of the present invention according to the methods described in U.S. Pat. No. 7,807,438 to test for the presence of hepatitis C virus in a patient.

In one embodiment, the microvesicles of the present invention are utilized in a diagnostic test for determining the response of a patient to cancer therapy according to the methods disclosed in U.S. Pat. No. 8,349,574.

In one embodiment, the microvesicles of the present invention are utilized in a diagnostic test for diagnosing malignant tumors according to the methods disclosed in U.S. Patent Application US20120058492A1.

In one embodiment, the microvesicles of the present invention are utilized in a diagnostic test for diagnosing cancer or adverse pregnancy outcome according to the methods disclosed in U.S. Patent Application US20120238467A1.

In one embodiment, the microvesicles of the present invention are utilized in a diagnostic test for HIV in urine according to the methods disclosed in U.S. Patent Application US20120214151A1. In one embodiment, the microvesicles of the present invention are utilized in a diagnostic test for cardiovascular events according to the methods disclosed in U.S. Patent Application US20120309041A1.

In one embodiment, the microvesicles of the present invention are utilized in a diagnostic test for cardiovascular events according to the methods disclosed in PCT Application WO2012110099A1.

In one embodiment, the microvesicles of the present invention are utilized in a diagnostic test for cardiovascular events according to the methods disclosed in PCT Application WO2012126531A1.

In one embodiment, the microvesicles of the present invention are utilized in a diagnostic test for cardiovascular events according to the methods disclosed in PCT Application WO2013110253A3.

In one embodiment, the microvesicles of the present invention are utilized in a diagnostic test for melanoma according to the methods disclosed in PCT Application WO2012135844A2.

In one embodiment, the microvesicles of the present invention are utilized in a diagnostic test for metastatic melanoma by testing microvesicles isolated according to the methods of the present invention for the presence of the biomarker BRAF. The presence of BRAF may be determined via western blot, or, alternatively, by PCR. In one embodiment, the metastatic melanoma test is capable of detecting wild type and malignant BRAF. In one embodiment, the metastatic melanoma test is capable of detecting splice variants of the malignant BRAF.

Figure 3:
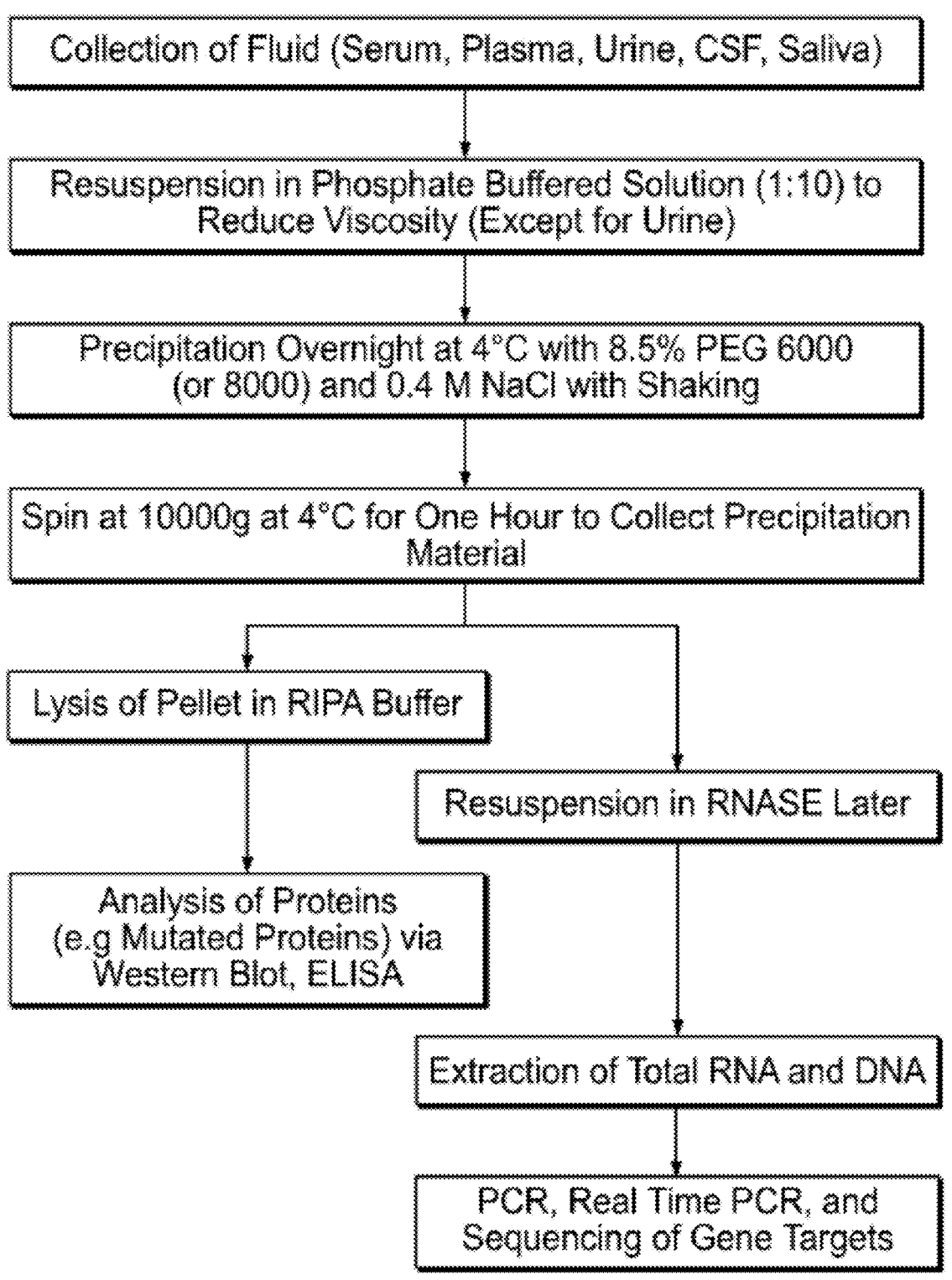
FIG. 3 shows an alternate embodiment of a microvesicle isolation method of the present invention.

In one embodiment, the microvesicles that are utilized in the diagnostic test for metastatic melanoma are isolated using a method comprising the steps outlined in FIG. 3.

In one embodiment, microvesicles are obtained from a patient wishing to be diagnosed for the presence of metastatic melanoma. In one embodiment, the microvesicles are obtained from the patient's plasma.

In one embodiment, the presence of metastatic melanoma is determined via PCR, using one of the two primer sets below:

```
Sequence 1:
Forward:
                              (SEQ ID NO: 1)
AGACCTCACAGTAAAAATAGGTGA Reverse:
                              (SEQ ID NO: 2)
CTGATGGGACCCACTCCATC Amplicon length: 70

Sequence 2:
Forward:
                              (SEQ ID NO: 3)
GAAGACCTCACAGTAAAAATAGGTG Reverse:
                              (SEQ ID NO: 4)
CTGATGGGACCCACTCCATC Amplicon length: 82
```

In another embodiment, the presence of metastatic melanoma is determined via western blot, using the mouse anti-BRAF V600E antibody (NewEast Biosciences, Malvern, PA).

Use of the Microvesicles of the Present Invention in Therapies

The microvesicles of the present invention can be used as a therapy to treat a disease.

In one embodiment, the microvesicles of the present invention are used as vaccines according to the methods described in U.S. Patent Application US20030198642A1.

In one embodiment, the microvesicles of the present invention are used to modulate or suppress a patient's immune response according to the methods described in U.S. Patent Application US20060116321A1.

In one embodiment, the microvesicles of the present invention are used to modulate or suppress a patient's immune response according to the methods described in PCT Patent Application WO06007529A3.

In one embodiment, the microvesicles of the present invention are used to modulate or suppress a patient's immune response according to the methods described in PCT Patent Application WO2007103572A3.

In one embodiment, the microvesicles of the present invention are used to modulate or suppress a patient's immune response according to the methods described in U.S. Pat. No. 8,288,172.

In one embodiment, the microvesicles of the present invention are used as a therapy for cancer according to the methods described in PCT Patent Application WO2011000551A1. In one embodiment, the microvesicles of the present invention are used as a therapy for cancer or an inflammatory disease according to the methods described in U.S. Patent Application US20120315324A1.

In one embodiment, the microvesicles of the present invention are used as a therapy for vascular injury according to the methods described in U.S. Pat. No. 8,343,485.

In one embodiment, the microvesicles of the present invention are used to deliver molecules to cells. The delivery of molecules may be useful in treating or preventing a disease. In one embodiment, the delivery is according to the methods described in PCT Application WO04014954A1. In an alternate embodiment, the delivery is according to the methods described in PCT Application WO2007126386A1. In an alternate embodiment, the delivery is according to the methods described in PCT Application WO2009115561A1. In an alternate embodiment, the delivery is according to the methods described in PCT Application WO2010119256A1.

In one embodiment, the microvesicles of the present invention are used to promote or enhance wound healing. In one embodiment, the wound is a full-thickness burn. In one embodiment, the wound is a second-degree burn.

In one embodiment, the microvesicles of the present invention are used to promote or enhance angiogenesis in a patient.

In one embodiment, the microvesicles of the present invention are used to promote or enhance neuronal regeneration in a patient.

In one embodiment, the microvesicles of the present invention are used to reduce scar formation in a patient.

In one embodiment, the microvesicles of the present invention are used to reduce wrinkle formation in the skin of a patient.

In one embodiment, the microvesicles of the present invention are used to orchestrate complex tissue regeneration in a patient.

In one embodiment, the present invention provides an isolated preparation of microvesicles that can promote functional regeneration and organization of complex tissue structures. In one embodiment the present invention provides an isolated preparation of microvesicles that can regenerate hematopoietic tissue in a patient with aplastic anemia. In one embodiment the present invention provides an isolated preparation of microvesicles that can regenerate at least one tissue in a patient with diseased, damages or missing skin selected from the group consisting of: epithelial tissue, stromal tissue, nerve tissue, vascular tissue and adnexal structures. In one embodiment, the present invention provides an isolated preparation of microvesicles that can regenerate tissue and/or cells from all three germ layers.

In one embodiment, the present invention provides an isolated preparation of microvesicles that is used to modulate the immune system of a patient.

In one embodiment, the present invention provides an isolated preparation of microvesicles that is used to alleviate one or more symptoms of EB (e.g., RDEB and/or DDEB, junctional EB, EB simplex and/or acquired forms of EB) in a patient.

In another embodiment, the present invention provides an isolated preparation of microvesicles that is used to increase collagen VII expression in a patient having EB (e.g., RDEB and/or DDEB, junctional EB, EB simplex and/or acquired forms of EB).

In one embodiment, the present invention provides an isolated preparation of microvesicles that enhances the survival of tissue or cells that is transplanted into a patient. In one embodiment, the patient is treated with the isolated preparation of microvesicles prior to receiving the transplanted tissue or cells. In an alternate embodiment, the patient is treated with the isolated preparation of microvesicles after receiving the transplanted tissue or cells. In an alternate embodiment, the tissue or cells is treated with the isolated preparation of microvesicles. In one embodiment, the tissue or cells is treated with the isolated preparation of microvesicles prior to transplantation.

In one embodiment, the present invention provides an isolated preparation of microvesicles containing at least one molecule selected from the group consisting of RNA, DNA, lipid, carbohydrate, metabolite, protein, and combination thereof from a host cell. In one embodiment, the host cell is engineered to express at least one molecule selected from the group consisting of RNA, DNA, lipid, carbohydrate, metabolite, protein, and combination thereof. In one embodiment, the isolated preparation of microvesicles containing at least one molecule selected from the group consisting of RNA, DNA, lipid, carbohydrate, metabolite, protein, and combination thereof from a host cell is used as a therapeutic agent.

Use of the Microvesicles of the Present Invention in Therapies

For therapeutic use, MVs are preferably combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Accordingly, EV compositions of the present invention can comprise at least one of any suitable excipients, such as, but not limited to, diluent, binder, stabilizer, buffers, salts, lipophilic solvents, preservative, adjuvant or the like. Pharmaceutically acceptable excipients are preferred. Non-limiting examples of, and methods of preparing such sterile solutions are well known in the art, such as, but not limited to, those described in Gennaro, Ed., Remington's Pharmaceutical Sciences, 18th Edition, Mack Publishing Co. (Easton, Pa.) 1990. Pharmaceutically acceptable carriers can be routinely selected that are suitable for the mode of administration, solubility and/or stability of EV composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody molecule components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

EV compositions can also include a buffer or a pH adjusting agent; typically, the buffer is a salt prepared from an organic acid or base. Representative buffers include organic acid salts such as salts of citric acid, acetic acid, ascorbic acid, gluconic acid, carbonic acid, tartaric acid, succinic acid, or phthalic acid; Tris, tromethamine hydrochloride, or phosphate buffers.

Additionally, EV compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the antibody molecule compositions according to the invention are known in the art, e.g., as listed in "Remington: The Science & Practice of Pharmacy," 19th ed., Williams & Williams, (1995), and in the "Physician's Desk Reference," 52nd ed., Medical Economics, Montvale, N.J. (1998). Preferred carrier or excipient materials are carbohydrates (e.g., saccharides and alditols) and buffers (e.g., citrate) or polymeric agents.

The present invention provides for stable compositions, comprising MVs in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, or 1.0%), 0.1-3% benzyl alcohol (e.g., 0.5, 0.9, 1.1, 1.5, 1.9, 2.0, or 2.5%), 0.001-0.5% thimerosal (e.g., 0.005 or 0.01%), 0.001-2.0% phenol (e.g., 0.05, 0.25, 0.28, 0.5, 0.9, or 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, or 1.0%), and the like.

Pharmaceutical compositions containing MVs as disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, and rectal administration. A preferred route of administration for MVs is topical administration. Useful formulations can be prepared by methods known in the pharmaceutical art. For example, see Remington's Pharmaceutical Sciences (1990) supra. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations are preferably sterile. Sterilization can be accomplished by any suitable method, e.g., filtration through sterile filtration membranes. Where the composition is lyophilized, filter sterilization can be conducted prior to or following lyophilization and reconstitution.

The compositions of this invention may be in a variety of forms. These include, for example, liquid, semi-solid and solid dosage forms, such as liquid solutions (e.g., injectable and infusible solutions), dispersions or suspensions, and liposomes. The preferred form depends on the intended mode of administration and therapeutic application. Typical preferred compositions are in the form of injectable or infusible solutions. The preferred mode of administration is parenteral (e.g., intravenous, subcutaneous, intraocular, intraperitoneal, intramuscular). In a preferred embodiment, the preparation is administered by intravenous infusion or injection. In another preferred embodiment, the preparation is administered by intramuscular or subcutaneous injection.

The phrases "parenteral administration" and "administered parenterally" as used herein means modes of administration other than enteral and topical administration, usually by injection, and includes, without limitation, intravenous, intramuscular, subcutaneous, intraarterial, intrathecal, intracapsular, intraorbital, intravitreous, intracardiac, intradermal, intraperitoneal, transtracheal, inhaled, subcutaneous, subcuticular, intraarticular, subcapsular, subarachnoid, intraspinal, epidural and intrasternal injection and infusion.

The present invention provides a kit, comprising packaging material and at least one vial comprising a solution of MVs with the prescribed buffers and/or preservatives, optionally in an aqueous diluent. The aqueous diluent optionally further comprises a pharmaceutically acceptable preservative. Preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer can be added to provide improved pH control. The formulations can cover a wide range of pHs, such as from about pH 4.0 to about pH 10.0, from about pH 5.0 to about pH 9.0, or about pH 6.0 to about pH 8.0.

Other additives, such as a pharmaceutically acceptable solubilizers like TWEEN 20 (polyoxyethylene (20) sorbitan monolaurate), TWEEN 40 (polyoxyethylene (20) sorbitan monopalmitate), TWEEN 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block copolymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

Various delivery systems can be used to administer MVs to a subject. In certain exemplary embodiments, administration of MVs is topical, optionally with the addition of a dressing, bandage, medical tape, pad, gauze or the like. Suitable dressings to aid in topical delivery are well-known in the art and are commercially available. In other embodiments, MVs are administered by pulmonary delivery, e.g., by intranasal administration, or by oral inhalative administration. Pulmonary delivery may be achieved via a syringe or an inhaler device (e.g., a nebulizer, a pressurized metered-dose inhaler, a multi-dose liquid inhaler, a thermal vaporization aerosol device, a dry powder inhaler or the like). Suitable methods for pulmonary delivery are well-known in the art and are commercially available.

Any of the formulations described above can be stored in a liquid or frozen form and can be optionally subjected to a preservation process.

In certain exemplary embodiments of the invention, EVs described herein are used to deliver one or more bioactive agents to a target cell. The term "bioactive agent" is intended to include, but is not limited to, proteins (e.g., non-membrane-bound proteins), peptides (e.g., non-membrane-bound peptides), transcription factors, nucleic acids and the like, that are expressed in a cell and/or in a cellular fluid and are added during the purification and/or preparation of EVs described herein, and/or pharmaceutical compounds, proteins (e.g., non-membrane-bound proteins), peptides (e.g., non-membrane-bound peptides), transcription factors, nucleic acids and the like, that EVs described herein are exposed to during one or more purification and/or preparation steps described herein. In certain embodiments, a bioactive agent is a collagen VII protein, a collagen VII mRNA, a STAT3 signalling activator (e.g., an interferon, epidermal growth factor, interleukin-5, interleukin-6, a MAP kinase, a c-src non-receptor tyrosine kinase or another molecule that phosphorylates and/or otherwise activates STAT3) and/or a canonical Wnt activator (see, e.g., McBride et al. (2017) Transgenic expression of a canonical Wnt inhibitor, kallistatin, is associated with decreased circulating CD19+B lymphocytes in the peripheral blood. International Journal of Hematology, 1-10. DOI: 10.1007/s12185-017-2205-5, incorporated herein by reference in its entirety). In other embodiments, a bioactive agent is one or more pharmaceutical compounds known in the art.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting. All patents, patent applications and references described herein are incorporated by reference in their entireties for all purposes.

EXAMPLES

Figure 1:
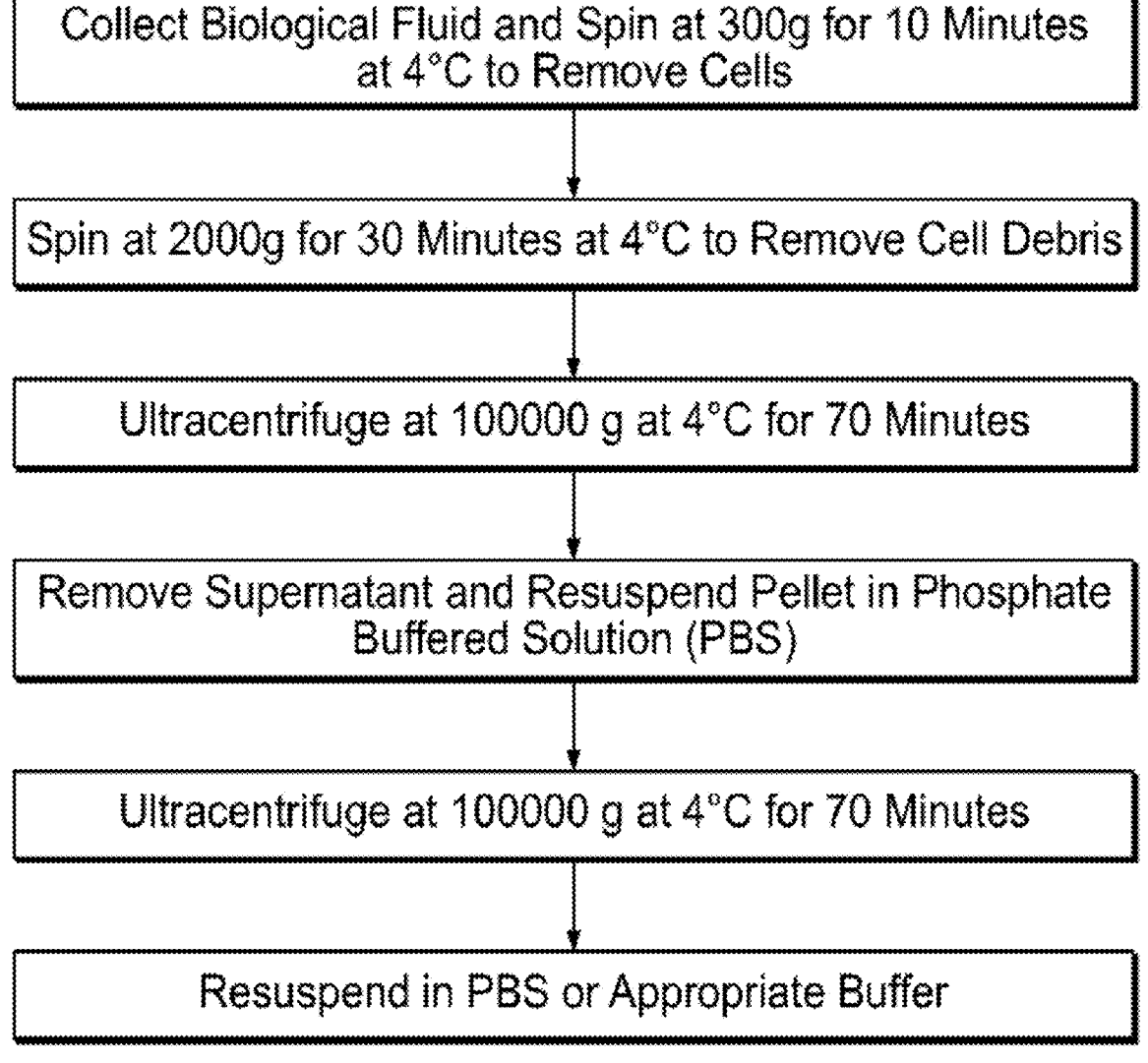
FIG. 1 shows a schematic outline of a protocol used to isolate microvesicles by ultracentrifugation.

Example 1: Isolation of Microvesicles from Cell Culture Medium by Ultracentrifugation This example illustrates the typical method by which microvesicles are isolated from cell culture medium, or any biological fluid. An outline of the method to isolate microvesicles from cell culture medium is shown in FIG. 1. In summary, the cells are cultured in medium supplemented with microvesicle-free serum (the serum may be depleted of microvesicles by ultracentrifugation, filtration, precipitation, etc.). After culturing the cells for a period of time, the medium is removed and transferred to conical tubes and centrifuged at 400×g for 10 minutes at 4° C. to pellet the cells. Next, the supernatant is transferred to new conical tubes and centrifuged at 2000×g for 30 minutes at 4° C. to further remove cells and cell debris. This may be followed by another centrifugation step (e.g. 10000×g for 30 minutes to further deplete cellular debris and/or remove larger microvesicles). The resultant supernatant is transferred to ultracentrifuge tubes, weighed to ensure equal weight and ultracentrifuged at 70000+×g for 70 minutes at 4° C. to pellet the microvesicles.

This supernatant is subsequently discarded and the pellet is resuspended in ice cold PBS. The solution is ultracentrifuged at 70000+×g for 70 minutes at 4° C. to pellet the microvesicles. The microvesicle enriched pellet is resuspended in a small volume (approximately 50-100 µl) of an appropriate buffer (e.g. PBS).

Figure 2:
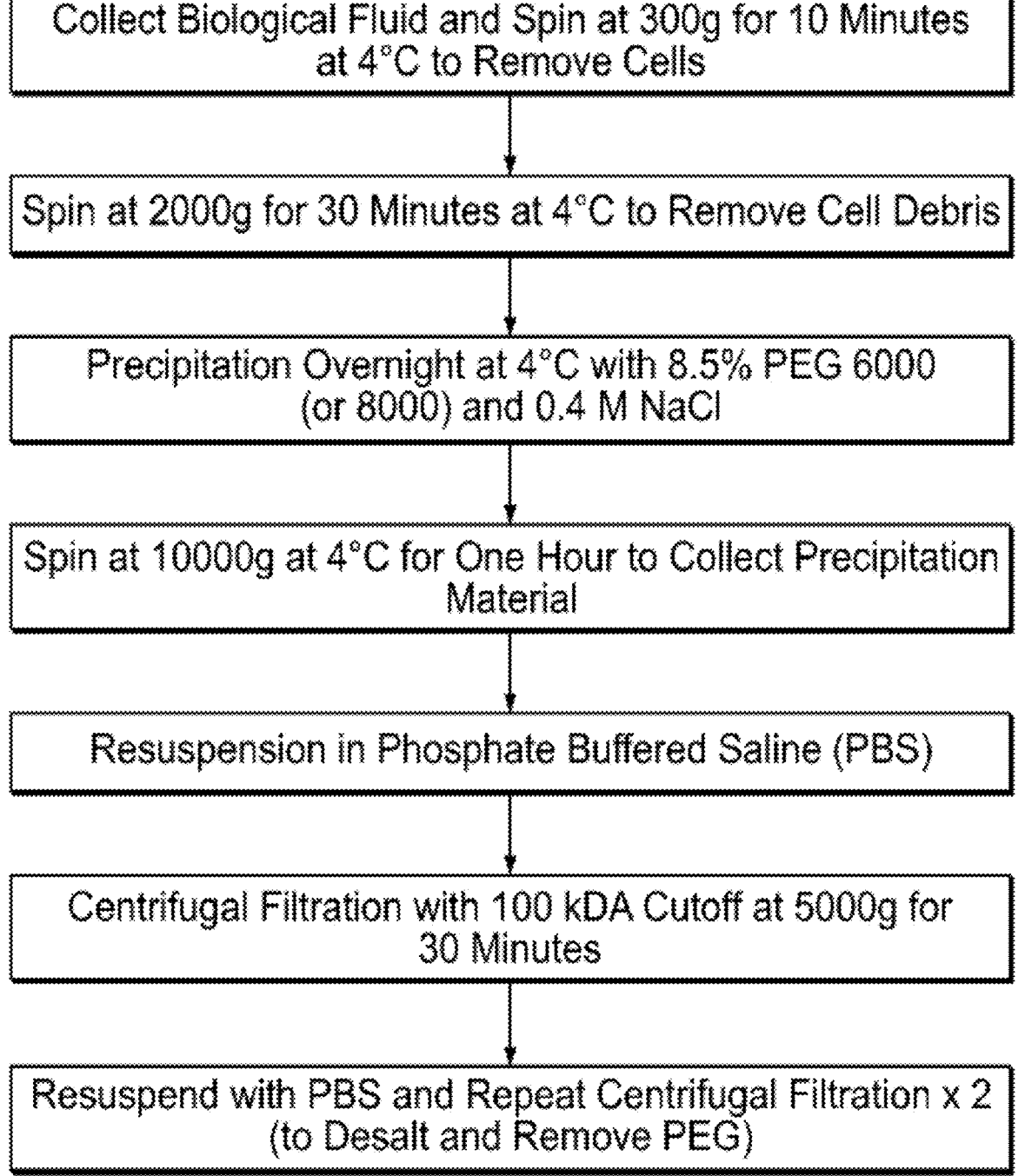
FIG. 2 shows one embodiment of a microvesicle isolation method of the present invention.

Example 2: Isolation of Microvesicles from Cell Culture Medium by the Methods of the Present Invention This example illustrates how microvesicles are isolated from cell culture medium by the methods of the present invention. An outline of the method to isolate microvesicles from medium that has cultured cells is shown in FIGS. 2 and 3. In summary, the cells are cultured in medium supplemented with microvesicle-free serum (the serum may be depleted of microvesicles by ultracentrifugation, filtration, precipitation, etc.). After culturing the cells for a period of time, the medium is removed and transferred to conical tubes and centrifuged at 400×g for 10 minutes at 4° C. to pellet the cells. Next, the supernatant is transferred to new conical tubes and centrifuged at 2000×g for 30 minutes at 4° C. to further remove cells and cell debris. This may be followed by another centrifugation step (e.g. 10000×g for 30 minutes to further deplete cellular debris and remove larger particles).

Microvesicles are then precipitated at 4° C. using 8.5% w/v PEG 6000 and 0.4 M NaCl. This mixture is spun at 10000×g at 4° C. for 30 minutes. The supernatant is removed and the pellet is resuspended in an appropriate buffer (e.g. PBS). It may be used for immediate downstream reactions or further purified. Further purification procedures can include the use of centrifugal filters (e.g. MWCO of 100 kDa), immunoaffinity, HPLC, tangential flow filtration, phase separation/partitioning, microfluidics, etc.

Example 3: Isolation of Microvesicles from Culture Medium Conditioned Using Bone Marrow Derived Stem Cells by the Methods of the Present Invention Normal donor human bone marrow was acquired from AllCells LLC (Emeryville, CA). MSCs were isolated by a standard plastic adherence method. Bone marrow mononuclear cells were isolated by low-density centrifugation using Ficoll-Paque Premium (density: 1.077 g/ml) according to the manufacturer's protocol (GE Healthcare Life Sciences, Pittsburgh, PA). The mononuclear cells were collected at the interface, washed three times in phosphate-buffered saline (PBS) supplemented with 2% FBS (Atlanta Biologics, Atlanta, GA), and resuspended in MSC medium consisting of alpha-minimum essential medium (a-MEM) (Mediatech Inc., Manassas, VA) and 20% FBS, 1% Penicillin/Streptomycin (Lonza, Allendale, NJ) and 1% glutamine (Lonza).

Initial cultures of either MSCs or mononuclear cells were seeded between 2-3×10^5 cells/cm^2 in tissue culture-treated dishes (BD Biosciences, San Jose, CA) and placed in a cell incubator at 37° C. in 95% humidified air and 5% $CO_2$. After 48-72 hours, the non-adherent cells were removed, the culture flasks were rinsed once with PBS, and fresh medium was added to the flask. The cells were grown until 80% confluence was reached and then passaged by Trypsin-EDTA (Life technologies, Carlsbad, CA). Cells were split at a 1:4 ratio into 5-layer multi-flasks (BD Biosciences). Alternatively, cryopreserved MSC were thawed at 37° C. and immediately cultured in a-MEM supplemented with 20% microvesicle-free fetal bovine serum and 1% penicillin/streptomycin/glutamine at 37° C. in 95% humidified air and 5% $CO_2$. They were expanded similar to above.

The cells were grown in the multi-flasks until 80-90% confluence was reached. The flasks were rinsed twice with PBS and a-MEM supplemented with 1% Penicillin/Streptomycin/Glutamine was added. After 24 hours, the conditioned medium transferred to 50 mL conical centrifuge tubes (Thermo Fisher Scientific Inc., Weston, FL) and immediately centrifuged at 400×g for 10 minutes at 4° C. to pellet any non-adherent cells. The supernatant was transferred to new 50 mL conical centrifuge tubes and centrifuged at 2000×g for 30 minutes at 4° C. to further remove cells and cell debris. The supernatants were collected and placed into 250 ml sterile, polypropylene disposable containers (Corning, Corning, NY). To the supernatant, RNase and protease free polyethylene glycol average molecular weight 6000 (Sigma Aldrich, Saint Louis, MO) at 8.5 w/v % and sodium chloride (final concentration 0.4 M) were added. The solution was placed in a cold room at 4° C. overnight with rocking. The solution was transferred to 50 mL conical centrifuge tubes and centrifuged at 10000×g at 4° C. for 30 minutes. The supernatant was decanted and the microvesicle enriched pellet resuspended in phosphate-buffered saline (PBS). The microvesicle enriched solution was transferred to Amicon ultra-15 centrifugal filter units (nominal molecular weight limit 100 kDa) (Millipore, Billerica, MA) and centrifuged at 5000×g for 30 minutes. The filter units were washed with phosphate-buffered saline and centrifuged again at 5000×g for 30 minutes. The concentrated sample was recovered (approximately 200 µl) from the bottom of the filter device. Protein concentration was determined by the micro BSA Protein assay kit (Pierce, Rockford, IL) and the enriched microvesicle solution was stored at −70 degrees or processed for downstream use (e.g. protein, RNA, and DNA extraction).

Example 4: Isolation of Microvesicles from Plasma by the Methods of the Present Invention Approximately 6-8 ml of blood (human and pig) was collected via venipuncture and placed into BD Vacutainer plastic EDTA lavender tubes (BD Biosciences, San Jose, CA). The venipuncture tubes were centrifuged at 400×g for 30 minutes at room temperature. Plasma was removed (approximately 3-4 ml) and placed into new 50 ml conical centrifuge tubes (Thermo Fisher Scientific Inc., Weston, FL). Sterile alpha-minimum essential medium (α-MEM) (Mediatech Inc., Manassas, VA) was added in a 1:10 (Plasma to medium) ratio.

To the solution, RNase and protease free polyethylene glycol average molecular weight 6000 (Sigma Aldrich, Saint Louis, MO) at 8.5 w/v % and sodium chloride (final concentration 0.4 M) were added. The solution was placed in a cold room at 4° C. overnight with rocking. The solution was centrifuged at 10000×g at 4° C. for 30 minutes. The supernatant was decanted and the microvesicle enriched pellet resuspended in phosphate-buffered saline (PBS). The microvesicle enriched solution was transferred to Amicon ultra-15 centrifugal filter units (nominal molecular weight limit 100 kDa) (Millipore, Billerica, MA) and centrifuged at 5000×g for 30 minutes. The filter units were washed with phosphate-buffered saline and centrifuged again at 5000×g for 30 minutes. The concentrated sample was recovered (approximately 200-400 µl) from the bottom of the filter device. Protein concentration was determined by the micro BSA Protein assay kit (Pierce, Rockford, IL) and the enriched microvesicle solution was stored at −70 degrees or processed for downstream use (e.g. protein, RNA, and DNA extraction).

Example 5: Isolation of Microvesicles from Bone Marrow Aspirate by the Methods of the Present Invention Pig bone marrow was isolated from the iliac crest. The skin area was carefully cleaned with povidine iodine 7.5% and isopropanol 70%. An 11-gauge 3 mm trocar (Ranafac, Avon, MA) was inserted into the iliac crest. An aspiration syringe with loaded with 5000-1000 units of heparin to prevent clotting of the marrow sample. Approximately 20-25 ml of marrow was aspirated and the solution transferred to 50 ml conical centrifuge tubes. Alternatively, normal donor human bone marrow (approximately 50 ml) was acquired from AllCells LLC (Emeryville, CA, URL: allcells.com).

The 50 ml conical tubes were centrifuged at 400×g for 30 minutes at room temperature. The supernatant (the acellular portion) was collected (approximately 10-12 ml per 50 ml) and placed into new 50 ml conical centrifuge tubes (Thermo Fisher Scientific Inc., Weston, FL). Sterile alpha-minimum essential medium (α-MEM) (Mediatech Inc., Manassas, VA) was added in a 1:10 (bone marrow supernatant to medium) ratio. The solution was transferred to new 50 ml conical tubes and centrifuged at 2000×g for 30 minutes at 4° C. The supernatant was transferred to new 50 ml conical tubes and to this solution, RNase and protease free polyethylene glycol average molecular weight 6000 (Sigma Aldrich, Saint Louis, MO) at 8.5 w/v % and sodium chloride (final concentration 0.4 M) were added.

The solution was placed in a cold room at 4° C. overnight with rocking. The solution was centrifuged at 10000×g at 4° C. for 30 minutes. The supernatant was decanted and the microvesicle enriched pellet resuspended in phosphate-buffered saline (PBS). The microvesicle enriched solution was transferred to Amicon ultra-15 centrifugal filter units (nominal molecular weight limit 100 kDa) (Millipore, Billerica, MA) and centrifuged at 5000×g for 30 minutes. The filter units were washed with phosphate-buffered saline and centrifuged again at 5000×g for 30 minutes. The concentrated sample was recovered (approximately 200-400 µl) from the bottom of the filter device. Protein concentration was determined by the micro BSA Protein assay kit (Pierce, Rockford, IL) and the enriched microvesicle solution was stored at −70 degrees or processed for downstream use (e.g. protein, RNA, and DNA extraction).

The cellular portion was collected and processed for mesenchymal stem isolation or for bone marrow complete isolation.

Example 6: Isolation of Microvesicles from Urine by the Methods of the Present Invention Approximately 500 ml of clean catch human urine was isolated and placed into 50 ml conical tubes (Thermo Fisher Scientific Inc., Weston, FL).

The 50 ml conical tubes were centrifuged at 400×g for 30 minutes at 4° C. The supernatant was removed and placed into new 50 ml conical centrifuge tubes (Thermo Fisher Scientific Inc., Weston, FL). The solution was transferred to new 50 ml conical tubes and centrifuged at 2000×g for 30 minutes at 4° C. The supernatant was transferred to new 50 ml conical tubes and to this solution, RNase and protease free polyethylene glycol average molecular weight 6000 (Sigma Aldrich, Saint Louis, MO) at 8.5 w/v % and sodium chloride (final concentration 0.4 M) were added.

The solution was placed in a cold room at 4° C. overnight with rocking. The solution was centrifuged at 10000×g at 4° C. for 30 minutes. The supernatant was decanted and the microvesicle enriched pellet resuspended in phosphate-buffered saline (PBS). The microvesicle enriched solution was transferred to Amicon ultra-15 centrifugal filter units (nominal molecular weight limit 100 kDa) (Millipore, Billerica, MA) and centrifuged at 5000×g for 30 minutes. The filter units were washed with phosphate-buffered saline and centrifuged again at 5000×g for 30 minutes. The concentrated sample was recovered (approximately 200-400 µl) from the bottom of the filter device. Protein concentration was determined by the micro BSA Protein assay kit (Pierce, Rockford, IL) and the enriched microvesicle solution was stored at −70 degrees or processed for downstream use (e.g. protein, RNA, and DNA extraction).

Example 7: Isolation of Microvesicles from Medium from a Long-Term Culture of Bone Marrow Cells by the Methods of the Present Invention Bone marrow was obtained from an aspirate (see Example 1) and red blood cells were lysed using 0.8% ammonium chloride solution containing 0.1 mM EDTA (Stem Cell Technologies, Vancouver, BC). The nucleated cells were pelleted under a fetal bovine serum (Atlanta Biologics, Atlanta, GA) cushion at 400×g for 5 minutes. Nucleated cells were washed in McCoy's 5a media (Mediatech Inc., Manassas, VA) by pelleting at 400×g for 5 min. The cells were resuspended in culture media at a density of $1 \times 10^6$ cells/ml and plated in 25, 75 or 225 cm$^2$ flasks (Corning, Corning, NY).

Culture media consisted of McCoy's 5a media, 1% sodium bicarbonate (Life technologies, Carlsbad, CA), 0-4% MEM non-essential amino acids (Life technologies), 0-8% MEM essential amino acids (Life technologies), 1% L-glutamine (Lonza, Allendale, NJ), 0.1 µM Hydrocortisone (Life technologies), 1% penicillin/streptomycin (Lonza), 12-5% fetal calf serum (Atlanta Biologics) and 12-5% horse serum (Stem Cell Technology). The cultures were incubated at 33° C. and 5% $CO_2$. Feeding was performed weekly by adding half of the original volume of media without removing any media during the first nine weeks of culture. If the cultures were grown beyond nine weeks, the volume of culture media was reduced to the original volume and half the original volume of fresh media was added each week.

After approximately nine weeks of culture, the original medium was removed and stored. The cells were washed twice with phosphate buffered saline (PBS) and incubated for 24 hours in media consisting of McCoy's 5a media, 1% sodium bicarbonate, 0-4% MEM nonessential amino acids, 0-8% MEM essential amino acids (Life technologies), 1% L-glutamine (Lonza, Allendale, NJ), and 1% penicillin/streptomycin (Lonza).

After 24 hours, the supernatant was transferred to 50 mL conical centrifuge tubes (Thermo Fisher Scientific Inc., Weston, FL) and immediately centrifuged at 400×g for 10 minutes at 4° C. to pellet any non-adherent cells. The original medium that was stored was added back to the cells. The supernatant were transferred to new 50 mL conical centrifuge tubes and centrifuged at 2000×g for 30 minutes at 4° C. to further remove cells and cell debris.

The supernatant was collected and placed into 250 ml sterile, polypropylene disposable containers (Corning, Corning, NY). To the supernatant, RNase and protease free polyethylene glycol average molecular weight 6000 (Sigma Aldrich, Saint Louis, MO) at 8.5 w/v % and sodium chloride (final concentration 0.4 M) was added. The solution was placed in a cold room at 4° C. overnight with rocking. The solution was transferred to 50 mL conical centrifuge tubes and centrifuged at 10000×g at 4° C. for 30 minutes. The supernatant was decanted and the microvesicle enriched pellet resuspended in phosphate-buffered saline (PBS). The microvesicle enriched solution was transferred to Amicon ultra-15 centrifugal filter units (nominal molecular weight limit 100 kDa) (Millipore, Billerica, MA) and centrifuged at 5000×g for 30 minutes. The filter units were washed with phosphate-buffered saline and centrifuged again at 5000×g for 30 minutes. The concentrated sample was recovered (approximately 200 µl) from the bottom of the filter device. Protein concentration was determined by the micro BSA Protein assay kit (Pierce, Rockford, IL) and the enriched microvesicle solution stored at −70 degrees or processed for downstream use (e.g. protein, RNA, and DNA extraction).

Example 8: Analysis of the Microvesicles of the Present Invention

Samples of microvesicles were analyzed by electron microscopy. For transmission electron microscopy (TEM), each specimen of microvesicles was loaded on formvar-coated, 150 mesh copper grids (Electron Microscopy Sciences, Fort Washington, PA) for 20 minutes. The grids were drained and floated on drops of 2% glutaraldehyde for 5 minutes, then washed in double distilled water (DDOH), followed by staining on drops of 4% aqueous uranyl acetate and multiple washes in DDOH. The grids were examined at 80 kV in a Philips CM10 electron micro scope.

Figures 6A, 6B, 6C, 6D:
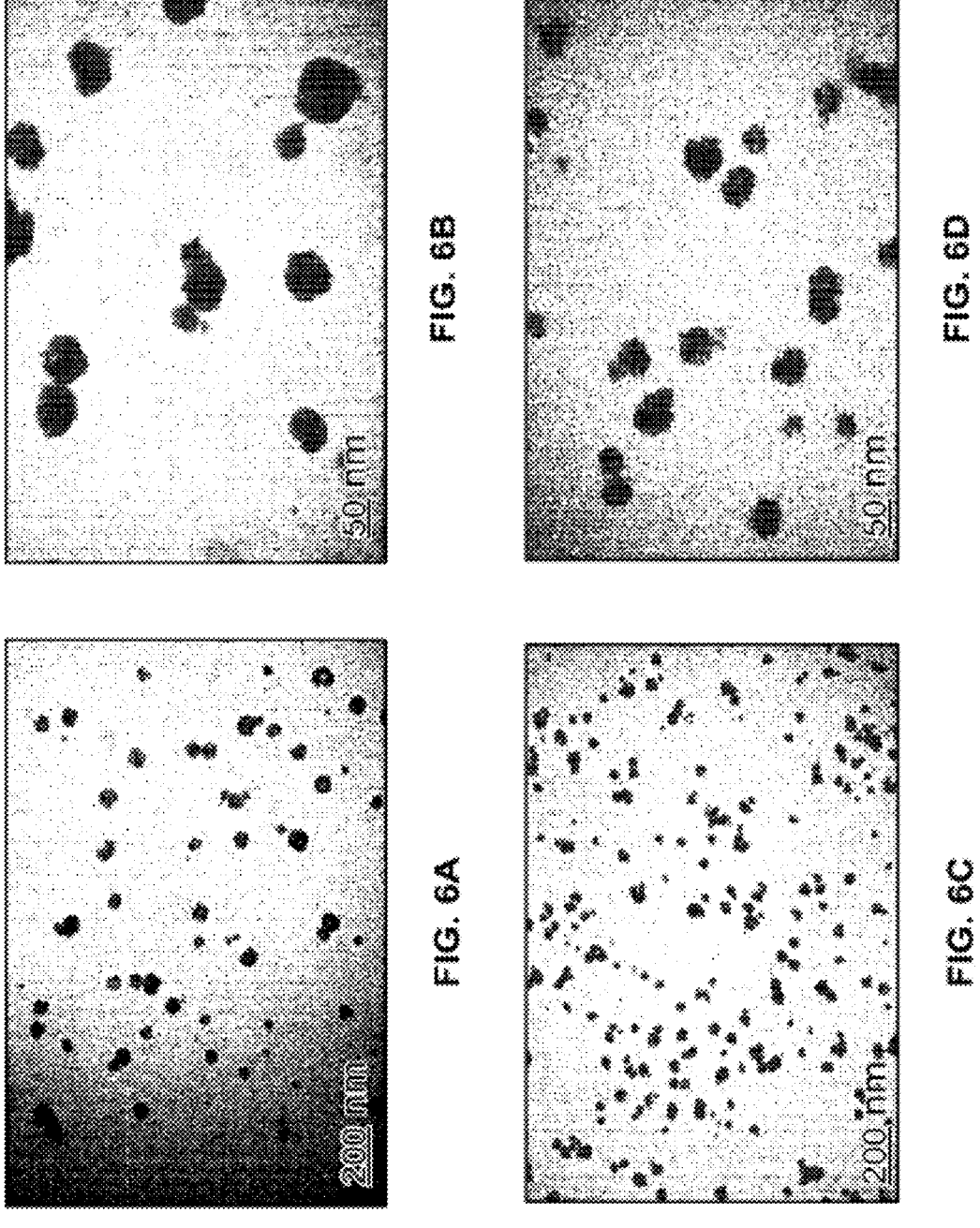
FIG. 6A-FIG. 6D show electron micrographs of microvesicles derived from medium conditioned using porcine bone marrow-derived mesenchymal stem cells isolated by the ultracentrifuge method described in Example 1 (FIG. 6A & FIG. 6B) and isolated according to the methods of the present invention (FIG. 6C & FIG. 6D) at the magnifications shown in the panels.
Figures 7A, 7B, 7C, 7D:
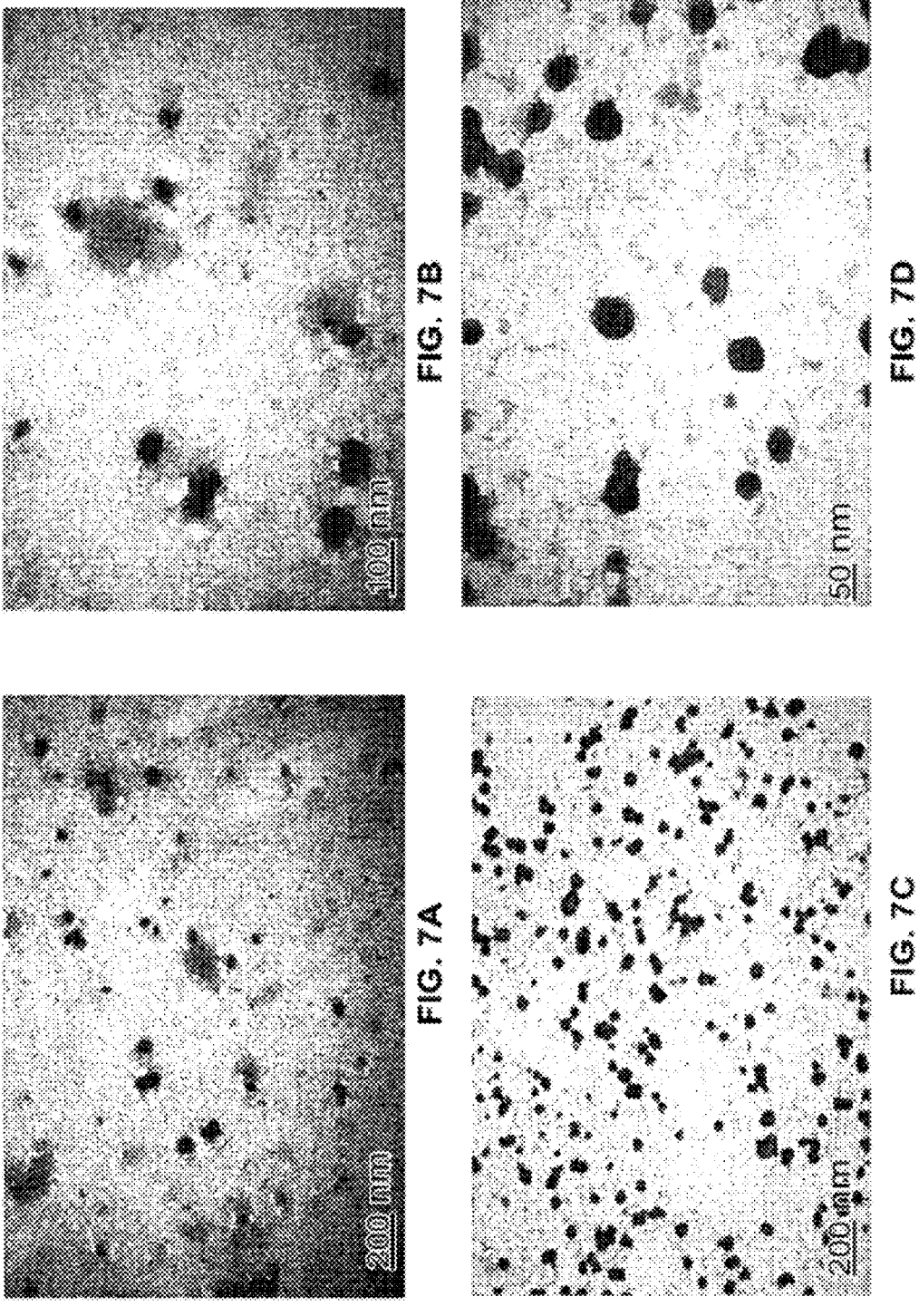
FIG. 7A-FIG. 7D show electron micrographs of microvesicles derived from medium conditioned using murine bone marrow-derived mesenchymal stem cells isolated by the ultracentrifuge method described in Example 1 (FIG. 7A & FIG. 7B) and isolated according to the methods of the present invention (FIG. 7C & FIG. 7D) at the magnifications shown in the panels.

FIG. 5 shows electron micrographs of microvesicles derived from human bone marrow-derived mesenchymal stem cells isolated by the ultracentrifuge method described in Example 1 (panels A&B) and according to the methods of the present invention as described in Example 3 (panels C&D). FIG. 6 shows electron micrographs of microvesicles derived from porcine bone marrow-derived mesenchymal stem cells isolated by the ultracentrifuge method described in Examples 1 (panels A&B) and according to the methods of the present invention as described in Example 3 (panels C&D). FIG. 7 shows electron micrographs of microvesicles derived from murine bone marrow-derived mesenchymal stem cells isolated by the ultracentrifuge method described in Examples 1 (panels A&B) and according to the methods of the present invention as described in Example 3 (panels C&D).

FIGS. 5 to 7 illustrate the differences between microvesicles isolated by the methods of the present invention compared to ultracentrifuge isolation. The microvesicles isolated according to the methods of the present invention have borders that are smoother, uncorrugated and appear more "intact."

Figure 9B:
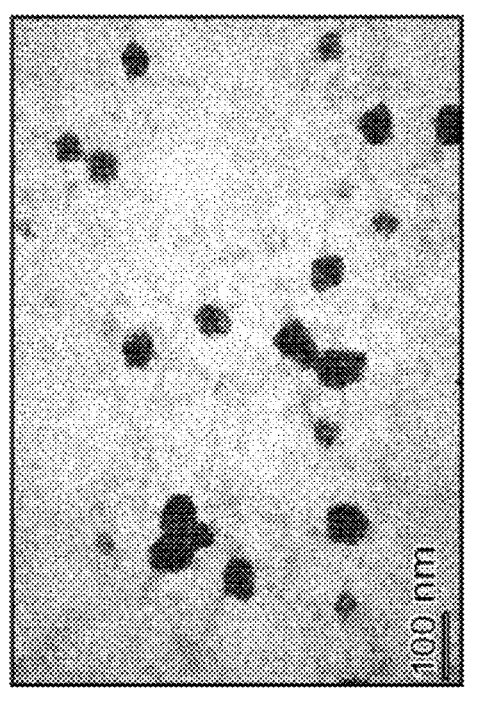
FIG. 9A-FIG. 9C show electron micrographs of microvesicles isolated from porcine plasma according to the methods of the present invention.
Figure 9C:
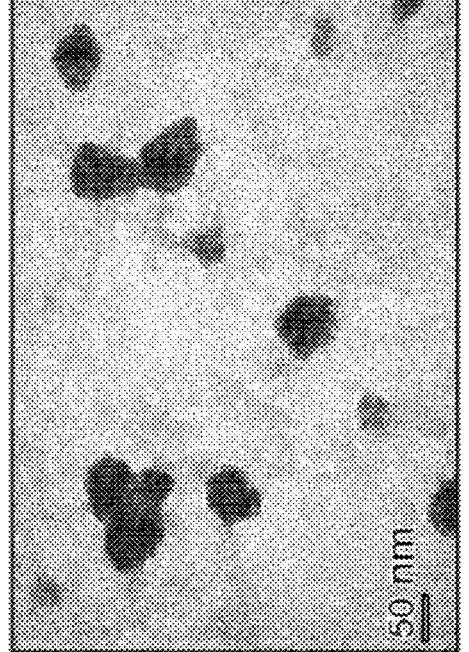
Figure 9A:
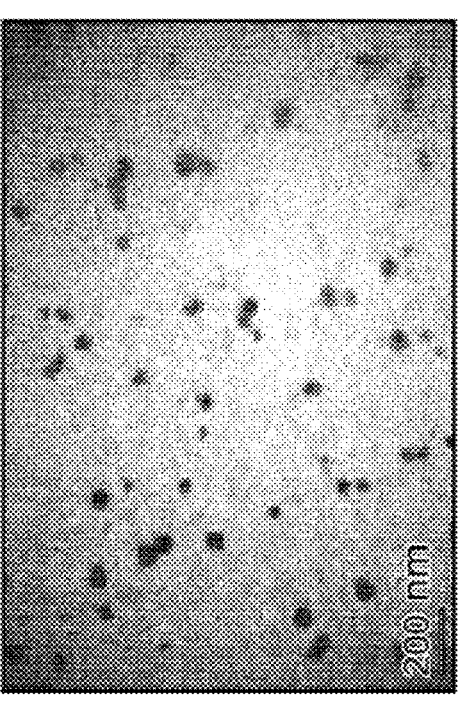

FIG. 8 shows electron micrographs of microvesicles isolated from human plasma according to the methods of the present invention. The heterogeneity of the shapes and sizes achieved with PEG isolation suggests that all types of microvesicles were isolated. Similar heterogeneity was observed in microvesicles from porcine plasma (FIG. 9) and human urine (FIG. 10) that were isolated according to the methods of the present invention.

To analyze protein expression in samples of microvesicles, cells and microvesicles were lysed in RIPA buffer (Cell signaling technology, Danvers, MA) and protein concentration estimated by the microBSA assay kit (Pierce, Rockford, IL). Approximately 20 micrograms of lysate were loaded in each lane and the membranes were probed overnight (1:1000) by either Rabbit anti-63 antibody (SBI Biosciences, Mountain View, CA), Rabbit anti-hsp70 (SBI Biosciences), rabbit STAT3 (Cell signaling technology), and/or rabbit phospho-STAT3 (Cell signaling technology).

Figure 11:
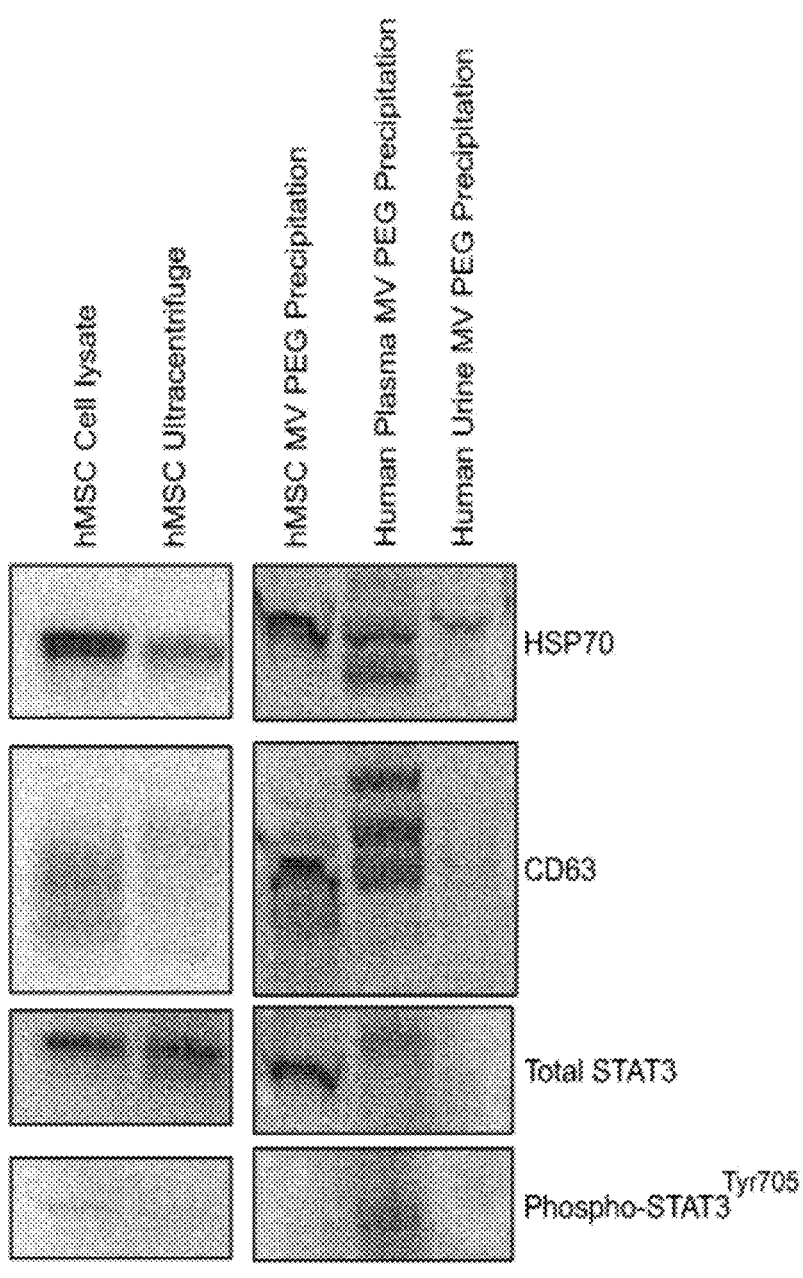
FIG. 11 shows a Western blot, reporting the expression of HSP70, CD63, STAT 3 and phosphorylated STATS in lysates of human bone marrow-derived mesenchymal stem cells, microvesicles isolated from medium conditioned using human bone marrow-derived stem cells, prepared by ultracentrifugation (hMSC MV Ultracentrifuge), or the methods of the present invention, as described in Example 3 (hMSC PEG Precipitation). Microvesicles derived from human plasma and human urine, prepared by the methods of the present invention, as described in Example 3 were also analyzed. (Human plasma PEG Precipitation) and (human urine PEG Precipitation) respectively.

The presence of the exosomal markers (HSP 70 and CD63) confirmed that the methods of the present invention were capable of isolating exosomes. Further, the exosomes also contained the transcription factor STAT3 and the activated phosphorylated form phospho-STAT3. See FIG. 11.

Figures 12A, 12B, 12C:
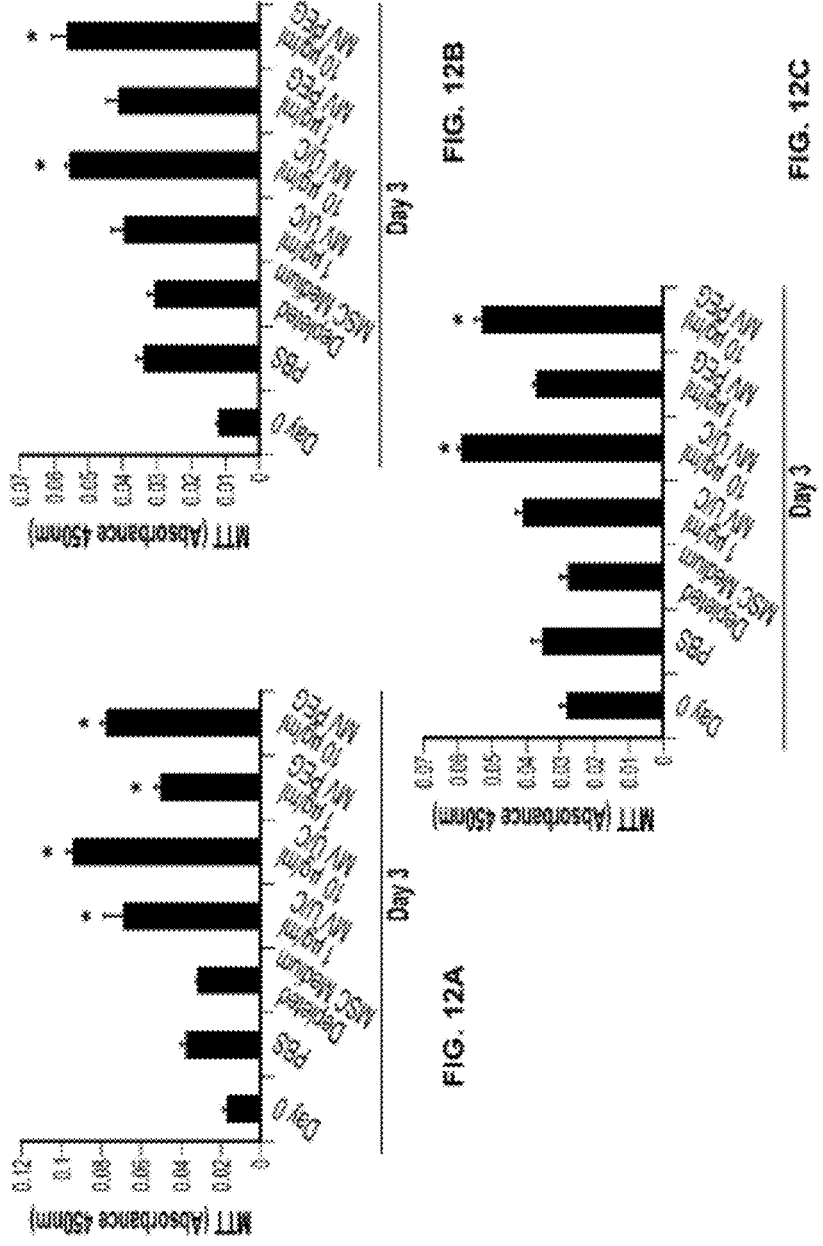
FIG. 12A-FIG. 12C show the effect of microvesicles isolated from medium conditioned using human bone marrow-derived mesenchymal stem cells on the proliferation of normal human dermal fibroblasts (FIG. 12A), dermal fibroblasts obtained from a diabetic foot ulcer (FIG. 12B), and dermal fibroblasts obtained from a pressure foot ulcer (FIG. 12C). The effect of microvesicles isolated by ultracentrifugation (MV U/C) and microvesicles isolated by the methods of the present invention (MV PEG) were compared. Fibroblasts treated with PBS or microvesicle depleted culture medium were included as a control. Proliferation was determined using an MTT assay.

Example 9: The Effect of the Microvesicles of the Present Invention on Fibroblast Proliferation and Migration To study the ability the microvesicles of the present invention to promote or enhance wound healing, the ability of the microvesicles to stimulate the proliferation of dermal fibroblasts was tested. Normal human adult dermal fibroblasts were obtained from Life Technology (Carlsbad, CA). Chronic wound patient fibroblasts (pressure foot ulcer and diabetic foot ulcer) were collected under an IRB approved protocol (IND# BB IND 13201) from wounds of 2 years duration without evidence of healing despite standard of care and advanced wound care treatments. Normal and Chronic wound fibroblasts were plated at $5 \times 10^3$ cells per well on 24 well tissue culture plates (BD Biosciences, San Jose, CA). MTT cell proliferation assays were performed at day 0 and day 3. Microvesicles were added on day 0. Both PEG isolated and ultracentrifuge isolated microvesicles were approximately equivalent in increasing growth of both normal and chronic wound fibroblasts after 3 days. Phosphate buffered saline (PBS) and conditioned MSC medium depleted of microvesicles showed little growth. See FIG. 12.

Figures 13A, 13B, 13C, 13D, 13E, 13F, 13G:
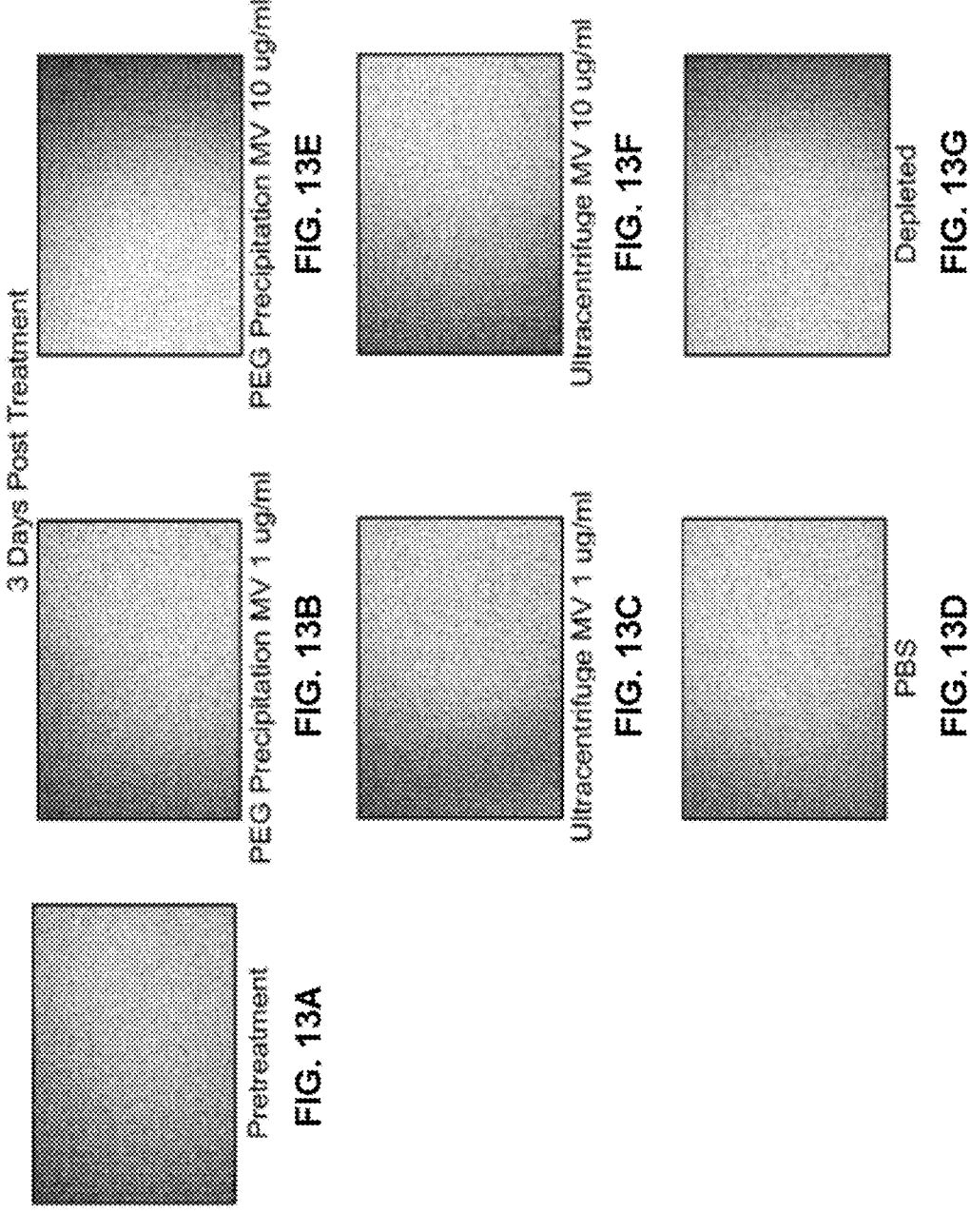
FIG. 13A-FIG. 13G shows the effect of microvesicles isolated from medium conditioned using human bone marrow-derived mesenchymal stem cells on the migration of human dermal fibroblasts, as determined by the ability of the fibroblasts to migrate into a region that had been scratched off. The panel labeled "pretreatment" shows a representative area of a cell culture plate where the cells were removed, prior to the addition of the test treatments (FIG. 13A). The effect of fibroblast migration was tested using microvesicles isolated according to the methods of the present invention (PEG precipitation.

In co-culture experiments, normal adult fibroblasts and fibroblast from a diabetic foot ulcer were seeded in twenty four well plates. Each well was seeded to achieve 100% confluency (approximately $1 \times 10^5$ cells per well). To prevent the influence of cell proliferation, 2 hours prior to scratch, the medium was substituted with a fresh serum-free culture medium containing mitomycin at 10 µg/ml. The confluent monolayer was then scored with a 1 ml sterile pipette tip to leave a scratch of 0.4-0.5 mm in width. Culture medium was then immediately removed (along with any dislodged cells). The removed medium was replaced with fresh culture medium (10% FBS) containing either microvesicles (PEG or ultracentrifuge derived), PBS, or MSC conditioned medium depleted of microvesicles. The scratched area was monitored by collecting digitized images immediately after the scratch and 3 days after treatment. Digitized images were captured with an inverted IX81 Olympus microscope (Olympus America, Center Valley, PA, URL: olympusamerica.com) and ORCA-AG Hamamatsu digital camera (Hamamatsu Photonics K.K., Hamamatsu City, Shizuoka Pref., Japan, URL: hamamatsu.com). Three days after treatment, microvesicles isolated according to the methods of the present invention showed the greatest in migration (essentially closing the wound), followed by microvesicles derived from ultracentrifuge. The controls (PBS) and MSC conditioned medium depleted of microvesicles (Depleted) showed little migration. See FIG. 13.

FIG. 14 shows the effects of microvesicles on cell migration fibroblasts derived from a diabetic foot ulcer. Similar to the results in FIG. 13, microvesicles isolated according to the methods of the present invention evoked the greatest migration, followed by microvesicles isolated using the ultracentrifuge method described in Example 1. The controls (PBS) and MSC conditioned medium depleted of microvesicles (Depleted) showed little migration.

Example 10: Uptake of the Microvesicles of the Present Invention into Cells

Human MSC microvesicles isolated from conditioned medium according to the methods of the present invention were labeled with the phospholipid cell linker dye PKH-26 (red) per manufacturer's instruction (Sigma-Aldrich, St. Louis, MO). Normal skin fibroblasts were labeled with Vybrant-Dio (Life technology) per manufacturer instructions. Normal skin fibroblasts were plated on fibronectin (Sigma-Aldrich) coated 4-well Nunc* Lab-Tek* II Chamber Slides (Thermo Fisher Scientific Inc., Weston, FL) ($5 \times 10$ cells per well). Cells were stained with the nuclear dye Hoechst 33342 (Life technology) per manufacturer's instructions. Dio labeled fibroblasts were treated with PKH-26 labeled microvesicles for 24 hours. Images were captured with an inverted 1×81 Olympus microscope and ORCA-AG Hamamatsu digital camera. Normal dermal fibroblasts (stained with the green lipid membrane dye Dio) demonstrated uptake of PKH-26 labeled human MSC MV isolated by PEG precipitation in a peri-nuclear location. See FIGS. 15 and 16. In FIG. 16, the microvesicles are seen in a peri-nuclear location.

Example 11: Use of the Microvesicles of the Present Invention as a Diagnostic for Rheumatoid Arthritis Normal dermal fibroblasts were plated at a density of $1 \times 10^5$ cells/well in a 6-well tissue culture plate (BD Biosciences). Fibroblasts were serum starved overnight and treated with PBS (control), 10 micrograms of either microvesicles isolated according to the methods of the present invention from plasma obtained from a patient suffering from rheumatoid arthritis (Human Plasma MV PEG Precipitation); microvesicles isolated according to the methods of the present invention from medium conditioned with bone marrow-derived mesenchymal stem cells (Human hMSC MV PEG Precipitation); microvesicles isolated according via ultracentrifugation from medium conditioned with bone marrow-derived mesenchymal stem cells (Human hMSC MV ultracentrifugation); PBS control; and a depleted medium control (hMSC conditioned medium depleted of MV). The amount of STAT3 phosphorylation observed in the fibroblasts was greater in the microvesicles isolated according to the methods of the present invention. See FIG. 17.

Example 12: Use of the Microvesicles of the Present Invention as a Diagnostic for Metastatic Melanoma BRAF is a human gene that makes a protein called B-Raf. More than 30 mutations of the BRAF gene associated with human cancers have been identified. We have designed per primers to amplify the mutated form of BRAF that is linked to metastatic melanoma. The mutation is a T1799A mutation in exon 15 in BRAF. This leads to valine (V) being substituted for by glutamate (E) at codon 600 (now referred to as V600E). The presence of this mutation is required for treatment by the BRAF inhibitor Vemurafenib. The SK-Me128 cell line, obtained from ATCC (Washington DC, Maryland) is known to have the T1799A mutation in exon 15 in BRAF. Microvesicles, isolated according to the methods of the present invention were obtained from medium conditioned by a 3 day incubation in EMEM (ATCC)+10% serum (Atlanta Biologics, Atlanta, Georgia).

The isolated microvesicles were processed for DNA and RNA isolation using Qiagen's (Hilden, Germany) AUPrep DNA/RNA kit. Approximately 50 ng of RNA from SK-MEL28 cells and microvesicles were reverse transcribed using iScript™ Reverse Transcription Supermix (BioRad, Hercules, CA). A 2 ml aliquot was used for PCR utilizing Platinum® PCR SuperMix (Life technology) per manufacturer's instructions. In addition, 80 ng of DNA from SK-MEL28 cells and microvesicles was used for PCR utilizing Platinum® PCR SuperMix per manufacturer's instructions. PCR products were run on a 3% agarose gel and visualized by Bio-Rad's gel-doc system. The results are shown in FIG. 18.

The primers used were:

```
Sequence 1:
Forward:
                                  (SEQ ID NO: 1)
AGACCTCACAGTAAAAATAGGTGA Reverse:
                                  (SEQ ID NO: 2)
CTGATGGGACCCACTCCATC Amplicon length: 70
```

-continued

```
Sequence 2:
Forward:
                                    (SEQ ID NO: 3)
GAAGACCTCACAGTAAAAATAGGTG Reverse:
                                    (SEQ ID NO: 4)
CTGATGGGACCCACTCCATC Amplicon length: 82
```

In addition, samples of the microvesicles were lysed in RIPA buffer and protein concentration estimated by the microBSA assay kit. Approximately 50 microgram were loaded in each lane and the membranes were probed overnight (1:1000) by mouse anti-BRAF V600E antibody (NewEast Biosciences, Malvern, PA). Secondary antibody, goat anti-mouse (Pierce) was applied at 1:10000 dilution for 1 hour. The Western blot shows BRAF V600E detection in SKMEL28 cell and MV lysate.

Example 13: Isolation of Microvesicles from Medium Conditioned Using a Culture of GFP-Labeled Bone Marrow-Derived Mesenchymal Stem Cells by the Methods of the Present Invention Homozygous transgenic mice expressing the enhanced Green Fluorescent Protein (GFP) under the direction of the human ubiquitin C promoter (C57BL/6-Tg(UBC-GFP) 30Scha/J) were obtained from Jackson Laboratories (Bar Harbor, Maine). These mice are known to express GFP in all tissues.

GFP-Mice (approximately 3-4 weeks of age) were euthanized by $CO_2$ asphyxiation. The limbs were cut above the hip and below the ankle joint. The hind limbs were harvested and skin, muscle, and all connective tissue was removed. The bones were then placed in a dish of ice cold sterile IX PBS and washed several times in PBS. The ends of each bone were snipped off with scissors. A 10 cc syringe with warmed medium (α-MEM supplemented with 20% fetal bovine serum and 1% penicillin/streptomycin/glutamine) was forced through the bone shaft to extract all bone marrow into a 150 mm plate. This was repeated several times to ensure all the marrow was removed. The cell mixture was pipetted several times to dissociate cells and the cell suspension was passed through a cell strainer (70 μm size) (BD Biosciences, San Jose, CA) to remove large cell clumps or bone particles.

Initial cultures were seeded between 2-3×10$^5$ cells/cm$^2$ in tissue culture-treated dishes (BD Biosciences, San Jose, CA) and placed in a cell incubator at 37° C. in 95% humidified air and 5% $CO_2$. After 72-96 hours, the non-adherent cells were removed, the culture flasks were rinsed once with PBS, and fresh medium was added to the flask. The cells were grown until 80% confluence was reached and then passaged by Trypsin-EDTA (Life technologies, Carlsbad, CA). Cells were split at a 1:4 ratio.

Alternatively, cryopreserved GFP Mouse-MSC's were thawed at 37° C. and immediately cultured in α-MEM supplemented with 20% fetal bovine serum and 1% penicillin/streptomycin/glutamine at 37° C. in 95% humidified air and 5% $CO_2$. They were expanded similar to above.

The cells were grown in the flasks until 100% confluence was reached (approximately 1 week). The supernatant were transferred to 50 mL conical centrifuge tubes (Thermo Fisher Scientific Inc., Weston, FL) and immediately centrifuged at 400×g for 10 minutes at 4° C. to pellet any non-adherent cells. The supernatant was transferred to new 50 mL conical centrifuge tubes and centrifuged at 2000×g for 30 minutes at 4° C. to further remove cells and cell debris. The supernatants were collected and placed into 250 ml sterile, polypropylene disposable containers (Corning, Corning, NY). To the supernatant, RNase and protease free polyethylene glycol average molecular weight 6000 (Sigma Aldrich, Saint Louis, MO) at 8.5 w/v % and sodium chloride (final concentration 0.4 M) were added. The solution was placed in a cold room at 4° C. overnight with rocking. The solution was transferred to 50 mL conical centrifuge tubes and centrifuged at 10000×g at 4° C. for 30 minutes. The supernatant was decanted and the microvesicle enriched pellet resuspended in phosphate-buffered saline (PBS). The microvesicle enriched solution was transferred to Amicon ultra-15 centrifugal filter units (nominal molecular weight limit 100 kDa) (Millipore, Billerica, MA) and centrifuged at 5000×g for 30 minutes. The filter units were washed with phosphate-buffered saline and centrifuged again at 5000×g for 30 minutes. The concentrated sample was recovered (approximately 200-400 μl) from the bottom of the filter device. Protein concentration was determined by the micro BSA Protein assay kit (Pierce, Rockford, IL) and the enriched microvesicle solution was stored at −70 degrees or processed for downstream use (e.g. protein, RNA, and DNA extraction).

To determine cellular uptake of the microvesicles, normal human skin fibroblasts were labeled with Vybrant-Dio (Life technology) per manufacturer instructions. Normal skin fibroblasts were plated on fibronectin (Sigma-Aldrich) coated 4-well Nunc* Lab-Tek* II Chamber Slide (Thermo Fisher Scientific Inc.) (5×10 cells per well). Cells were stained with the nuclear dye Hoechst 33342 (Life technology) per manufacturer's instructions. Dil labeled fibroblasts were treated with microvesicles isolated from GFP expressing mouse MSC for 24 hours. Images were captured with an inverted IX81 Olympus microscope and ORCA-AG Hamamatsu digital camera. See FIGS. 20 and 21. Importantly, these images show that the microvesicles containing GFP were taken up by the cells.

Example 14: Use of the Microvesicles of the Present Invention as a Therapy to Promote or Enhance Wound Healing Full thickness wounds were created on the backs of pigs using a 10 mm punch biopsy instrument. Microvesicles were isolated from culture medium conditioned using autologous bone marrow-derived mesenchymal stem cells, either according to the methods described in Example 1 (the "conventional ultracentrifugation method"), or by the methods described in Example 3. 30 micrograms of microvesicles were administered to the wounds by local injection at the time of wounding and at Days 1 and 2. Controls were treated with saline or allowed to heal air exposed. After 5 days, the animals were euthanized, and the wounds examined.

FIG. 22 shows the histology of the wounds 5 days post-wounding. At 5 days, wounds treated with microvesicles isolated according to the methods of the present invention (i.e., according to the methods described in Example 3) appeared smaller than saline controls, air exposed controls and wounds treated with microvesicles prepared by ultracentrifugation. The wounds treated with microvesicles prepared by ultracentrifugation showed an enhanced inflammatory response, compared to those treated with microvesicles prepared according to the methods of the present invention and both controls.

In another study, second degree burn wounds were created on the backs of pigs using a brass rod heated to 100° C. Microvesicles were isolated from culture medium conditioned using autologous bone marrow-derived mesenchymal stem cells, either according to the methods described in Example 1 (the "conventional ultracentrifugation method"), or by the methods described in Example 3. 30 micrograms of microvesicles were administered to the wounds by local injection at the time of wounding and at days 1 and 2. Controls were treated with saline or allowed to heal air exposed.

Over the course of the experiment (up to 28 days post-burn injury) wounds treated with microvesicles prepared by ultracentrifugation were significantly more inflamed than those treated with microvesicles prepared according to the methods of the present invention (i.e., according to the methods described in Example 3). See FIG. 23. Similarly, wounds treated with microvesicles prepared by ultracentrifugation were significantly more inflamed than saline controls and air exposed controls. Burn wounds treated with microvesicles prepared according to the methods of the present invention did not appear significantly more inflamed than controls.

FIG. 23 illustrates the difference in inflammation at Day 7 post-wounding between wounds treated with microvesicles prepared by ultracentrifugation, microvesicles prepared according to the methods of the present invention and an air exposed control. Microscopically, abscess formation was seen in both full thickness and burn wounds treated with microvesicles prepared by ultracentrifugation. Without intending to be bound by scientific theory, the inflammation noted with microvesicles prepared by ultracentrifugation was thought to be due to damaged microvesicles, which can easily stimulate an inflammatory cascade. The microvesicles of the present invention may also confer additional benefits by including additional particles.

FIG. 24 shows a second degree porcine burn wound treated with microvesicles isolated by the methods of the present invention 28 days after burn injury. There is a significant remodeling of collagen, with the appearance of ground substance. These findings are indicative of dermal remodeling with collagen type III formation. There is also dermal epidermal induction resulting in a thickened epidermis that appears well anchored to the dermis. These findings are not observed in scar formation and are more consistent with dermal regeneration. An epidermis forming over a scar is easily subject to re-injury due to the inability to anchor well to a scarred dermis.

FIG. 25 shows a second degree porcine burn wound treated with saline 28 days after burn injury. There is minimal dermal regeneration with a flattened epidermis. The lack of significant rete ridge formation is highly suggestive of an inadequately anchored epidermis. These findings are much more indicative of scar formation with the risk of continued injury.

FIG. 26 shows a full thickness porcine wound treated with microvesicles isolated according to the methods of the present invention 28 days after injury. There is ingrowth of a nerve (illustrated by the arrows) into the remodeling dermis, likely stimulated by the application of the microvesicles. The nerve grown is accompanied by an angiogenic response (circled areas). The nerve appears to be a developed structure and is not due to simple axon sprouting. This is a unique finding and has never been reported and was also not observed in control wounds or wounds treated with microvesicles prepared by ultracentrifugation. These observations are highly indicative of complex tissue regeneration with the ability to generate mature elements from all germ layers including epidermis, stroma, vasculature and nervous tissue. These methods then appear to be widely applicable to the treatment of numerous conditions including traumatic, inflammatory, neoplastic and degenerative disorders of ectodermal, endodermal and mesodermal derived tissues.

FIG. 27 shows a full thickness porcine wound treated with microvesicles isolated by the methods of the present invention 28 days after injury. This Figure illustrates the observations described in FIG. 26 at greater magnification. In A) the nerve growth appears to be following a path related to the angiogenic response. This finding is interesting as nerve growth is well known to follow angiogenesis in embryologic development. Again, these findings are indicative of tissue regeneration. B) shows the nerve at higher power. C) better illustrates the angiogenesis adjacent to the nerve growth.

Bone formation was seen in all treatment groups (control and microvesicle treated) in the porcine full thickness wound model. See FIG. 28. Animals received a total of 1.44 mg microvesicles (half prepared according to the methods of the present invention and half by ultracentrifugation). There then appeared to be a systemic effect stimulating the formation of bone in all wounds. Bone formation tended to occur more in more inflammatory wounds suggesting a synergistic effect of local inflammatory mediators and the systemic effect of microvesicles.

Example 15: Use of the Microvesicles of the Present Invention as a Therapy to Repopulate Bone Marrow and Regenerate Complex Structures C57/CJ6 (GFP) mice were lethally irradiated with two cycles of 400 cGy gamma irradiation to ablate their host bone marrow progenitors. After irradiation, mice were treated in an approximately 2 cm area with an ablative fractional Erbium: YAG laser. After laser treatment, a plastic chamber was adhered to the skin, and bone marrow derived cells obtained from a syngeneic GFP<+>transgenic mouse were added to the chamber. The GFP bone marrow cells included, freshly harvested total bone marrow cells, lineage negative selected bone marrow cells, mesenchymal stem cells and bone marrow complete cultured cells (as described in this application). In only a few animals was chimerism able to be achieved; detected by circulating GFP cells 4 to 6 weeks after administration of cells. (See FIG. 29.) Surprisingly, many animals survived without evidence of donor bone marrow engraftment. Overall (in all groups of cells given) 30% of animals receiving cells survived. Among the different groups, survival rates were highest for animals receiving lineage negative selected cells (45%) and fresh bone marrow cells (30%). Control irradiated animals receiving no cells had a 100% mortality rate. Cytokines have failed to similarly rescue similarly lethally irradiated animals and no functional donor bone marrow engraftment could be demonstrated in these surviving animals. Microvesicles secreted by the delivered cells are likely responsible for the recovery of the host bone marrow leading to survival of these animals. We have demonstrated that fresh bone marrow (which includes lineage negative cells) and mesenchymal stem cells produce ample amounts of microvesicles that could accomplish this effect. In another study, C57/CJ6 (GFP$^-$) mice were lethally irradiated with two cycles of 400 cGy gamma irradiation to inhibit their hair growth and partially ablate their bone marrow. After irradiation, the backs of the mice were shaved and the mice were then in an approximately 2 cm area with an ablative fractional Erbium: YAG laser. After laser treatment, a plastic chamber was adhered to the skin and bone marrow derived cells obtained from a syngeneic GFP$^+$ transgenic mouse were added to the chamber. The GFP$^+$ bone marrow cells included, freshly harvested bone marrow cells, lineage negative selected bone marrow cells, mesenchymal stem cells and bone marrow complete cultured cells (as described in this application). In no animals was chimerism able to be achieved; detected by circulating GFP$^+$ cells 4 to 6 weeks after administration of cells. See FIG. 30. Animals receiving laser treatment alone had no to very minimal short stubby hair growth. FIG. 30 (A). In animals given bone marrow cells, there was significant, long lasting hair growth. FIGS. 30 (A & B). These findings were most dramatic in mice treated with GFP$^+$ lineage negative selected cells and total fresh GFP$^+$ bone marrow cells. Hair growth could be detected in 2 weeks and continued to grow for several months. Skin biopsies were taken in the area of new hair growth but no GFP$^+$ cells were detected. Functional engraftment of bone marrow cells could also not be detected in any animal by FACS analysis. FIG. 30 (C). As with the example in FIG. 29, cytokines have not been demonstrated to have this effect in restoring hair growth. Microvesicles secreted by the delivered cells are likely responsible for the stimulation of hair growth.

Example 16: Use of the Microvesicles of the Present Invention to Promote or Stimulate Angiogenesis and to Promote or Stimulate Fibroblast Proliferation Isolation of Bone Marrow Aspirate Microvesicles:

Approximately 25 ml of fresh whole bone marrow was obtained from AllCells, Inc. (Alameda, CA). The bone marrow was carefully placed into new 50 ml conical centrifuge tubes and centrifuged at 400×g for 30 minutes at room temperature. The supernatant was carefully removed (approximately 15 ml) and placed into new 50 ml conical centrifuge tubes (Thermo Fisher Scientific Inc., Weston, FL) and centrifuged at 2000×g for 30 minutes at 4° C. The supernatant was again carefully removed and placed into new 50 ml conical centrifuge tubes to which sterile alpha-minimum essential medium (α-MEM) (Mediatech Inc., Manassas, VA) was added in a 1:10 (Bone marrow supernatant to medium) ratio. To the solution, RNase and protease free polyethylene glycol average molecular weight 6000 (Sigma Aldrich, Saint Louis, MO) at 8.5 w/v % and sodium chloride (final concentration 0.4 M) were added. The solution was placed in a cold room at 4° C. overnight with rocking. The solution was centrifuged at 10000×g at 4° C. for 30 minutes. The supernatant was decanted and the microvesicle enriched pellet resuspended in phosphate-buffered saline (PBS). The microvesicle enriched solution was transferred to Amicon ultra-15 centrifugal filter units (nominal molecular weight limit 100 kDa) (Millipore, Billerica, MA) and centrifuged at 5000×g for 30 minutes. The filter units were washed with phosphate-buffered saline and centrifuged again at 5000×g for 30 minutes. The concentrated sample was recovered (approximately 200-400 μl) from the bottom of the filter device.

Angiogenesis Assay:

Angiogenesis was measured using an endothelial tube formation assay (Invitrogen Life Technologies, Grand Island, NY). Cryopreserved primary Human Umbilical Vein Endothelial cells (HUVEC) (Invitrogen Life Technologies) were grown in a 75-cm tissue-culture flask for 6 days in Medium 200PRF supplemented with 2% low serum growth supplement (Invitrogen Life Technologies). Cells were then plated at a density of 3×10<4>in a 24 well tissue culture plate containing medium without supplement. HUVEC Cells were subsequently treated with bone marrow microvesicles (approximately 100 μg). PBS was used as the vehicle control. Treated cells were incubated for 6 hours at 37° C. and 5% $CO_2$. Calcein AM fluorescent dye at a concentration of 2 μg/ml was used for visualization of tube formation. Fluorescent images were captured with an inverted IX81 Olympus microscope (Olympus America, Center Valley, PA). Bone marrow MV showed significant tube formation capacity as compared to the vehicle (PBS) control (see FIG. 31).

Growth Assay:

Normal adult fibroblasts were plated onto 24-well plates (10000 cells/well) in growth media (5% FBS, 1% glutamine, 1% Penicillin/Streptomycin) for the assays. After overnight incubation, three wells were randomly selected and the cells were stained with NucBlue Live ReadyProbes Reagent (Invitrogen Life technologies) (Day 0). Fluorescent images were captured using the EVOS FL Auto Cell Imaging System (Invitrogen Life technologies). Fibroblasts were re-fed with fresh medium containing bone marrow-derived microvesicles (approximately 100 μg) or PBS (vehicle control) and after three days (Day 3), cells were stained and imaged. Bone marrow-derived microvesicle treated fibroblasts increased approximately three fold in number (compared to Day 0) and at a significant greater rate than the vehicle control (FIG. 32, panel A and FIG. 32, panel B).

Example 17: EV-Mediated Delivery of Bioactive Materials to Target Cells

According to certain exemplary embodiments of the invention, EVs described herein are useful for delivering one or more bioactive agent (e.g., collagen VII proteins or peptides, collagen VII mRNA, STAT3-signalling activators, canonical Wnt activators and the like) to a target cell. This example demonstrates delivery of EVs to RDEB fibroblast cells that were deficient in COL7A1 expression compared to wild-type fibroblast cells. The EVs stimulated collagen VII expression in the RDEB fibroblasts. The EVs also stimulated the expression of markers related to wound healing in the RDEB fibroblasts.

FIG. 44 shows the validation of an in vitro cell line derived from an infant diagnosed as having RDEB (Hallopeau-Siemens type). Vesicle exchange was observed between BM-MSCs and RDEB fibroblasts (FIG. 45). Collagen VII was co-isolated with BM-MSC EVs (FIG. 46), and COL7A1 mRNA was enriched in MB-MSC EVs (FIG. 47).

RDEB fibroblasts were treated with BM-MSC EVs on day 1, were washed on day three, and showed an increase in collagen VII expression on day six (FIG. 48). A chemoselective ligation assay (utilizing "click iT" reaction chemistry) revealed the production of new collagen VII from RDEB fibroblasts following co-treatment with BM-MSC EVs (FIG. 49). BM-MSC EVs were shown to increase in vitro surrogate assays related to wound healing (e.g., proliferation and trypsin-resistance) of RDEB fibroblasts (FIG. 50).

BM-MSCs that were delivered in saline to burn patients in a clinical trial were shown to secrete large numbers of EVs (CD63 positive) in saline within hours (shown, 4 hours) (FIG. 51).

A model of BM-MSC-mediated wound healing is set forth in FIG. 52.

Example 18: Extracellular Vesicles Derived from Bone Marrow Mesenchymal Stem Cells in the Treatment of Recessive Dystrophic Epidermolysis Bullosa Local and intravenous injections of allogeneic bone marrow-derived mesenchymal stem cells (BM-MSCs) have been shown to promote wound healing in Recessive Dystrophic Epidermolysis Bullosa (RDEB). We have described that extracellular vesicles (EVs) derived from BM-MSCs (BM-MSC EVs) are largely responsible for the healing effects attributed to BM-MSCs. We have also discovered that EVs can transfer collagen VII (Col VII) to RDEB cells. We propose the first clinical trial where BM-MSC EVs from healthy allogeneic donors will be applied topically to wounds in RDEB patients, maximizing safety and comfort for the patient while enhancing wound healing. Treating with EVs has many advantages over cellular therapy including much lower risks of genetic instability and malignant transformation. We will secure FDA Investigational New Drug (IND) approval and manufacture clinical grade BM-MSC EVs for an open-label dose-escalation Phase I study of topically applied allogeneic BM-MSC-derived EVs in 30 RDEB patients.

Specific Aims

Aim 1—Gain IND Approval from FDA for a Phase I Dose Escalation Trial of Topically Applied BM-MSCEVs in RDEB Patients and Prepare Optimal Clinical Grade BM-MSC-EVs We will apply specific criteria for donor BM-MSC EV screening, selection and functional characterization for use in our Phase I clinical trial. This includes defining details of EV manufacturing and product characteristics for the IND as they relate specifically to RDEB. We will employ analyses found to be important in our stem cell based clinical trials and assess donors for BM-MSC EVs based on functional performance on recipient RDEB cells. We will select optimal BM-MSC donors and manufacture BM-MSC EVs to be used for treatment of RDEB patients in our trial.

Aim 2—Conduct an Open-Label, Dose-Escalation Clinical Trial of Topical, Allogeneic BM-MSC-Derived EVs in the Treatment of Wounds in 30 RDEB Patients Dosing will be based on the PI's successful clinical trial of topically applied BM-MSCs to burn patients. There will be 3, serially escalating, dosing groups with 10 patients to complete each group. The dosing schedule will be first dose at treatment day 0 with three additional doses given monthly (total of four treatments over three months). Primary outcomes will assess safety and tolerability of topically applied BM-MSC EV; secondary outcomes will assess wound healing, pain, itch, and cosmesis (including pigment, scar assessment and evidence of tissue regeneration). Integrium Contract Research Organization will assist in the clinical trial.

Research Strategy

Aim 1—Gain IND approval from FDA for use of topical BM-MSC-derived extracellular vesicles (EVs) for Phase I clinical trial to treat wounds of RDEB patients.

Direct application of bone marrow-derived stem and progenitor cells to burns and recalcitrant chronic non-healing wounds lead to wound closure and dermal rebuilding. Chronic wound patients (of greater than one year in duration) were treated with bone marrow stem and progenitor cells. MSC's represented approximately 30% of the cells given to patients. Evidence of healing was observed in all treated patients, with many achieving full closure of their wounds. Some subjects have remained healed for more than 7 years (eventually lost to follow-up). Among the clinical findings noted were dermal rebuilding and the lack of scarring in healing wounds noted both clinically and histologically. Clinically, there is elevation of the wound bed with little to no atrophy/depression on closure of healed wounds (FIG. 33). Histologic evidence supports dermal rebuilding in treated wounds.

Microscopic findings included increased collagen formation and ground substance deposition. Among the most surprising observations were the restoration of structures such as reticulin and elastic fibers (FIG. 34). These fibers are characteristically lost in the healing of even uncomplicated acute and chronic wounds. Overall, these findings support the ability to induce healing in a non-healing wound, restore tissue volume deficits, stimulate tissue regeneration and greatly reduce scarring using topically applied bone marrow derived stem cells, with no adverse events.

Allogeneic BM-MSCs applied topically to burn wounds showed evidence of rapid epithelialization, reduced scarring, restoration of pigment and regeneration of hair follicles. No related severe adverse events nor evidence of rejection were observed. Follicular regeneration (FIG. 35) consistent with tissue regeneration was noted in after topical application of BM-MSCs to burn wounds. Regeneration of hair follicles was, however, not observed in non-treated areas of the burn injury. Dramatic re-pigmentation (FIG. 36) indicative of tissue regeneration has also been observed.

The rapid re-pigmentation noted in patients is unheard of by any other means of treatment as these wounds typically undergo a prolonged (often permanent) period of post burn leukoderma. Restoration of elasticity in burned skin was also an extraordinary finding (FIG. 37). What is especially remarkable about these results are that they occur after only short term topical application of BM-MSCs. Especially within this time frame is not likely that cells will survive long and/or engraft by this means of administration. This strongly indicates that the delivered cells are able to rapidly communicate complex messages leading to a robust regenerative and healing effect. Naked cytokines, nucleic acids and transcription factors would not survive long in the burn wound environment nor is it feasible that single factors would be capable of generating such a complex response.

Without intending to be bound by scientific theory, it was hypothesized that membrane bound EVs are capable of generating such a clinical response. In examining just the saline vehicle in which the cells are delivered to patients (after removal of cells) we have found more than $1.6 \times 10^{11}$ EV particles/mL present, confirming that we are delivering substantial numbers of EVs to patients. The EVs within the samples administered to patients are intact and possess characteristic EV markers. Recently, we have published that EVs stimulate normal and chronic wound fibroblast proliferation and migration, and enhances angiogenesis via activation of STAT5-mediated target genes (Shabbir A, Cox A, Rodriguez-Menocal L, Salgado M, Van Badiavas E. Mesenchymal Stem Cell Exosomes Induce Proliferation and Migration of Normal and Chronic Wound Fibroblasts, and Enhance Angiogenesis In Vitro. Stem Cells Dev 2015; 24:1635-47). Our preclinical studies also strongly support BM-MSC EV stimulation of wound healing and tissue regeneration (FIGS. 38 and 39). Evidence of tissue regeneration in our preclinical studies, such as nerve growth, have not been realized by other means. In particular, our preclinical studies have demonstrated that other methods of EV isolation damage vesicles which lead to the generation of an undesirable inflammatory response. Our novel method does not damage EVs and has been shown to induce rapid healing without the generation of an inflammatory response (FIG. 40). Preliminary data indicated that these vesicles, aside from delivering pro-healing factors, could transport Col VII protein and functional COL7A1 mRNA to RDEB fibroblasts (FIGS. 41 and 42).

In an assay to capture Col VII protein in combination with a chemoselective ligation reaction (Click iT®, ThermoFisher) we found RDEB fibroblasts were actually induced by BM-MSC EVs (at a dose of 10 µg/mL) to make new Col VII protein (FIG. 42). BM-MSC EVs significantly promote both RDEB proliferation and resistance to trypsin digestion (FIG. 43). These are standard assays used to assess gain-of-function and the pro-wound healing potential of RDEB dermal fibroblasts. These data provide evidence that BM-MSC EVs have benefits for RDEB in addition to their potential to improve wound healing. To gain IND approval for the clinical trial, we will establish manufacturing within contracted GMP manufacturing facilities that the PI has successfully worked with in previous trials. Aside from meeting general manufacturing requirements, we will address issues relating specifically to the treatment of RDEB. We will establish criteria for donor screening and selecting to optimize potential pro-regenerative activities of EVs. BM-MSC EV product characteristics will be defined. These parameters include protein concentrations, EV size distributions (e.g., using NanoSight NS300), surface marker characterization, removal of reagents used during manufacturing, and stability testing of the product. Using mass spectrometry and RNA sequencing, we will define protein and RNA cargo contents of several BM-MSC EV donors, correlating cargo with functional assay performance. BM-MSC EV functional activities will be defined on recipient RDEB cells, including in vitro studies to establish potency for wound healing and reversal of phenotype, including RDEB fibroblast proliferation and trypsin resistance assays. Additionally, endothelial angiogenesis assays will be examined in vitro.

Aim 2—Conduct an Open-Label, Dose-Escalation, Clinical Trial of Topical, Allogeneic BM-MSC-Derived EVs in the Treatment of Wounds in 30 RDEB Patients Approach:

The clinical trial will be an open-label, pilot study with three escalating treatment dose groups (10 patients per dose level). Investigators will identify target lesions between 5 and 50 cm$^2$ for treatment. EVs in saline will be applied underneath a thin silicone sheet dressing as a primary layer with an overlying secondary standard-of-care wound dressings. Control wounds will be treated with saline underneath a silicone sheet. Treatment frequency will at baseline, 4 weeks, 8 weeks, and 12 weeks. Dose levels will be derived from levels administered in the PI's burn trial. Digital images will be taken of treatment and control wounds. Treatment and control wounds will be measured using the Silhouette® device.

Outcomes will be assessed monthly for 12 weeks. Given our previous experience we expect to see a greater than 50% stimulation in healing. Clinically and from the standpoint of laboratory variation, we have assumed a pooled standard deviation of 20. Here a statistical power (not to be confused with probability) of 0.8 is recommended for clinical studies examining differences in this range (Breau R H, Carnat T A, Gaboury I. Inadequate statistical power of negative clinical trials in urological literature. The Journal of urology 2006; 176:263-6; Ichihara K, Boyd J C. An appraisal of statistical procedures used in derivation of reference intervals. Clinical chemistry and laboratory medicine: CCLM/FESCC 2010; 48:1537-51). In fact, evaluating differences of greater than 50% could require a statistical power of less than 0.8. The probability that a chance difference will be called significant is denoted by a (type I error) and typically should have a threshold of 0.05, below which a p value is deemed significant. The chance of missing a real difference (type II error) is designated by R. With these values, which we think are realistic, we have calculated the following sample size (Table 1) that will be required. The a refers to the probability that a chance difference will be called significant. As is customary, the threshold is 0.05 (95% confidence level), below which a p value is deemed significant. The values in Table 1 are for two-tailed tests. The sample size chosen of 10 patients per group will be more than adequate even when increasing the statistical power well beyond the recommended 0.8 to 0.95. While this is more stringent than we might need, it does ensure that we have proper statistical power with the number of subjects proposed.

TABLE 1

| | | Number of Patients | | | |
|---|---|---|---|---|---|
| Power | β | $\alpha = 0.10$ | $\alpha = 0.05$ | $\alpha = 0.02$ | $\alpha = 0.01$ |
| 0.80 | 0.2 | 3 | 4 | 5 | 6 |
| 0.90 | 0.1 | 4 | 5 | 6 | 7 |
| 0.95 | 0.05 | 5 | 6 | 7 | 8 |

Eligibility Criteria:

Key inclusion criteria includes: Male or female patients, 12 years or older at time of screening, and given consent with guardian, if under 18 years of age; Have confirmed RDEB diagnosis, as defined by clinical presentation and histologic confirmation; Have at least 1 active wound between 5 and 50 cm$^2$ on arms and/or legs; Females of childbearing potential must have a negative urine or serum pregnancy test at screening and be using an acceptable form of birth control (oral/implant/injectable/transdermal contraceptives, intrauterine device, or other forms of birth control). Key exclusion criteria will include: Clinical evidence of infection; Concurrent immunosuppressive therapy of any kind for any reason.

Primary Outcome Measures:

The following primary outcome measures will be assessed.

1) Screening for and documenting all adverse events, particularly those suspected to be related to treatment.

2) Characterization and analysis of all reported related adverse events.

3) Evaluating participants that have discontinued due to voluntary withdrawal or intolerance of the treatment.

Of note, in this application we are proposing the use of EVs derived from allogeneic BM-MSCs in multiple doses to improve wound healing and possibly introduce Col VII in RDEB wounds. The EU and US clinical registries list well over 1,000 clinical trials worldwide using BM-MSCs and therefore the paracrine materials they produce (including EVs) with approximately half of all studies employing allogeneic sources. To date, no serious related adverse events have been reported. In our trial using allogeneic BM-MSCs in burn patients we have not detected any evidence of a related adverse event nor immune response to the delivered material which we know contains ample amounts of BM-MSC EVs. Analysis of an immune response in our study includes a sensitive ELISA assay cleared by the FDA which will detect minute subclinical evidence of an immune response in mixed lymphocyte reactions. Despite giving multiple doses in our trial, we have not detected any immune response in these assays. This is however not unexpected as BM-MSCs are known to have immune modulatory properties (Bartholomew A, Polchert D, Szilagyi E, Douglas G W, Kenyon N. Mesenchymal stem cells in the induction of transplantation tolerance. Transplantation 2009; 87:S55-7; Siegel G, Schafer R, Dazzi F. The immunosuppressive properties of mesenchymal stem cells. Transplantation 2009; 87:545-9; Sundin M, Barrett A J, Ringden 0, et al. HSCT recipients have specific tolerance to MSC but not to the MSC donor. J Immunother 2009; 32:755-64) which have been shown to be mediated by the EVs they produce (Bruno S, Deregibus M C, Camussi G. The secretome of mesenchymal stromal cells: Role of extracellular vesicles in immunomodulation. Immunology letters 2015; 168:154-8; Chen W, Huang Y, Han J, et al. Immunomodulatory effects of mesenchymal stromal cells-derived exosome. Immunologic research 2016; 64:831-40; Li X, Liu L, Yang J, et al. Exosome Derived From Human Umbilical Cord Mesenchymal Stem Cell Mediates MiR-181c Attenuating Burn-induced Excessive Inflammation. EBioMedicine 2016; 8:72-82). We believe that carefully moving forward with an EV based therapy for RDEB is justified given that numerous trials, including our own, have been delivering allogeneic mesenchymal stem cell based EVs for years without evidence of immune response or rejection. We will of course monitor patients very closely for any evidence of immune response or rejection using measures well established in our trials. As we have recently found that BM-MSC EVs can deliver Col VII and induce RDEB cells to make Col VII, a question has been raised as to the potential for patients to develop antibodies to Col VII. This has been a concern in many clinical trials performed on RDEB patients but none have demonstrated an adverse response even in trials where Col VII antibodies were detected (Petrof, infra). In pre-clinical trials directly administering Col VII protein, even when circulating antibodies to Col VII were detected, worsening of disease, increased blistering and binding of these antibodies to skin was not observed (Riazifar, infra; Palazzi X, Marchal T, Chabanne L, Spadafora A, Magnol J P, Meneguzzi G. Inherited dystrophic epidermolysis bullosa in inbred dogs: A spontaneous animal model for somatic gene therapy. J Invest Dermatol 2000; 115:135-7; South A P, Uitto J. Type VII Collagen Replacement Therapy in Recessive Dystrophic Epidermolysis Bullosa-How Much, How Often? J Invest Dermatol 2016; 136:1079-81; Woodley D T, Cogan J, Wang X, et al. De novo anti-type VII collagen antibodies in patients with recessive dystrophic epidermolysis bullosa. J Invest Dermatol 2014; 134:1138-40). BM-MSC trials in RDEB patients also failed to demonstrate worsening of disease, increased blistering or evidence of induction of autoimmunity, even when the presence of Col VII could be established and/or anti-collagen antibodies could be detected (El-Darouti M, Fawzy M, Amin I, et al. Treatment of dystrophic epidermolysis bullosa with bone marrow non-hematopoeitic stem cells: a randomized controlled trial. Dermatol Ther 2016; 29:96-100; Riazifar M, Pone E J, Lotvall J, Zhao W. Stem Cell Extracellular Vesicles: Extended Messages of Regeneration. Annu Rev Pharmacol Toxicol 2017; 57:125-54; Petrof G, Lwin S M, Martinez-Queipo M, et al. Potential of Systemic Allogeneic Mesenchymal Stromal Cell Therapy for Children with Recessive Dystrophic Epidermolysis Bullosa. J Invest Dermatol 2015; 135:2319-21). Both chemical (Woodley, infra) and bone marrow stem transplantation (Wagner J E, Ishida-Yamamoto A, McGrath J A, et al. Bone marrow transplantation for recessive dystrophic epidermolysis bullosa. The New England journal of medicine 2010; 363:629-39) induced expression of Col VII in RDEB patients could not establish any concern about induced anti-Col VII antibodies in treated patients. This is not surprising as more than half of RDEB patients normally express the predominant antigenic portions of Col VII responsible for antibody production (Woodley D T, Cogan J, Hou Y, et al. Gentamicin induces functional type VII collagen in recessive dystrophic epidermolysis bullosa patients. J Clin Invest 2017; Jones D A, Hunt S W, 3rd, Prisayanh P S, Briggaman R A, Gammon W R. Immunodominant autoepitopes of type VII collagen are short, paired peptide sequences within the fibronectin type III homology region of the noncollagenous (NC1) domain. J Invest Dermatol 1995; 104:231-5; Lapiere J C, Woodley D T, Parente M G, et al. Epitope mapping of type VII collagen. Identification of discrete peptide sequences recognized by sera from patients with acquired epidermolysis bullosa. J Clin Invest 1993; 92:1831-9; Pfendner E, Uitto J, Fine J D. Epidermolysis bullosa carrier frequencies in the US population. J Invest Dermatol 2001; 116:483-4).

The findings that many RDEB patients undergo focal reverse mosaicism (with areas durable skin containing of intact Col VII) also provides strong evidence that introduction of Col VII into RDEB patients is not likely induce a pathogenic response. Even so, if the production of Col VII antibodies were to produce a clinically relevant effect, it would more resemble a form of epidermolysis bullosa acquisita; a much more manageable disease than RDEB. It also needs to pointed out that we are proposing the use EV's and not stem cells. Stem cells have the ability to engraft and are not retrievable. EV's are not viable, cannot persist and do not replicate. Therefore, if we detect any evidence or suspicion of an adverse outcome (including rising anti Col VII antibody titers), the treatment would be stopped and is reversible.

Secondary Outcome Measures:

The following secondary outcome measures will be assessed:

1) Blister/erosion reduction based on change in body surface area index (BSAI).

2) Target wound size reduction or closure. Wound size reduction is an assessment to determine possible efficacy of the EV treatment. Target wounds will be measured using Silhouette® (Aranz Medical), an FDA-approved medical device wound imaging, 3D measurement and documentation system using noninvasive laser technology providing accurate, precise and repeatable wound assessments.

3) Physician Assessment of Individual Signs—this scale evaluates blistering and erosions, oozing/crusting/weeping, pruritis, erythema on unblistered surrounding skin and pain. Body areas will include head/neck, upper limbs, trunk and lower limbs.

4) Epidermolysis Bullosa Disease Activity and Scarring Index (EBDASI).

5) VAS Pain Score questionnaire and pain medication use.

6) ItchyQuant scale score (validated scale to assess itch) (Haydek C G, Love E, Mollanazar N K, et al. Validation and Banding of the ItchyQuant: A Self-Report Itch Severity Scale. J. Invest. Dermatol. 2017; 137:57-61.).

7) Children's Dermatology Life Quality Index (CDLQI). Initial trial site is the University of Miami (with world renowned Pediatric Dermatologist Dr. Lawrence Schachner). Secondary sites will be determined.

Although the various aspects of the invention have been illustrated above by reference to examples and preferred embodiments, it will be appreciated that the scope of the invention is defined not by the foregoing description but by the following claims properly construed under principles of patent law.

What is claimed:

1. A method of treating epidermolysis bullosa in a human subject in need thereof comprising:

administering to the subject a pharmaceutical composition comprising a therapeutically effective amount of an enriched population of structurally and functionally intact heterogeneous population of vesicles collected from polyethylene glycol (PEG) precipitation from a biological fluid, wherein the heterogeneous population of vesicles are combined with a pharmaceutically acceptable carrier or excipient:

wherein the isolated heterogeneous population of vesicles comprise a combination of exosomes and at least extracellular vesicles, ectosomes, microparticles, nanovesicles, shedding vesicles, apoptotic bodies, and/or membrane particles; wherein the heterogeneous population of vesicles comprise one or more bioactive agents comprising RNA, DNA, lipid, carbohydrate, metabolite, peptide, protein and combinations thereof;

wherein the biological fluid comprises mesenchymal stem cells;

wherein the method of treating results in lower levels of inflammation and higher levels of tissue regeneration than a method of administering microvesicles isolated by ultracentrifugation; and wherein the method alleviates or reduces one or more symptoms of epidermolysis bullosa in the subject.

2. The method of claim 1, wherein the average molecular weight of the polyethylene glycol is about 6,000 Da, about 8,000 Da, about 10,000 Da or about 20,000 Da.

3. The method of claim 1, wherein the one or more symptoms of epidermolysis bullosa are any combination of thickened calluses, epidermal blistering, blistering of oral mucosa, thickened fingernails and/or toenails, sepsis, malnutrition, dehydration, electrolyte imbalance, obstructive airway complications, defective collagen VII expression, anemia, esophageal strictures, growth retardation, webbing or fusion of fingers and/or toes, malformation of teeth, microstomia and corneal abrasions.

4. The method of claim 3, wherein the epidermal blistering is of the hands, the feet, the elbows and/or the knees.

5. The method of claim 1, wherein treatment comprises increasing collagen VII expression in the subject and/or increasing expression of markers related to wound healing.

6. The method of claim 1, wherein the pharmaceutical composition is applied topically to the skin of the subject.

7. The method of claim 1, wherein the isolated heterogeneous population of vesicles range in size from 2 nm to 5000 nm.

8. A method of treating dystrophic epidermolysis bullosa (DEB) in a human subject in need thereof comprising:

administering to the subject a pharmaceutical composition comprising a therapeutically effective amount of a heterogeneous population of vesicles in order to alleviate or reduce one or more symptoms of DEB in the subject, wherein the heterogeneous population of vesicles are isolated by polyethylene glycol (PEG) precipitation from a biological fluid to obtain structurally and functionally intact isolated heterogeneous population of vesicles, wherein the isolated heterogeneous population of vesicles comprise a combination of exosomes and at least extracellular vesicles, ectosomes, microparticles, nanovesicles, shedding vesicles, apoptotic bodies, and/or membrane particles;

wherein the biological fluid comprises mesenchymal stem cells, wherein the isolated heterogeneous population of vesicles are combined with a pharmaceutically acceptable carrier or excipient.

9. The method of claim 8, wherein the dystrophic epidermolysis bullosa (DEB) is autosomal dominant (DDEB) or autosomal recessive (RDEB).

10. The method of claim 8, wherein the average molecular weight of the polyethylene glycol is about 6,000 Da, about 8,000 Da, about 10,000 Da or about 20,000 Da.

11. The method of claim 8, wherein the one or more symptoms of epidermolysis bullosa are selected from the group consisting of any combination of thickened calluses, epidermal blistering, blistering of oral mucosa, thickened fingernails and/or toenails, sepsis, malnutrition, dehydration, electrolyte imbalance, obstructive airway complications, defective collagen VII expression, anemia, esophageal strictures, growth retardation, webbing or fusion of fingers and/or toes, malformation of teeth, microstomia and corneal abrasions.

12. The method of claim 11, wherein the epidermal blistering is of the hands, the feet, the elbows and/or the knees.

13. The method of claim 8, wherein treatment comprises increasing collagen VII expression in the subject and/or increasing expression of markers related to wound healing.

14. The method of claim 8, wherein the pharmaceutical composition is applied topically to the skin of the subject.

15. The method of claim 8, wherein the isolated heterogeneous population of vesicles range in size from 2 nm to 5000 nm.

16. A method of treating epidermolysis bullosa in a human subject in need thereof comprising:

(a) administering a therapeutically effective amount of a pharmaceutical composition comprising structurally and functionally intact isolated heterogeneous population of vesicles comprising one or more bioactive agents to the subject; and (b) alleviating or reducing one or more symptoms of epidermolysis bullosa, wherein the heterogeneous population of vesicles have been isolated by polyethylene glycol (PEG) precipitation from a biological fluid to obtain structurally and functionally intact isolated heterogeneous population of vesicles that are combined with a pharmaceutically acceptable carrier or excipient to produce the pharmaceutical composition prior to administration to the subject, wherein the biological fluid comprises mesenchymal stem cells, wherein the pharmaceutical composition contains isolated heterogeneous population of vesicles ranging in size from 2 nm to 5000 nm, wherein the isolated heterogeneous population of vesicles comprise a combination of exosomes and at least extracellular vesicles, ectosomes, microparticles, nanovesicles, shedding vesicles, apoptotic bodies, and/or membrane particles, wherein the isolated heterogeneous population of vesicles are less inflammatory than those produced using ultracentrifugation, wherein the isolated heterogeneous population of vesicles are administered topically, wherein the structurally and functionally intact isolated heterogeneous population of vesicles comprise one or more bioactive agents comprising RNA, DNA, lipid, carbohydrate, metabolite, peptide, protein and combinations thereof, and wherein the method results in lower levels of inflammation and higher levels of tissue regeneration than a method of administering microvesicles isolated by ultracentrifugation.

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
agacctcaca gtaaaaatag gtga                                                       24

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ctgatgggac ccactccatc                                                           20

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
gaagacctca cagtaaaaat aggtg                                                      25

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ctgatgggac ccactccatc                                                           20